(12) United States Patent
Nikolin et al.

(10) Patent No.: US 11,730,805 B2
(45) Date of Patent: Aug. 22, 2023

(54) PARAMYXOVIRIDAE EXPRESSION SYSTEM

(71) Applicant: Boehringer Ingelheim Vetmedica GmbH, Ingelheim am Rhein (DE)

(72) Inventors: Veljko Nikolin, Hannover (DE); Alissa Benter, Hannover (DE); Andreas Gallei, Wedemark (DE)

(73) Assignee: Boehringer Ingelheim Vetmedica GmbH

( * ) Notice: Subject to any disclaimer, the term of this patent is extended or adjusted under 35 U.S.C. 154(b) by 242 days.

(21) Appl. No.: 16/649,456

(22) PCT Filed: Sep. 20, 2018

(86) PCT No.: PCT/EP2018/075542
§ 371 (c)(1),
(2) Date: Mar. 20, 2020

(87) PCT Pub. No.: WO2019/057859
PCT Pub. Date: Mar. 28, 2019

(65) Prior Publication Data
US 2020/0276298 A1 Sep. 3, 2020

(30) Foreign Application Priority Data
Sep. 23, 2017 (EP) ..................... 17192791

(51) Int. Cl.
*A61K 39/155* (2006.01)
*C12N 15/86* (2006.01)
*A61K 39/00* (2006.01)

(52) U.S. Cl.
CPC ............ *A61K 39/155* (2013.01); *C12N 15/86* (2013.01); *A61K 2039/53* (2013.01);
(Continued)

(58) Field of Classification Search
None
See application file for complete search history.

(56) References Cited

U.S. PATENT DOCUMENTS

| | | | |
|---|---|---|---|
| 10,905,758 B2 * | 2/2021 | Nikolin | ............... A61K 39/12 |
| 2003/0224017 A1 | 12/2003 | Samal | |
| 2020/0276298 A1 * | 9/2020 | Nikolin | ............... A61K 39/12 |

FOREIGN PATENT DOCUMENTS

| | | |
|---|---|---|
| CN | 101 426 917 A | 5/2009 |
| ES | 2358849 T3 | 5/2011 |

(Continued)

OTHER PUBLICATIONS

Sequence alignment of SEQ ID No. 2 with Geneseq db access No. ABK15038 by Parks et al 2002.*

(Continued)

*Primary Examiner* — Shanon A. Foley
(74) *Attorney, Agent, or Firm* — Suzanne Shope

(57) ABSTRACT

The present invention relates to the field of (vector) vaccines, and especially to an enhanced arrangement of nucleotide sequences for expressing a Paramyxoviridae virus containing an exogenous gene of interest. The present invention further concerns related expression cassettes and vectors, which are suitable to express genes of interest, especially antigen encoding sequences. The viral vectors of the present invention are useful for producing an immunogenic composition or vaccine.

20 Claims, 6 Drawing Sheets
Specification includes a Sequence Listing.

(52) U.S. Cl.
CPC ............... *A61K 2039/552* (2013.01); *C12N 2750/14034* (2013.01); *C12N 2760/16034* (2013.01); *C12N 2760/18421* (2013.01); *C12N 2760/18434* (2013.01); *C12N 2760/18443* (2013.01); *C12N 2770/20022* (2013.01); *C12N 2770/20034* (2013.01)

(56) References Cited

FOREIGN PATENT DOCUMENTS

| WO | 2002/000883 A3 | 1/2002 |
|----|----------------|--------|
| WO | 2009/035971 A3 | 3/2009 |
| WO | 2010/036948 A2 | 4/2010 |
| WO | 2016/071306 A1 | 5/2016 |
| WO | 2017/029360 A1 | 2/2017 |
| WO | 2017/053851 A1 | 3/2017 |
| WO | 2017053374 A1  | 3/2017 |
| WO | 2017058521 A1  | 4/2017 |

OTHER PUBLICATIONS

Sequence alignment of SEQ ID No. 9 with Geneseq db access No. ABK15038 by Parks et al 2002.*

Sequence alignment of SEQ ID No. 15 with Geneseq db access No. BDU41844 on 2017.*

Huang et al. (Journal of Virology. 2004; 78 (18): 10054-10063).*

Li et al. (Virus Genes. 2015; 50: 434-441).*

Nakaya et al., "Recombinant Newcastle Disease Virus as a Vaccine Vector", Journal of Virology, 2001, pp. 11868-11873; DOI 10.1128/JVI.75.23.11868-11873.2001 (vol. 82, Jan. 1, 2003 (Jan. 1, 2002), pp. 899-906).

Parks et al., "Expression of a foreign gene by recombinant canine distemper virus recovered from cloned DNAs", Virus Research, 2002, vol. 83 (1-2), pp. 131-147.

Von Messling et al. "Canine distemper virus and measles virus fusion glycoprotein trimers: partial membrane-proximal ectodomain cleavage enhances function." J. Virol., 2002, vol. 78(15), pp. 7894-7903.

Wang et al., "Recombinant canine distemper virus serves as bivalent live vaccine against rabies and canine distemper.", Vaccine 2012, vol. 30(34), pp. 5067-5072.

Glover et al., "Canine Parvovirus (CPV) type 2b vaccine protect puppies with maternal antibodies to CPV when challenged with virulent CPV 2 C virus.", International Journal of Applied Research in Veterinary Medicine, 2012, vol. 10, pp. 217-224.

Taguchi et al., "Antibody titers for canine parvovirus type-2, canine distemper virus, and canine adenovirus type-1 in adult household dogs.", The Canadian Veterinary Journal, 2011, vol. 52(9), pp. 983-986.

* cited by examiner

```
                            SEQUENCE LISTING

<160> NUMBER OF SEQ ID NOS: 47

<210> SEQ ID NO 1
<211> LENGTH: 59
<212> TYPE: RNA
<213> ORGANISM: canine distemper virus

<400> SEQUENCE: 1
uuuuuuauaa ugaguuuaga augauaauug uugacugaug caggacuggu cuugaauau      59

<210> SEQ ID NO 2
<211> LENGTH: 72
<212> TYPE: RNA
<213> ORGANISM: canine distemper virus

<400> SEQUENCE: 2
uuuuuuauaa uugcuuuuaa gcgauaguga aagcaguuuu gcgccgguua guagauuagu     60
caacgcuaca ga                                                        72

<210> SEQ ID NO 3
<211> LENGTH: 407
<212> TYPE: RNA
<213> ORGANISM: canine distemper virus

<400> SEQUENCE: 3
uuuugauuaa uuauuaauga gcugugauag aaagauggac agucauaacu ccgugaaaca    60
agacuacuag ugauggcuug agaucaggca agugcguggg aguauaacug uuaaagugag   120 auccuauaa gcgaagcuca aaaccccagg cauccauuca uuucuugguc cgauaaugau    180
caacccaauc uuaagcaaga acuguuuuga uucagcuauu uucauauuga ggcgucacug   240
gaauuguggg cacggauggg caguuuagaa accuauaggc cacgcucaaa augcaggagc   300
aacaucuagc cagucgauau uuauacccuc aauccucgcu ugcggggauc aagggaucuu   360
gggcaaugcu acuaaggcgu uugaguuuua guucaugaac uaaugau                 407

<210> SEQ ID NO 4
<211> LENGTH: 130
<212> TYPE: RNA
<213> ORGANISM: canine distemper virus

<400> SEQUENCE: 4
uuuucuuuaa uuacgauaau cauggucagu cuuuuccaau guuuauugca guugagugac    60
```

-continued

```
ucuugaagaa aauugggcgg gguuaauaga uaucaaaucu ggcaaucaag cgagauauau      120
gaccagaaua                                                            130
```

<210> SEQ ID NO 5
<211> LENGTH: 58
<212> TYPE: RNA
<213> ORGANISM: canine distemper virus

<400> SEQUENCE: 5

```
ggauuuuuca ccauacucau caugccuaag uccaauugag auguguauca uuauacug        58
```

<210> SEQ ID NO 6
<211> LENGTH: 65
<212> TYPE: RNA
<213> ORGANISM: canine distemper virus

<400> SEQUENCE: 6

```
uuuuuuucg uauaaccaag uuugauagca augaauagua ggggcuagg agccagacua       60 accug                                                                 65
```

<210> SEQ ID NO 7
<211> LENGTH: 20
<212> TYPE: RNA
<213> ORGANISM: canine distemper virus

<400> SEQUENCE: 7

```
ugcuggacua ccugaguccu                                                 20
```

<210> SEQ ID NO 8
<211> LENGTH: 52
<212> TYPE: RNA
<213> ORGANISM: canine distemper virus

<400> SEQUENCE: 8

```
auugguaggu cugaacccug accuuguucu cuaagguagg aucauugacc cu             52
```

<210> SEQ ID NO 9
<211> LENGTH: 59
<212> TYPE: RNA
<213> ORGANISM: canine distemper virus

<400> SEQUENCE: 9

```
uuagggauag aacggguggu cggaugaaug guugaucggg uuuguuggac cugggusccu     59
```

<210> SEQ ID NO 10
<211> LENGTH: 32
<212> TYPE: RNA
<213> ORGANISM: canine distemper virus

<400> SEQUENCE: 10

```
uuuuuaggag aggacuuagg cucuuguguc cu                                   32
```

<210> SEQ ID NO 11
<211> LENGTH: 85
<212> TYPE: RNA
<213> ORGANISM: canine distemper virus

<400> SEQUENCE: 11

```
ggggcuuggc uguuuguggg gguuccugcc uggccucggg cuggugacu ugguuggccu      60 guugacuugc uauguccugg acccu                                           85
```

```
<210> SEQ ID NO 12
<211> LENGTH: 66
<212> TYPE: RNA
<213> ORGANISM: canine distemper virus

<400> SEQUENCE: 12
ggcuaaaagg auccuggauc cuuaguuuuu uuauaaugcu ggagaugguu uaauucaauc    60
aucugu                                                              66

<210> SEQ ID NO 13
<211> LENGTH: 5
<212> TYPE: RNA
<213> ORGANISM: Artificial Sequence
<220> FEATURE:
<223> OTHER INFORMATION: encodes a Kozak sequence

<400> SEQUENCE: 13 ggugc                                                                5

<210> SEQ ID NO 14
<211> LENGTH: 3
<212> TYPE: RNA
<213> ORGANISM: canine distemper virus

<400> SEQUENCE: 14 aag                                                                  3

<210> SEQ ID NO 15
<211> LENGTH: 1755
<212> TYPE: RNA
<213> ORGANISM: Artificial Sequence
<220> FEATURE:
<223> OTHER INFORMATION: encodes a CPV VP2

<400> SEQUENCE: 15
uuaguacagc uuucgggggg ccagcuggga ccgcucgaac acgauuucca uuccgccgau    60
guugcugggc acguaguuga acugguuguc cacguugaug cucaucugcu ggauggggu    120 ccagguguga gaggcccgca gcuuggccuu gaacaccagc uugcccuucc accagaaguc   180
gcuguagguc acgauccggc ucauguuggc gcuggcguca gggucguacu cguuggucag   240
guugggggcc accuucacaa acagcuggcc agggcaguug uucuggcaca cgaaagggc   300 guucacaugc agccggggcu ucaggucggu gucgaacucu uugcccaga ucugccguu    360 gggguacacg gggggcacgu uguucagggc ggucagaggg ccguaggugu ugaagauauu   420 ggguaguug augccggucu ugccgccgau gggaucugu ggcagcagca cguugucguc    480
ggucacgggc agguugaagu ugauguucug aauccagucg cccucggggu aucugccggu   540 guccugguugg gcgauauagg ugaaccgcuc ggguguguccg ccgguggugg ugguuuucug   600
gccgugcugu cugccaaagg cguaucuggg guugccgucg gcgcccugau ucucaucggu   660
cugggcuccg ccucuuccgg cggcaauagg ugucuugaag gggcccuggg ugcuggccuc   720
gaagcuguag uaggggcgc uguagcccac uucggcaggc cgcaugauug ggccucggu   780 gauguaguug gucuugccca ucuguguac gccucccgc uuguccugcu gcacgccgau   840
auagccaaag uuggugccgc ccucggccug aggcagacug uucaggaaug ggggcaggcc   900
cagggcucua uuggucugcc aggugugggu cagccggcag gguugcagu cgaaaaagaa   960 ugugccugug gcgaacucgu cgccgguucu cagcagaugc acgggcacgc uguucucgau  1020 ggguguagaac ugcacgucgu cggggucggu gccguggugag auguugguag gggugccgcu  1080
```

| | |
|---|---|
| ggugccugug uggcugggga ucagggunucu gucccacugg aaguaguacc gccaggggu | 1140 |
| agggaugguug ggcuuccagg gguagaagcc cagugucucg cuccgcaugg cggcaggggu | 1200 |
| gaagggcaug guguuguugc uguccagagc caccaucagg gaggcgguca ggucguuguu | 1260 |
| guacaccuug guggggggcu guguggcgcu cucggacacg guuucagca ccacguugaa | 1320 |
| gauuuccugc ucgaaggaca ccaggugcag cucgcucaug uguucacga ucagcugcca | 1380 |
| gucgccgggg uugaaccaca cgccccaggc auuggcaucc accagggacc agggugucac | 1440 |
| gaucuggcg ugguaucgu ccagggccau guugccguuc acggcggucu ugccagguu | 1500 |
| guucacgacc acccgccggu aguucucgcu cucgggcaug uucaggugca ccagucugcu | 1560 |
| gcuguuggcg gugauuucca cccagccguu uuccaggaac uugaacucgg ucugguuguu | 1620 |
| gaaggugccg gugcuaauuc ccacuccgcc acuuccccu ccgccgccuc cgccagaucc | 1680 |
| auugccgcug ccgguggcuc ucucauuccg cacagcaggc ugucgccau caggcugcac | 1740 |
| ggcgccauca gacau | 1755 |

<210> SEQ ID NO 16
<211> LENGTH: 1701
<212> TYPE: RNA
<213> ORGANISM: Artificial Sequence
<220> FEATURE:
<223> OTHER INFORMATION: encodes a H3 of swine influenza virus

<400> SEQUENCE: 16

| | |
|---|---|
| ucaaaugcag auguuacagc gaauauugcc cuuugacag gcccacauga ugaaacccaa | 60 |
| ccaaacggcg cacagcagga agcagcuuau ggcaaagcug auccacagua uccagucccuu | 120 |
| auagccacuc uucagucca cgcuuuugau uggaagcgg uuauuaacug ccucaucgcg | 180 |
| guacucguug uggucuagg uuccguuucg gaugcucucc augcagcuau ugucgcacuu | 240 |
| guggaugaua uaaaaacacc cauauacccau gucucggcg uucucucgga guugcuucccg | 300 |
| ggucuucucg aagaguuuau ucaucucgcu gucggcagg ucaauggugu guuggauuuc | 360 |
| caaggcgacc aggagcucgg cauuguagcu ccacaggucg aucuuggugu ccuccacgua | 420 |
| gcgcucgagg ucuuggaugc ggcccuccac cucgcugaau ucuuucucua uuugguggaa | 480 |
| uuucucguuc gucuuuucaa ucacgcgguu aagcuugccg uugaucuggu ugauggcugc | 540 |
| uugcguggac uucagauccg cagcuuggcc gauccuuuca gaguucugau ggcggaagcc | 600 |
| guaccagccg uuaaccauuc ccucccagcc auucucaaug aaccugcga uugcgccaaa | 660 |
| aaugccccgu gucugucgcu cggggauguu gcgcaugccg guggcagcu ucagggguguu | 720 |
| cugcuugaug uacuuggggc acgcgccgua ggugaucuua uucacguucu ggaaaggcuu | 780 |
| gucguugggg augcugccau uggggugau gcauucgcua uugcagguugu cgauggggc | 840 |
| gucgcuccuc aucacacugc uuugccggu cugcaucuug aaguagccgc gugggcgau | 900 |
| aagauugcca uuagauugaa ugaucaggau gucccccggc uugacaaugg uccaguauau | 960 |
| gcugaugcgg gagcucagac cgcgcaccca cggucgcgcu ccaauguugg gaaugauggu | 1020 |
| cugcuggcug cgcuugguugc ucacgauuau cuucccgcug gccugcacgu acagguuuau | 1080 |
| cuguucgcgu uccgugcugg gauggugcac gcccauaug uacaguuuau caaagucguc | 1140 |
| acguuuggc auggucacau ucaacaucgg guaaguauug ccgcucuugu aaagccaauu | 1200 |
| caacuugcua aagaagcugu auugggucc ccuuuacag gcgcuggagc caccguuuug | 1260 |
| ggucacuccg guccaauuga aguucucauu ggugaacucc agggucccag agcucgcgau | 1320 |
| caggcuucgc aggcugguggu auucgggcac gucguauggg uagcaguugc ugaaugccuu | 1380 |

```
gcugcguucg augaacaagu cccacuuuuc guuuugaaag ccaucgcagu ggggaucacc    1440
cagcaaugaa ucgaucagcg ugcaguuggc cccguccaga augcggugcg gguuauugca    1500
aauuuugccc augcuaaaau ucugaaccag uucgguggcg uuggucaccu cgaucugauc    1560
gucgguaaua guuucacaa ggguugccguu cggcacggcg uggugcccaa ggcacagcgu    1620
ggccguguug uugccuuuac cagggagguc cugcccaaac accaggcaga agauguaacu    1680
cagggcgauc acggucuuca u                                              1701
```

<210> SEQ ID NO 17
<211> LENGTH: 1842
<212> TYPE: RNA
<213> ORGANISM: Artificial Sequence
<220> FEATURE:
<223> OTHER INFORMATION: combination of SEQ ID NOs:14, 1, 15, 13, and 7

<400> SEQUENCE: 17

```
aaguuuuuua uaaugaguuu agaaugauaa uuguugacug augcaggacu ggucuugaau      60
auuuaguaca gcuuucuggg ggccagcugg daccgcucga cacgauuuc cauuccgccg     120 auguugcugg gcacguaguu gaacugguug uccacguuga ugcucaucug cuggauggg     180 uuccaggugu gagaggcccg cagcuuggcc uugaacacca gcuugcccuu ccaccagaag    240
ucgcuguagg ucacgauccg gcucauguug gcgcuggcgu cagggucgua ucguuggcu    300 agguuggggg ccaccuucac aaacagcugg ccagggcagu guucuggca cacgaaaggg    360 gcguucacau gcagccgggg cuucaggucg gugucgaacu cuuugcccca gaucuguccg    420
uugggguaca cgggggcac guugucagg gcggucagag ggccguagga uugaagaua     480 uugguguagu ugaugccggu cuugccgccg augggaucug uggcagcag cacguugucg    540 ucggucacgg gcagguugaa guugauguuc ugaaccagu cgcccucggg guaucugccg    600
guguccuggu gggcgauaua ggugaaccgc ucgggugucu cgccgguggu gguguuuuc    660 uggccgugcu gucugccaaa ggcguaucug ggguugccgu cggcgcccug auucucaucg    720
gucugggcuc cgcccucuucc ggcggcaaua ggugucuuga aggggcccug ggucuggcc    780 ucgaagcugu aguagggggc gcuguagccc acuucggcag gccgcaugau uguggccucg    840
gugauguagu uggucuugcc caucugucuc acgccucucc gcuuguccug cugcacgccg    900
auauagccaa aguggugcc gcccucgccc ugaggcagac uguucaggaa uggggcagg    960 cccagggcuc uauuggucug ccaggugugg gucagccggc aggguuugca gucgaaaag    1020 aaugugccug uggcgaacuc gucgccgguu ucagcagau gcacgggcac gcuguucucg    1080
augguguaga acugcacguc gucggggucg gugccguggu agauguuggu agggggugccg    1140 cugguccccug uguggcuggg gaucaggguu cugucccacu ggaaguagua ccgccagggg    1200
guagggaugg uggcuuccua ggggguagaag cccagugucu cgcuccgcau ggcggcaggg    1260
gugaagggca ugguguuguu gcugucaga gccaccauca ggaggcggu cagguccguug    1320 uuguacaccu uggugggggg cuguguggcg cucucggaca cgguuuucag caccacguug    1380 aagauuccu gcucgaagga caccaggugc agcucgcuca uggugucac gaucagcugc    1440 cagucgccgg ggugaaccaa cacgccccag gcauuggcau ccaccaggga ccaggguguc    1500
acgaucuggg cguggguauc guccagggcc auguugccgu ucacggcggu cuuguccagg    1560
uuguucacga ccacccgccg guaguucucg cucucgggca guucaggug caccagcugu    1620 cugcuguugg cggugauuuc cacccagccg uuuuccagga acuugaacuc ggucugguug    1680
```

| | |
|---|---|
| uugaaggugc cggugcuaau ucccacuccg ccacuuccccc cuccgccgcc uccgccagau | 1740 |
| ccauugccgc ugccgguggc ucucucauuc cgcacagcag gcuguccgcc aucaggcugc | 1800 |
| acggcgccau cagacauggu gcugcuggac uaccugaguc cu | 1842 |

```
<210> SEQ ID NO 18
<211> LENGTH: 1842
<212> TYPE: RNA
<213> ORGANISM: Artificial Sequence
<220> FEATURE:
<223> OTHER INFORMATION: combination of SEQ ID NOs:1, 15, 13, 7, and 14

<400> SEQUENCE: 18
```

| | |
|---|---|
| uuuuuuauaa ugaguuuaga augauaauug uugacugaug caggacuggu cuugaauauu | 60 |
| uaguacagcu uucuggggc cagcuggac cgcucgaaca cgauuuccau uccgccgaug | 120 |
| uugcugggca cguaguugaa cugguugucc acguugaugc ucaucugcug gaugggguuc | 180 |
| caggugugag aggcccgcag cuuggccuug aaccagcu ugcccuucca ccagaagucg | 240 |
| cuguagguca cgauccggcu cauguuggcg cuggcgucag ggucguacuc guuggucagg | 300 |
| uugggggcca ccuucacaaa cagcuggcca gggcaguugu ucuggcacac gaaaggggcg | 360 |
| uucacaugca gccggggcuu caggucgug ucgaacucuu ugcccagau cuguccguug | 420 |
| ggguacacgg ggggcacguu guucagggcg gucagagggc cguaggucuu gaagauauug | 480 |
| guguaguuga ugccggucuu gccgccgaug ggaucugugg gcagcagcac guuugucgucg | 540 |
| gucacgggca gguugaaguu gauguucuga auccagucgc ccucgggua ucugccggug | 600 |
| uccuggugg cgauauaggu gaaccgcucg ggugucucgc cggugguggu gguuuucugg | 660 |
| ccgugcuguc ugccaaaggc guaucugggg uugccgucgg cgcccugauu ucaucggu c | 720 |
| ugggcuccgc cucuuccggc ggcaauaggu gcuugaagg ggcccugggu gcuggccucg | 780 |
| aagcuguagu aggggcgcu guagcccacu ucggcaggcc gcaugauugu ggccucggug | 840 |
| auguaguugg ucuugcccau cuguugucacg ccucuccgcu ugccugcug cacgccgaua | 900 |
| uagccaaagu uggugccgcc cucggccuga ggcagacugu ucaggaaugg gggcaggccc | 960 |
| agggcucuau uggucugcca ggugugggc agccggcagg guuugcaguc gaaaaagaau | 1020 |
| gugccugugg cgaacucguc gccgguucuc agcagaugca cgggcacgcu guucucgaug | 1080 |
| guguagaacu gcacgucguc gggugucggug ccguguaga uguuguagg ggugccgcug | 1140 |
| gugccugugu ggcugggau cagggguucug ucccacugga aguaguaccg ccaggggua | 1200 |
| gggauggug gcuuccaggg guagaagccc aguecugc uccgcauggc ggcaggggug | 1260 |
| aagggcaugg uguuguugcu guccagagcc accaucaggg aggcggucag gucguuguug | 1320 |
| uacaccuugg uggggggcug uguggcgcuc ucggacacgg uuucagcac cacguugaag | 1380 |
| auuccugcu cgaaggacac caggugcagc ucgcucaugg uguucacgau cagcugccag | 1440 |
| ucgccggggu ugaaccacac gccccaggca uuggcaucca ccaggacca gggugucacg | 1500 |
| aucugggcgu ggguaucguc cagggccaug uugccgguuca cggcggucuu guccagguug | 1560 |
| uucacgacca cccgccggua guucucgcuc ucgggcaugu ucaggugcac cagcugcug | 1620 |
| cuguggcgg ugauuccac ccagccguuu ccaggaacu ugaacucggu cugguuguug | 1680 |
| aaggugccgg ugcuaauucc cacuccgcca cuucccccuc cgccgccucc gccagaucca | 1740 |
| uugccgcugc cgguggcucu ucauuccgc acagcaggcu guccgccauc aggcugcacg | 1800 |
| gcgccaucag acauggugcu gcuggacuac cugaguccua ag | 1842 |

```
<210> SEQ ID NO 19
<211> LENGTH: 1788
<212> TYPE: RNA
<213> ORGANISM: Artificial Sequence
<220> FEATURE:
<223> OTHER INFORMATION: combination of SEQ ID NOs:14, 1, 16, 13, and 7

<400> SEQUENCE: 19 aguuuuuua uaaugaguuu agaaugauaa uuguugacug augcaggacu ggucuugaau      60
auucaaaugc agauguuaca gcgaauauug cccuuuugac aggcccacau gaugaaaccc     120
aaccaaacgg cgcacagcag gaagcagcuu auggcaaagc ugauccacag uaccaguccc     180
uuauagccac ucuucaguuc cacgcuuuug auuuggaagc gguuauuaac ugccucaucg     240
cgguacucgu uggucgua gguuccguuu cggaugcucu ccaugcagcu auugucgcac       300
uuguggaga ucuuaaaaca cccauuaccc augucuucgg cguucucucg gaguugcuuc      360
cgggucuucu cgaagaguuu auucaucucg cugucgguca ggucaauggu guguugguuu    420
uccaaggcga ccaggagcuc ggcauuguag cuccacaggu cgaucuuggu guccuccacg     480
uagcgcucga ggucuuggau gcggcccucc accucgcuga auucuuucuc uauuuggugg    540
aauuucucgu ucgucuuuuc aaucacgcgg uuaagcuugc cguugaucug uugauggcu    600
gcuugcgugg acuucagauc cgcagcuugg ccgauuccuu cagaguucug auggcggaag    660
ccguaccagc cguuaaccau ucccucccag ccauucucaa ugaacccugc gauugcgcca    720
aaaugcccc gugucugucg cucggggaug uugcgcaugc cgguggccag cuucagggug    780
uucugccuuga uguacuuggg gcacgcgccg uaggugaucu uauucacguu cuggaaaggc   840
uugucguugg ggaugcugcc auuggggug augcaucgc uauugcaggu gucgauggg       900
gcgucgcucc ucaucacacu gcuuuugccg gucugcaucu ugaaguagcc gcuggggcg     960
auaagauugc cauuagaguu gaugaucagg augucucccg gcuugacaau ggaccaguau   1020
augcugaugc gggagcucag accgcgcacc cacggucggc ugccaauguu gggaaugaug   1080
gucugcuggc ugcgcuuggu gcacgauu aucuuccgc uggccugcac guacagguuu     1140
aucuguucgc gguccgugcu ggaugguggc acgcccaua uguacaguuu aucaaagucg   1200
ucacuguugg gcaugguaca auucaacauc ggguaaguau ugccgcucuu guaaagccaa   1260
uucaacuugc uaaagaagcu guuauuggu ccccuuuuac aggcgcugga gccaccguuu    1320
uggguacauc cgguccaauu gaaguucuca uuggugaacu ccaggucccc agagcucgcg   1380
aucaggcuuc gcaggcuggu guauucgggc acgucguaug gguagcaguu gcugaaugcc   1440
uugcugcguu cgaugaacaa gucccacuuu ucguuugaa agccaucgca guggggauca     1500
cccagcaaug aaucgaucag cgugcaguug gccccgucca gaaugcggug cgguuauug     1560
caaauuuugc ccaugcuaaa auucugaacc aguccggugg cguuggucac cucgaucuga   1620
ucgucgguaa uaguuucac aagggugccg uucggcacgg cguggugccc aaggcacagc    1680
guggccgugu uguugccuuu accagggagg uccugcccaa acaccaggca gaagauguaa   1740
cucagggcga ucacggucuu caugguggug cuggacuacc ugaguccu                 1788
```

```
<210> SEQ ID NO 20
<211> LENGTH: 1788
<212> TYPE: RNA
<213> ORGANISM: Artificial Sequence
<220> FEATURE:
<223> OTHER INFORMATION: combination of SEQ ID NOs:1, 16, 13, 7, and 14

<400> SEQUENCE: 20
```

```
uuuuuauaa ugaguuuaga augauaauug uugacugaug caggacuggu cuugaauauu      60
caaaugcaga uguuacagcg aauauugccc uuuugacagg cccacaugau gaaacccaac     120
caaacggcgc acagcaggaa gcagcuuaug gcaaagcuga uccacaguau ccaguccuua    180
uagccacucu ucaguccac gcuuuugauu uggaagcggu uauuaacugc cucaucgcgg     240
uacucguugu ggucguaggu uccguuucgg augcucucca ugcagcuauu gucgcacuug    300
ugguagaucu uaaaacaccc auuacccaug ucuucggcgu ucucucggag uugcuuccgg    360
gucuucucga agaguuuauu caucucgcug ucggucaggu caauggugug uugguuuucc    420
aaggcgacca ggagcucggc auguagcuc acaggucga ucuuggugc ucccacguag     480 cgcucgaggu cuuggaugcg gcccuccacc ucgcugaauu cuuucucuau uugguggaau    540
uucucguucg ucuuuucaau cacgcgguua agcuugccgu ugaucgguu gauggcugcu    600 ugcguggacu ucagauccgc agcuuggccg auuccuucag aguucugaug gcggaagccg    660
uaccagccgu uaaccauucc cucccagcca uucaauga acccgcgau ugcgccaaaa      720 augccccgug ucugucgcuc ggggauguug cgcaugccgg uggccagcuu cagggguguc    780
ugcuugaugu acuuggggca cgcgccguag gugaucuuau ucacguucug gaaaggcuug    840
ucguggggga ugcugccauu ggggugaug cauucgcuau ugcaggugc gauggggcg      900 ucgcuccuca ucacacugcu uuugccgguc ugcaucuuga aguagccgcg uggggcgaua    960
agauugccau uagaguugau gaucaggaug ucucccggcu ugacaauggu ccaguauaug   1020
cugaugcggg agcucagacc gcgcacccac ggucggcugc caauguuggg aaugauggc    1080 ugcuggcugc gcuggugcu cacgauuauc uucccgcugg ccugcacgua cagguuuauc    1140
uguucgcggu ccgugcuggg auggugcacg ccccauaugu acaguuuauc aaagucguca   1200 cuguggca uggucacauu caacaucggg uaaguauugc cgcucuugua aagccauuc     1260 aacuugcuaa agaagcuguu auugggucc cuuuuacagg cgcuggagcc accguuuugg   1320
gucacuccgg uccaauugaa guucuuauug ugaacuccca ggucccaga gcucgcgauc    1380 aggcuucgca ggcuggugua uucgggcacg ucguauggu agcaguugcu gaaugccuug    1440
cugcguucga ugaacaaguc ccacuuuucg uuugaaagc caucgcagug gggaucaccc    1500
agcaaugaau cgaucagcgu gcaguuggcc ccguccagaa ugcggucgg guuauugcaa    1560 auuugcccca ugcuaaaauu cugaaccagu ucgguggcgu uggucacuuc gaucugaucg   1620
ucgguaauag uuuucacaag ggugccguuc ggcacggcgu ggugcccaag gcacagcgug    1680
gccguugugu ugccuuuacc agggaggucc ugcccaaaca ccaggcagaa gauguaacuc    1740
agggcgauca cggucuucau ggugcugcug gacuaccuga guccuaag                1788
```

<210> SEQ ID NO 21
<211> LENGTH: 1845
<212> TYPE: RNA
<213> ORGANISM: Artificial Sequence
<220> FEATURE:
<223> OTHER INFORMATION: ombination of SEQ ID NOs:14, 1, 15, 13, 7, and 14

<400> SEQUENCE: 21

```
aaguuuuua uaaugaguuu agaaugauaa uuguugacug augcaggacu ggucuugaau     60
auuuaguaca gcuuucuggg ggccagcugg gaccgcucga acacgauuuc cauuccgccg    120
auguugcugg gcacguaguu gaacggguug uccacguuga ugcucaucug cuggauggg    180 uuccaggugu gagaggcccg cagcuuggcc uugaacacca gcuugcccuu ccaccagaag    240
```

-continued

| | |
|---|---|
| ucgcuguagg ucacgauccg gcucauguug gcgcuggcgu cagggucgua cucguugguc | 300 |
| agguuggggg ccaccuucac aaacagcugg ccagggcagu uguucuggca cacgaaaggg | 360 |
| gcguucacau gcagccgggg cuucaggucg gugucgaacu cuuugucccca gaucuguccg | 420 |
| uuggguaca cgggggggcac guuguucagg gcggucagag ggccguaggu guugaagaua | 480 |
| uugguguagu ugaugccggu cuugccgccg augggaucug uggcagcag cacguugucg | 540 |
| ucggucacgg gcagguugaa guugauguuc ugaauccagu cgcccucggg guaucgccg | 600 |
| guguccuggu gggcgauaua ggugaaccgc ucgggugucu cgccgguggu ggugguuuuc | 660 |
| uggccgugcu gucugccaaa ggcguaucug ggguugccgu cggcgcccug auucucaucg | 720 |
| gucugggcuc cgccucuucc ggcggcaaua ggugucuuga aggggcccug ggugcuggcc | 780 |
| ucgaagcugu aguagggggc gcuguagccc acuucggcag gccgcaugau guggccucg | 840 |
| gugauguagu uggucuugcc caucugaguc acgccucucc gcuugccug cugcacgccg | 900 |
| auauagccaa aguuggugcc gcccucggcc ugaggcagac guucaggaa uggggggcagg | 960 |
| cccagggcuc uauuggucug ccaggugugg gucagccggc agggguugca gucgaaaaag | 1020 |
| aaugugccug uggcgaacuc gucgccgguu ucagcagau gcacgggcac gcuguucucg | 1080 |
| auguguagaa acugcacguc gucggggucg gugccgguga agauguuggu aggggugccg | 1140 |
| cuggugccug uguggcuggg gaucaggguu cugucccacu ggaaguagua ccgccagggg | 1200 |
| guagggaugg uggggcuucca ggggguagaag cccagugucu cgcuccgcau ggcggcaggg | 1260 |
| gugaagggca uggguguuguu gcuguccaga gccaccauca gggaggcggu caggucguug | 1320 |
| uuguacaccu uguggggggg cuguguggcg cucucgacaa cgguuuucag caccacguug | 1380 |
| aagauuuccu gcucgaagga caccaggugc agcucgcuca ugguguucac gaucagcugc | 1440 |
| cagucgccgg gguugaacca cacgcccag gcauuggcau ccaccaggga ccaggguguc | 1500 |
| acgaucuggg cgugg guauc guccagggcc auguugccgu ucacggcggu cuuguccagg | 1560 |
| uuguucacga ccacccgccg guaguucucg cucucgggca guucaggug caccagcucg | 1620 |
| cugcuguugg cggugauuuc cacccagccg uuuccagga acuugaacuc ggucgguug | 1680 |
| uugaaggugc cggugcuaau ucccacuccg ccacuucccc cuccgccgcc uccgccagau | 1740 |
| ccauugccgc ugccgguggc ucucucauuc cgcacagcag gcuguccgcc aucaggcugc | 1800 |
| acggcgccau cagacauggu gcugcuggac uaccugaguc cuaag | 1845 |

<210> SEQ ID NO 22
<211> LENGTH: 1791
<212> TYPE: RNA
<213> ORGANISM: Artificial Sequence
<220> FEATURE:
<223> OTHER INFORMATION: combination of SEQ ID NOs:14, 1, 16, 13, 7, and 14

<400> SEQUENCE: 22

| | |
|---|---|
| aaguuuuua uaaugaguuu agaaugauaa uuguugacug augcaggacu ggucuugaau | 60 |
| auucaaaugc agauguuaca gcgaauauug cccuuuugac aggcccacau gaugaaaccc | 120 |
| aaccaaacgg cgcacagcag gaagcagcuu auggcaaagc ugauccacag uauccaguccc | 180 |
| uuauagccac ucuucaguuc cacgcuuuug auuuggaagc gguuauuaac ugccucaucg | 240 |
| cgguacucgu uguggucgua gguuccguuu cggaugcucu ccaugcagcu auugucgcac | 300 |
| uugguguaga ucuaaaaaca cccauuaccc augucuucgg cguucucucg gaguugcuuc | 360 |
| cgggucuucu cgaagaguuu auucaucucg cugucgguca ggucaauggu guguugguuu | 420 |

| | |
|---|---|
| uccaaggcga ccaggagcuc ggcauuguag cuccacaggu cgaucuuggu guccuccacg | 480 |
| uagcgcucga ggucuuggau gcggcccucc accucgcuga auucuuucuc uauuuggugg | 540 |
| aauuucucgu ucgucuuuuc aaucacgcgg uuaagcuugc cguugaucug guugauggcu | 600 |
| gcuugcgugg acuucagauc cgcagcuugg ccgauuccuu cagaguucug auggcggaag | 660 |
| ccguaccagc cguuaaccau ucccucccag ccauucucaa ugaacccugc gauugcgcca | 720 |
| aaaaugcccc cgucucgucg cucggggaug ugcgcaugc cgguggccag cuucagggug | 780 |
| uucugcuuga uguacuuggg gcacgcgccg uaggugaucu uauucacguu cuggaaaggc | 840 |
| uugucguugg ggaugcugcc auggggguug augcauucgc uauugcaggu ucgaugggg | 900 |
| gcgucgcucc ucaucacacu gcuuuugccg gucugcaucu ugaaguagcc gcguggggcg | 960 |
| auaagauugc cauuagaguu gaugaucagg augucucccg gcuugacaau gguccaguau | 1020 |
| augcugaugc gggagcucag accgcgcacc cacggucggu gccaauguu gggaaugaug | 1080 |
| gucugcuggc ugcgcuuggu gcucacgauu aucuucccgc uggccugcac guacagguuu | 1140 |
| aucuguucgc gguccgugcu ggaugggugc acgcccauia uguacaguuu ucaaagucg | 1200 |
| ucacuguugg gcaugucac auucaacauc ggguaaguau ugccgcucuu guaaagccaa | 1260 |
| uucaacuugc uaaagaagcu guuauugggu ccccuuuuac aggcgcugga ccaccguuu | 1320 |
| ugggucacuc cggccaauu gaaguucuca uggugaacu ccaggguccc agagcucgcg | 1380 |
| aucaggcuuc gcaggcuggu guauuccggc acgucguaug gguagcaguu gcugaaugcc | 1440 |
| uugcugcguu cgaugaacaa guccacuuu cguuuugaa agccaucgca gugggggauca | 1500 |
| cccagcaaug aaucgaucag cgugcaguug gccccgucca gaaugcggug cggguuauug | 1560 |
| caaauuuugc ccaugcuaaa auucugaacc aguucggugg cguuggucac cucgaucuga | 1620 |
| ucgucgguaa uaguuucac aagggugccg uucggcacgg cguggugccc aaggcacagc | 1680 |
| guggccgugu uguugccuuu accagggagg uccugcccaa acaccaggca gaagauguaa | 1740 |
| cucaggggcga ucacgucuu caugugcug cuggacuacc ugaguccuaa g | 1791 |

<210> SEQ ID NO 23
<211> LENGTH: 12291
<212> TYPE: RNA
<213> ORGANISM: canine distemper virus

<400> SEQUENCE: 23

| | |
|---|---|
| accagacaaa gcugggúaug auaacuuauu aauaaccguu guuuuuuuc guauaaccaa | 60 |
| guuugauagc aaugaauagu aggggggcuag gagccagacu aaccguuag ugauuucuaa | 120 |
| ucagugcacu auaaccuaac aauuugaacc acuccuuuau ucucuuuuguc ucaagcugaa | 180 |
| agagccaauu cuuuuugggg auugucguua ggaugagaga ccugucagau ccggacagau | 240 |
| uauccauaaa uaaguuacga ugcaagucga aauuaugug guuggcuuuc agguucgga | 300 |
| caauccuggu aauuucguau aagcucccg aguaaagcaa aauauagcca caguacuucu | 360 |
| uugcaaugau agauacgagc ucccuuuccu gacuugcgau uaacacaggg uaugcaugga | 420 |
| acauuccaug ugaagauugg ugguuauccu ugaaccuugc gaguucccgg uaaaggaucg | 480 |
| ugauagaucc uuucagcccu uccucgccug acgaaauauc augugaagc agguucuuac | 540 |
| auaccuuaag accauuaauu guaagcccac aauugauuaa uaccuucuca auacuuguua | 600 |
| aacccuggag gugaggauug aaggauucag caugaaaugg aggucgugc aaagacugca | 660 |
| cacaugcugc cugcuuugau gaaaggaugu gcccuaccaa cccagguaa guucgaauac | 720 |
| cgacucgcaa aaucuguugu uuaauccccu ccggauugac uagucucccu gcucuaagac | 780 |

```
caguaaaaac aagguaggcc ucuguugaca caaaauugcu guaucuuggg uaaacuauga      840
aacuucgaag aaaauguggg agugcauaua aaauaaaucc uugaacccag ucgccacuag      900
cuggcaugau cuuaauuacu aacacugacc cuaccuuccc uaauaucaaa gucauugaua      960
auauagcaga caauuccucc aacuuuucga uuaugucuuu guccgguagu gacucuauau     1020
ccgagugaau caacccaaga cugcuagcag agaucuggcu caguauguac uuguaacaau     1080
caacacuccc aacccaaguu acuucugguc ugccauugaa aagcacaguc gccaauuuau     1140
cgagccuaa uugauguucc accagacuga ccucagaagg guaaggugaa aucucucguu      1200
guccaguucu ggacucuacu gacacaccac uguuauaaua acaucuugac aaucuuaaua     1260
gcucuuuaua uacgucaac auugcaccug aaccuucucc uaggaauaau ccguguucuu      1320
cagacguaaa uucguucuua aucacagaag cuauuucaac ugccuuguaa caugcaguag     1380
aguugauccc aaucuucug aaugagugaa ccucauaguu ccggacuccu aaccuguaa       1440
ugggaaguu augugccuu guugacagcu gacucagaag uuuggccagg ucaucuuucg       1500
gugggucaaa uucugacuuu aauucugagg ccuuagaggu agaauuauuu cuuagaggac     1560
gccuuucuaa gcauccaaca gcaucaguga ugaauccggg auccacucuc agucuuaucu     1620
gcuugauuga gccucuucua agauauguca gggaacauga auauugaucu auuaagauag     1680
guuugucauu ccaugucaga ccaacauggg auucuagggc uuuugacuuu aaguaccccg     1740
auaacacagc acauuucugu guuggugca acccacgaau cugggacaa ucacgagggu      1800
uacaauaaag gucagauaag augcauaggu gccuggcuug uauguugca aaucuuucag     1860
guaugacauc cucgucacuu ucgcauaaaa ugaaugagaa aucaucuaau ucaucauuua     1920
acagaagguc uagguaaauc augugacagu uauagaucag guugcauaca guuauaugua     1980
gguuuuggga gucaagagag ggccaugaa uagguucaau caucccacug ucccaaaacc     2040
gucuauauac uuuaggaugg cucaaugcau ugguuaaaau uuugaagacu ccuuuacuca     2100
uucuacucag gaaagagaac aacaacucac ccauuuggua cuuuccagaa ggucggugau     2160
aaugaauuuc aaagccccag uugauugcag cacauuggcc uagauauaca guaaauaauc     2220
uaggcucaac uagaagaaac ucagugauaa aacuauugau aucaucaucg ccaauuaacg     2280
cagagacuuc auuuaggugg uccuuuucaa acuuuguaau caucaaacc auagacauag      2340
caguagacuu agcuagcaca ugauaaagcu gcccuguugu ccaugugaca aacucuacaa     2400
ugucuuucu gugacucugg uuauaaaguc ugacugcauc uuucucaaua auaggguuac      2460
ugucauaaau caaaggauuu guacagauau uucuugguau gacgcauuuu cugagcccug     2520
ggacucuugg auggucgcuc augggauuau cgcaacaauc uguuucaaca guaaaugua     2580
auacgguauu agagucgccg gugguugaag acaaucuaaa uaagcgcuca aggauccccca    2640
ggcccaggag cauaccuugu ugauaaauaa auuugugucu cacuuucuug ucaucuauaa     2700
uaaaagaaag auuaucauuc gagauaguug cauaacgugc cacucugaug agagaggucc     2760
cugaguauuu gacuugagua cucuugucuc uuagucggug agcuagauua guagaagugg     2820
aaauuggggu aaucauccgu aauuccucaa gugagauguu cgcucucugu uuugccaagg     2880
uccaagccuc uugccaagau ucgucaucau caccauaggc ccaugaguac acaguugcua     2940
uucucacugc ugauuucaga gaccuacuag gagauuugac gaaugcuagu uucaugucug     3000
uucuuucuuc uguguggac ccuauguaug gcacccucag ugcaugaguguu cccucuguaa   3060
uacuauccaa uuggcaauuc gcugguacaa aaaaccaacc auaguuauga gagccugaug     3120
```

-continued

| | | | | | |
|---|---|---|---|---|---|
| cacaaagcaa | acaggauuca | ugucuucuga | ucauauaacc | cuucauugau | ucaaggauau | 3180 |
| ccgggacuuc | uagaccauaa | auaggacgac | ccuucgccag | cuuggcccac | augugguucc | 3240 |
| uuaaugcucu | cgcuagcugg | acggaacaug | agucuugauc | gaugagcgga | ucaugcsccu | 3300 |
| ucccugacaa | cagucugaua | ccugcccuaa | auuguucaua | aucauaaguu | gacaaacggg | 3360 |
| uuauuauucu | aggguuaga | ccuccucuuu | ucaugcuugc | ucguaucaac | cccuuugugg | 3420 |
| ugucuagcau | uccggugauu | gccucucuug | caccugugau | cguuuaucu | agaauuucau | 3480 |
| gugcagcccu | ugggauaaua | auuuccuau | ccauuaagaa | agcugcuaaa | gcuucauccu | 3540 |
| cauccugacu | uucaucaugg | aacaauccuc | ucagcaucgg | auuggacug | uugauaagga | 3600 |
| caugccuggc | ugugauauuu | uuaaggaguc | ggguuaugcu | cuggacacag | ggcagauugg | 3660 |
| cagaauaagg | gucacuugcc | caaucuaaau | aagaagaguc | accugggguau | uggggucauga | 3720 |
| ccugauguag | aaucuccacu | ccaagaaggc | cugaucggau | cauucguuug | aggucagcaa | 3780 |
| uagaagaugu | cacgggaucc | ccgauauucc | ugacaaagag | ccuacucaua | uugagguaau | 3840 |
| uaagaccgcc | aauggggucg | gggagaauug | ccaucuggu | caagagacag | ugaucuugua | 3900 |
| cgaggguuc | uaucacaucc | cgugucauag | cugaauugau | agugaauccu | aaugaaauua | 3960 |
| auacuuguug | aaugauuuuu | aaaauguuca | gugcguaggc | uaaauaucgg | ucaaacccuu | 4020 |
| ucucaauggc | uuucgcuaau | guuguugaaa | uguugcugca | cgcggcucgg | gucucauccu | 4080 |
| cuauuguuuc | ugaccaaaau | acacaccuag | cuauacucuu | cagggauugu | gagauuaaca | 4140 |
| uccgcucaua | auagauccccu | uuugaguaua | caaaaaagug | ggaagagauu | auuguuucau | 4200 |
| uugcuuucaa | augauguccg | acaucaugua | accucugucu | caaggcuaua | aaguauucg | 4260 |
| cggucacucg | acuggcuuca | gauuucuuca | aggcauagga | ccaggugcuu | gguacucuuu | 4320 |
| uagugacagc | aauaguuugg | uuaucaccuu | ggacaaguga | ugcaauucug | acaccgcucu | 4380 |
| caugugccgc | caaguacaaa | uaagguaugg | uguuaauagu | ccaacaacuuc | ugacaauaac | 4440 |
| ccuccacccc | ccccauuggg | uauuugauga | auauuugaga | guuaggggcu | guauucaagu | 4500 |
| ccacaugacg | aucgagaucu | ggagggcagu | gggggucacu | uacguauaag | aucgacuguu | 4560 |
| ccaaucuucu | cuguaaccau | uggaaaaaug | agggagacc | uagauuuca | uuuaaucucu | 4620 |
| gagcaaaaau | acugaugguc | ucauaacgcc | aaucagaca | guacuuuuug | agauccguag | 4680 |
| uuauaaaugc | acuuacaguu | ucauagaucu | cuaugcauu | gucucucuu | cuacuggugc | 4740 |
| aaaaauuugg | guuuggggucu | auauaucuac | uacuugggga | agagacggag | ugaagugcuc | 4800 |
| cucgauaagg | ugcagguuuc | aggggauuuac | ucugguuagu | gaggccacga | uggaagucuu | 4860 |
| ucuugucuuu | cggaaccccg | gacacagcca | gagugugcaa | ugcuuuagug | agaucguguu | 4920 |
| cauccuuugc | cauuccauug | uccuugaagu | acuucccaau | uccauuagau | aucaaguucu | 4980 |
| cugcuaugac | cugacaggcu | cgcauuuugu | aggucauuuu | agcgaauagc | cucccuaccu | 5040 |
| cuuuaaucuc | uuucucuuug | agacuguaug | auagguugaa | aucaggaucu | ucuagauauu | 5100 |
| gaccugagau | aacguacaua | aucauguuau | aagggucaaa | cugagaguccc | ucuagaaaca | 5160 |
| cauuaacaag | ucuccgagac | ucaguggagc | gaggugaguu | guaccugagg | aauucuuuug | 5220 |
| gguacacuga | gucccacucu | uuucuuaggg | cugccaaagc | cuuaucuuuc | agguacaugg | 5280 |
| ucaaaucacu | gucuaggcua | agaggcauaa | agcauuuaaa | ucgaauuccu | gcaaaggauu | 5340 |
| uccaguuuuc | uauacauuga | cuauaggugu | uucccucccc | ugaggcauga | gcauuucuga | 5400 |
| ugaugggaga | ugcaugaaca | ggaagaucca | ucggaggcca | aguucccca | ugucuauccc | 5460 |
| gauaaccguu | aaugauuauc | ccacagaaua | uagcauguuc | cuucaucaua | gucucauaag | 5520 |

```
agacaacuuu ggguugauuc auguguuucc guacguuuuc ugcugcuguu auugcuucua    5580
accuuggguu accgaaacuu cuaaagaagg aaaagauuuc uccuguuaua uguauauccu    5640
cugugaugaa aacgaagucu agagcuuggg uuaaaguuug aacgucucu ucaguauaga     5700 agccauuguc cuguaaaauc uccugaauuu cagcaaagca gugacucaga aaagcacccc    5760
ugagagagaa ggugaugucu uuuaacugca aguaagccaa ugagagaggc uccaguagag    5820
ccaccaauug auagguugaa uucccagau ccgggaaaaa uccgucaauu agacccaga      5880 gauaccugau ccugacaugc aaaguugagu aacguugauc aauugccaua gcaguaucag    5940
ucauuagccu cccuucuauu acaucacagu acaucaagac cauucaaau guuagguaau    6000 aaacauugug acggugaga ucaauaauac auacaaggu ccuagacacu agcacauuaa     6060
augauucacc uuuuacaaag acaggauucu gccuccgcuu gcgacaguug ugaguagagg    6120
auuuaaucac ugaucucauu ucuguuuaa uuguaaacca uagaaggaaa gguucgaacc     6180
acugugagcu uugcauaauu augccugcuu caucaauuuu ggcccaaua gucuugcca     6240 gugcgccccc uaaaccaaua uuaagauuaa uacguuuaa gcauuuuug accccgucug    6300 uuauuuugcu auagaugcua uuccucuuu ugaauauauu ucucagccuc agagagguga    6360
cucgauccug ugcaugaaau agaaguuugu ugcaauuugg guauaucaca ugguugguguu   6420 ugggauaaga uaacaaggc ugauuaauaa ugcucccgau uucgaugcag uuaaugauca    6480
ucgguuugaa gaacccuucu gaaauucucu cuuugauauu acgcacuaau guuguaucaa    6540
ggaguugaua gcuaugucua auucgugcgu auucuaaaau agcuacagc uuauugguua    6600 caauugggcu aucuagaugg accucagggu auagaaucug guucacugac acagaguccca   6660 uggcuaaaag gauccuggau ccuuaguuu uuauaaugc uggagauggu uuaauucaau     6720
caucuguaag ggauuuuuca ccauacucau caugccuaag uccaauugag augцuguauca   6780 uuauacuguc agggauuuga acgguuacau gagaaucuua uacgacuaa auucucaaca    6840 cugguuguag aguuggcgau guuagccucg uaucuguaaa auuggugaca ccacaaauua    6900
ucaucccaca caaaacauuc aauccuuagg aaaucagguc uacccuuggu aguuagucua    6960
aaugagugcg uauaagaaau cguccggauu ggcauaaaa cauaauaaac aaucgcauga    7020
ucauuucgug auauaucaua cguugcuaug acauaucaa aacucugugu aggcaacacc    7080
acuacauugg acucgaugag gacaucucua ucuauaauuu gagauguuug aauagguaaa    7140
uaacaauuuc cacaugauuc ccgggcgca aauguuaaua cuuggggguau cacaguga     7200 uggucuccuc uacuugcuuu guuuaucaau ccaaggauug uuccguuuu aggaggaaug    7260 guaagccauc cggaguucaa aagugggcuu ucauaauaau ccauaccauc uccauucagu    7320
auaaccggac cguaugugaa cgaugugua aguugaaggu caaacuugc aucuagaggu     7380 aaugucaacc gcccauaaga uggcaacugu ccuccuccga aggguucca ugacguuugg    7440 uugcacaugg gguagguuu ucuuugacaa gcugacucca gccaaccuuu uguucuucu    7500 uguuucucag aggccagggc aggcaccauc cagguugcaa uugaaucuuu uauaaaacca    7560
cgguggguuu uuauauguau uuuccccauu gauggguag cgacagguau cacuccuca     7620 auaugaucca uaguuguugc cccaaauauc cccagucuca cuacuagaaau accaucuugu    7680 gaaccccugc ugucaugugua uaauaauaca gugcucucuu cuacacacaa ggaagccagu    7740
gucaacucac ccacugcuau ggacauaacc uuggcuuugg aauucccggg gaggaccaua    7800
uaguggguug uuuggaguaa uggcauguca uucagccacc uuuuaugaa cccuauuuca     7860
```

```
aagacucgaa ucucuugagu gucgaacucc cguucuauau caucaggcac uagcaaguaa   7920
guuuugccau acacgccguc ugagguagcg gucagcauau ugauuaucuc ugagguucuu   7980
gagaucaaag acauggauaa cgagacugau aggggggaaaa cuuugccuac ugaaguagua   8040
gcuccacugc aucuguaugg ugggaauaug ucacuccugc ccccagagag ggcugauaaa   8100
aggaugggau uugcugccga ugcaauagau uuucugaucc caauugucuc acaguaauuu   8160
guaaaauuca ccuugaccuu acuaggcggg uuaaugcacc aguggagauc gcggaaaucg   8220
aauucucugu ucggauugaa gaaauuuguc uuugaagga uaaauuguuu gaucucguuu    8280
agcuuuugug gcaaccguaa cccaaucuca uccccaauaa ucuugaagag cggugucaag   8340
acaucuauga cuugaugaug uacggccucu gauuucucca uaccucuuuu cagcaaucug   8400
cuaaauucca uauugcuagu ugauacuugg ugaaaucgaa uccagaugau agcaagcagg   8460
gccaggauuc caaccaauag gaugagaagg acaaacaaca aauaaggugg ucuccugccc   8520
ccaugcucuu cugucacugg ggacagcuug gaugaauugg cucuugcauu guccuuguag   8580 aaggcacccca ccuugucuug guaggagagc auugcuggac uaccugagcc cuaaguuuuc   8640
uuuaauuacg auaaucaugg ucagucuuuu ccaaguuuua uugcaguuga gugacucuuu   8700
aagaaaauug ggcgggguua auagauauca aaucuggcaa ucaagcgaga uauaugacca   8760
gaauacuuca gagugaucuc acauaggauu ucgaaguucc gguuagauca gguuuaaaug   8820
ccggaucgac cuuaguauuc cgcuugagug ucguuggua cgucuuuua caacaguaaa    8880 ucagcaacag caaagccagg gcuguaccac uuaauauagg aacgcugagg agacugccaa   8940
aauuaaagga agagcgccua acugucucaa ggaucgguu agaggagucu aucaguaccu    9000
uagcaucauc caguuucuua agggcguucc cuaaauuugu accuacaucu aaccucucaa   9060
gugauauagc aggggccuaag gcaacuuugc uuucauauac cauaucaggg uauugccugc   9120
cuccaacuug gauaguuaca ccaucuauuu caaccagugg gcagguaucg gaggcaauga   9180
augucagcaa cuuaucagga cucugauuaa uaauugugcu ugugcuauaa cacuuacaua   9240
guauagacgc acaauuugcg acgauguuac cuuuugacag aauaaauuug uugcccauag   9300
ucccagauac caagguccgg gcacaagaug aagugucgcc ccuaauacau uguuguaaga   9360
gugggcucau gggguacagg gaguucuggc uacaaauggc ugacucugag acgaauacac   9420
aggaugacuc aucaaaauua gauauuaagu aaccauuagu ugcaauauac cucgggacag   9480 uggguguacca cucuugugau ccuaguugu aagaaacugc uuccagucug uggacuauaa    9540 ccccccuugac uucugauaaa guuggguaug agauacuuag gaugaugaau ucccgggaa    9600 uaucaacaug aguuauuuuu guuuuuaucc cccgacucuc caagauugca aucauaucac   9660
cuccagagua ucccaacuuc ucaaguaucu uaugaauuuc uccuccaaga gcauaacuca   9720
gugcuugaau ugauaucucg gcugaaauag ggucacguaa acucgggcca aauauugaca   9780
auaacucagu auaauaccua agcaguuuua acccuaaucu cugcccaacu aauucacaug   9840
acauauguug cauagcaggg acgaguucgu uguuaacgua auccggacu cccugaacgg    9900 caaugacggu uucuugggua gccucccuaa uuucuucaau agcuuuguua gacuguucaa   9960
ggcugguucu aagagauugg auugcuugag cauugagguu ggauugaugu aaagcuauuc    10020
cugcagugau uugcugagcu guagccacuc cuaaagcugc accugcaagu accacuccug   10080
caaaacgccu uugucuccua gcugacccua augacugcaa gggcuucaca uucuugguca   10140 uuagagcag agcuugguug auugguucga ggacugaauu caauaauuuc ucauacucac    10200
cuaauucugc uuugguacaa uuaucuauaa gugaaacauu aggcaucagu uuuaugacca   10260
```

| | | | | | |
|---|---|---|---|---|---|
| aguacuggug | acugggccua | gccaugaucu | uauaauggac | acuaucaguc | ccaauaaucc | 10320
| caauaguuga | caaauuauuc | caauguaucu | gagccuugga | acaaagaaag | agacuggcua | 10380
| uuccgaggca | ccacaggacu | aaccaggagc | acugagagcc | ugaguugauu | gcauugggu | 10440
| gccgccuuuc | gaucgggau | cucgcuccuu | uggagacacu | cucuggcaug | ugcuggauaa | 10500
| uagccucgug | guuccguga | acgagaugu | ucccaaucu | guagcgguu | gcuugcgag | 10560
| accugguccu | guucauggug | uaggagacgg | gucuguccaa | uguucgagga | ucauaguucc | 10620
| uggaucgcug | agcugacguu | augcuguguc | gugcucggga | gguccugguc | ucgucgggguc | 10680
| cggugcuggg | uugugggggg | cgguuuguu | gguauaugu | gugggggu | gagcuuuugg | 10740
| ggauuccuu | gugcaugggg | cuuggcuguu | ugugggggu | ccugccuggc | ucgggcugg | 10800
| uggacuggu | uggccuguug | gcuugcuacg | uccuggaccc | uaaguuuga | uuaauuauua | 10860
| augagcugug | auagaaagau | ggacagucau | cacuccguga | aacaagacua | cuagugaugg | 10920
| cuugagauca | ggcaagugcg | ugggaguaua | acuguuaaag | ugagauuccu | agaagcgaag | 10980
| cucaaaaccc | caggcaucca | uucauuucuu | gguccgauaa | ugaucaaccc | aaucuuaagc | 11040
| aagaacuguu | uugauucagc | uauuucuaua | uugaggcguc | acuggaauug | ugggcacgga | 11100
| ugggcagucu | agaaaccuau | aggccacgcu | caaaaugcag | gagcaacauc | uagacagucg | 11160
| auauuuauac | ccucaauccu | cgcuugcggg | gaucaaggga | ucuuggcaa | ugcuacuaag | 11220
| gcguuugagu | uuaguucau | gaacuaauga | uuuagagaaa | uuugaaaaga | cccugaucau | 11280
| cgcugacgau | aacaucauua | uaaacucuga | aacuuugugg | gacugauggu | ugcaagacug | 11340
| cuuggauccu | uacuauuuug | cacucuaauc | uccauagaga | ucgauucaaa | ucuucauuga | 11400
| ucuccaugag | cggguaacac | aggauuuucu | ugaaaccuag | cugggcauuc | aaggccuugc | 11460
| ucaucuuacc | aguacaucgu | augugaagac | uuguccucc | uacccucuu | agagcaaaca | 11520
| cuaaucccau | cuuuucaauu | uucaguuuac | aauaaucagc | agaguaagcu | ugguuuuucu | 11580
| uacgccugaa | auugccgaua | cggaccauga | auguuacuug | ugaucuuug | aacaugcuca | 11640
| aauuaccucg | gcuugaacag | acaucucccu | caacuugaau | ggugacuaaa | auguaaaug | 11700
| cuaaagcauu | ccuggagcgg | aauucaaaca | ucccgcgggg | aauucuguaa | cuuccaucgu | 11760
| cugauagucg | agugaugcuc | auauauacca | cccugaaucu | uugugcuaug | ucuaauggua | 11820
| uuagauugac | ugcguuacag | acuugauug | cacugaacac | acuccacuc | guaaggaccu | 11880
| uuuccacgg | aguuaagaug | ugcaauggg | uguuauaua | aaauaccagu | uguuccuga | 11940
| caccugcagu | ucgccuugcc | acaauauca | acagggggc | uucuuucaau | aaccuccag | 12000
| gucuggcugu | aguacgccca | acucccaaag | gcagcaaucc | aaauguucuu | ccaauugggg | 12060
| guccgaggcc | aucauugucu | ucuauuauac | ccaguagaaa | aauauacaug | aagcauucau | 12120
| cuuuccuauc | gccgaguccu | ggaucuauua | cucgacuug | gguaugagc | cuaccaucgg | 12180
| gauaaguggu | aggcaaaaua | ggggccaaua | agcccuuggu | gucccaagaa | gacugaucga | 12240
| agucguacac | cucagucauu | uuuuaggaga | ggacuuaggc | ucuugugucc | u | 12291

<210> SEQ ID NO 24
<211> LENGTH: 3396
<212> TYPE: RNA
<213> ORGANISM: canine distemper virus

<400> SEQUENCE: 24

| | | | | | |
|---|---|---|---|---|---|
| uuuuuuauaa | uugcuuuuaa | gcgauaguga | aagcaguuuu | gcgccgguua | guagauuagu | 60

-continued

| | |
|---|---|
| caacgcuaca gauuaagcau gaguaauacu cuugaccauc ugguagaacu cguuuagguu | 120 |
| gucauccccc uugauauuuu uaagcagagc cagcauguua uguuugcgac uuugaucaac | 180 |
| ucugcuugau cugaucaaug augcaaguac agcuuuagaa ggugcgguau ccuuggguuu | 240 |
| guauccgauu gccgagcuag acucuuuguc aaugggauuc agcuggaggu cucucaauag | 300 |
| uugaccuuuu gagcccagag uaauaccacu guccuuccga uuaccgcggg augaugcggg | 360 |
| cugcuugaga acuuccgcua gugcucuucc ugaaucccuc ccuaugauag ggcggagcuc | 420 |
| uggauuaaug ucgacauuug ccguagggus ucccguguce uuccaaaac cagguauage | 480 |
| uaucauaaug cuugauagau gcccucaau cguggaaauc gcaauauuuu guuugcugau | 540 |
| uuguuucuua auugaaucag ucucuccuuu aagcaguaau aagguaucca guuuagaaag | 600 |
| uauugcuuga uuaucuucag uuaguuuagu aauggcagau cgaauuucuu guaucucaga | 660 |
| gaaaagcuca ucaucguacu cacugucaga cucagccuca uuugagguce ugggagggag | 720 |
| uugcguacca gacucgaguu ugcauuucug ggucaucuuu gcauucauug cagguuggcg | 780 |
| gacauuccec gcagacacac uuggcucuga ugauccccca guugacuuga gugcagauug | 840 |
| gguugcacca cuugucgauc cagcaacuau ccccauuccc ugugagacug accucucuuc | 900 |
| ugugcccuuu uuaauggauc cacacuccgg aacccuuguc uuaccuucgg gauuaugugg | 960 |
| gaacugcaga gucuucccau cccuuuucug aaucccuaca uuucgccuug ucuugagcag | 1020 |
| agcacuuaau uccucuucca ucagcaugcu cacaucagcu gcccgucug guuuaaggcc | 1080 |
| gaaagaauau ccccaguuag augaagcauu uccucggaa uaaucuucgc cagaauccuc | 1140 |
| agugcuauca ucagggcuuc cuucuccgcu cucgaauccu cgauuaccga cagugccugc | 1200 |
| agguaccacg agacugucag caucuucgau ucccuuaacc ucuuaccgc ugugaucaua | 1260 |
| aacaugauaa caucguauuc cagguccugg ugauguce cuuuaggga gcugcucugc | 1320 |
| uuccacaagc gcagaguugc uuucuccaca ucccggauua uuuuggagua cauggccgac | 1380 |
| auaguuugau ccuuuuguug gcucguguga uucaucgaga uucugagagu ccuccucuuc | 1440 |
| cugcaugccu guggnuccau ucucuuggcc ugggnugcag guuugguauc ugaugcugcu | 1500 |
| gaccucuuga aucccucaa ugucaggagg auucucucug agggcuuuga ggcauuccag | 1560 |
| cccuuugcug acaugguagg ccuguuccuc ugccauuuag ggauagaacg ggugguegga | 1620 |
| ugaaugguug aucgggnuug uuggacccgg guccuaaguu uuuuauaaug aguuuagaau | 1680 |
| gauaauuguu gacugaugca ggacuggucu ugaauauuua auugaguagc ucucuaucau | 1740 |
| uauaaacagg agaacuaucu ucacuggucc cagguugacu gagcaucuua guaagcaucc | 1800 |
| ucaucuuggc gauugcuucc aucgauuucc ggucaucauc auuccauca ucuuggguaa | 1860 |
| uuugggnguc guggcguggc ucacuccguu cagagcuguu gacgcucggg gugugcccug | 1920 |
| gaggccuuuc aucacugaag ugaaugggu aucgucucc ucccugguuu ucggaccucu | 1980 |
| uguugauggu cggggguugu ugauuagcga cuucggaucu uuccgagugc aggaagguaa | 2040 |
| uuugggauug cuugggacca guagcucgaa ucgucgguc cucuguuguc uuggaugcua | 2100 |
| uuucugacac cagcugagcu uccuccuugg ugaugccaag cucggcagca agugcagagc | 2160 |
| uuacuuugcc ggcagaucgu cuaaccauuu cuugcccgag ucugaaguag gcugggucaa | 2220 |
| aguaagaucg accgaaauuu aauccuccca uggaguuuuc aaguucaaca ccaaccccca | 2280 |
| uagcauaacu ccagagcaau ggguaggacc cugcacuaaa uuuguuuuga acagaguuuu | 2340 |
| ccaagauaac caugauggu gcuguuucac ccaucuguug auauagcauc augagggauu | 2400 |
| caauaguugu uaauucuccg gaaaacucau gcaacccaag agccggauac auaguuucaa | 2460 |

```
ugccaaacuu gauaguuagg augaaacuag cuaacccagc uuccacagug uaguuaucua    2520
uaucacaaau cauuucagca auucuaggcu uguucccugg ggaucuuuug auguccaaaa    2580
ugagugccac caugaaucgc cucaaagaua gguccucagc aaccuguuu cuaacaauau     2640 caagccagau uuuguucauu cuaaauucuc cgaccacacg ucuuugcugg guauacuuaa    2700
uccaccuucu caucuccgag ucggcugcag uaucaggagc agucaccgcu uuagcuagca    2760
ggauccaaau uugagccaaa auggaagcua guaauauauu gaauugcuca gcaucaucaa    2820
cuucuauguc uacuauaucc uuauucucca accagccuaa uugcccuuga gcuuucgacc    2880
cuucgucuac aauuugaag aacucaucug ccucagaauc cagacuugcu ccucuggaug     2940
caaauguaag accgcaaaca gaguugaugc uugguauuac cucuacuaac uugaugcuua    3000 caucagggguc gucuaugauc cucuggauca acugccaggg ggauuccacg aacaaggaga   3060
ggauacugau uaagaucca guuaauuuag ggccguugau uucuggauca ccaaccaacc    3120
uaacaagucu auccaauagu cgagaucuug uaacaaugcu ugaaucaccc gggauuagga   3180
cuauaaugac augcuuuauu ccucuuauug cuccccccgga gccagaggca agagggggguu 3240 ggucccgagu ccucuugaac agugugaggc uuuuaagaag gcuagccaua uuggaagguc   3300
ugaacccuga ccuuguucuc uaagguagga ucauugaccc uaaguuuuua auaaaauauu   3360
caauaauuua acuauccaua gccaacuuug ucuggu                             3396
```

<210> SEQ ID NO 25
<211> LENGTH: 59
<212> TYPE: DNA
<213> ORGANISM: canine distemper virus

<400> SEQUENCE: 25

```
atattcaaga ccagtcctgc atcagtcaac aattatcatt ctaaactcat tataaaaaa    59
```

<210> SEQ ID NO 26
<211> LENGTH: 5
<212> TYPE: DNA
<213> ORGANISM: Artificial Sequence
<220> FEATURE:
<223> OTHER INFORMATION: DNA reverse complement of SEQ ID NO:13

<400> SEQUENCE: 26

```
gcacc                                                                5
```

<210> SEQ ID NO 27
<211> LENGTH: 20
<212> TYPE: DNA
<213> ORGANISM: canine distemper virus

<400> SEQUENCE: 27

```
aggactcagg tagtccagca                                               20
```

<210> SEQ ID NO 28
<211> LENGTH: 3
<212> TYPE: DNA
<213> ORGANISM: canine distemper virus

<400> SEQUENCE: 28

```
ctt                                                                  3
```

<210> SEQ ID NO 29
<211> LENGTH: 12291
<212> TYPE: DNA

<213> ORGANISM: canine distemper virus

<400> SEQUENCE: 29

```
aggacacaag agcctaagtc ctctcctaaa aaatgactga ggtgtacgac ttcgatcagt     60
cttcttggga caccaagggc ttattggccc ctattttgcc taccacttat cccgatggta    120
ggctcatacc ccaagtcaga gtaatagatc caggactcgg cgataggaaa gatgaatgct    180
tcatgtatat ttttctactg ggtataatag aagacaatga tggcctcgga cccccaattg    240
gaagaacatt tggattgctg cctttgggag ttgggcgtac tacagccaga cctgaggagt    300
tattgaaaga agccaccctg ttggatattg tggcaaggcg aactgcaggt gtcaaggaac    360
aactggtatt ttataataac accccattgc acatcttaac tccgtggaaa aaggtcctta    420
cgagtggaag tgtgttcagt gcaaatcaag tctgtaacgc agtcaatcta ataccattag    480
acatagcaca aagattcagg gtggtatata tgagcatcac tcgactatca gacgatggaa    540
gttacagaat tccccgcggg atgtttgaat tccgctccag gaatgcttta gcatttaaca    600
ttttagtcac cattcaagtt gagggagatg tctgttcaag ccgaggtaat ttgagcatgt    660
tcaaagatca ccaagtaaca ttcatggtcc gtatcggcaa tttcaggcgt aagaaaaacc    720
aagcttactc tgctgattat tgtaaactga aaattgaaaa gatgggatta gtgtttgctc    780
taggagggat aggaggaaca agtcttcaca tacgatgtac tggtaagatg agcaaggcct    840
tgaatgccca gctaggtttc aagaaaatcc tgtgttaccc gctcatggag atcaatgaag    900
atttgaatcg atctctatgg agattagagt gcaaaatagt aaggatccaa gcagtcttgc    960
aaccatcagt cccacaagat ttcagagttt ataatgatgt tatcgtcagc gatgatcagg   1020
gtcttttcaa atttctctaa atcattagtt catgaactaa aactcaaacg ccttagtagc   1080
attgcccaag atcccttgat ccccgcaagc gaggattgag ggtataaata tcgactgtct   1140
agatgttgct cctgcatttt gagcgtggcc tataggtttc tagactgccc atccgtgccc   1200
acaattccag tgacgcctca atatgaaaat agctgaatca aaacagttct tgcttaagat   1260
tgggttgatc attatcggac caagaaatga atggatgcct ggggttttga gcttcgcttc   1320
taggaatctc actttaacag ttatactccc acgcacttgc ctgatctcaa gccatcacta   1380
gtagtcttgt ttcacggagt gatgactgtc catctttcta tcacagctca ttaataatta   1440
atcaaaactt agggtccagg acgtagcaag ccaacaggcc aaccaagtcc accagcccga   1500
ggccaggcag gaaccccac aaacagccaa gccccatgca caaggaaatc cccaaaagct    1560
ccaaaaccca cacacatacc caacaaaacc gccccccaca acccagcacc ggacccgacg   1620
agaccaggac ctcccgagca cgacacagca taacgtcagc tcagcgatcc acgaactatg   1680
atcctcgaac attggacaga cccgtctcct acaccatgaa caggaccagg tctcgcaagc   1740
aaaccagcta cagattggag aacatctcag ttcacggaaa ccacgaggct attatccagc   1800
acatgccaga gagtgtctcc aaaggagcga gatcccagat cgaaaggcgg caacccaatg   1860
caatcaactc aggctctcag tgctcctggt tagtcctgtg gtgcctcgga atagccagtc   1920
tctttctttg ttccaaggct cagatacatt ggaataattt gtcaactatt gggattattg   1980
ggactgatag tgtccattat aagatcatgg ctaggcccag tcaccagtac ttggtcataa   2040
aactgatgcc taatgtttca cttatagata attgtaccaa agcagaatta ggtgagtatg   2100
agaaattatt gaattcagtc ctcgaaccaa tcaaccaagc tctgactcta atgaccaaga   2160
atgtgaagcc cttgcagtca ttagggtcag ctaggagaca aaggcgtttt gcaggagtgg   2220
tacttgcagg tgcagcttta ggagtggcta cagctgcaca aatcactgca ggaatagctt   2280
```

```
tacatcaatc caacctcaat gctcaagcaa tccaatctct tagaaccagc cttgaacagt   2340
ctaacaaagc tattgaagaa attagggagg ctacccaaga aaccgtcatt gccgttcagg   2400
gagtccagga ttacgttaac aacgaactcg tccctgctat gcaacatatg tcatgtgaat   2460
tagttgggca gagattaggg ttaaaactgc ttaggtatta tactgagtta ttgtcaatat   2520
ttggcccgag tttacgtgac cctatttcag ccgagatatc aattcaagca ctgagttatg   2580
ctcttggagg agaaattcat aagatacttg agaagttggg atactctgga ggtgatatga   2640
ttgcaatctt ggagagtcgg gggataaaaa caaaataaac tcatgttgat attcccggga   2700
aattcatcat cctaagtatc tcatacccaa ctttatcaga agtcaagggg gttatagtcc   2760
acagactgga agcagtttct tacaacatag gatcacaaga gtggtacacc actgtcccga   2820
ggtatattgc aactaatggt tacttaatat ctaattttga tgagtcatcc tgtgtattcg   2880
tctcagagtc agccatttgt agccagaact ccctgtaccc catgagccca ctcttacaac   2940
aatgtattag gggcgacact tcatcttgtg cccggacctt ggtatctggg actatgggca   3000
acaaatttat tctgtcaaaa ggtaacatcg tcgcaaattg tgcgtctata ctatgtaagt   3060
gttatagcac aagcacaatt attaatcaga gtcctgataa gttgctgaca ttcattgcct   3120
ccgatacctg cccactggtt gaaatagatg gtgtaactat ccaagttgga ggcaggcaat   3180
accctgatat ggtatatgaa agcaaagttg ccttaggccc tgctatatca cttgagaggt   3240
tagatgtagg tacaaattta gggaacgccc ttaagaaact ggatgatgct aaggtactga   3300
tagactcctc taaccagatc cttgagacag ttaggcgctc ttcctttaat tttggcagtc   3360
tcctcagcgt tcctatatta agtggtacag ccctggcttt gctgttgctg atttactgtt   3420
gtaaaagacg ctaccaacag acactcaagc ggaatactaa ggtcgatccg gcatttaaac   3480
ctgatctaac cggaacttcg aaatcctatg tgagatcact ctgaagtatt ctggtcatat   3540
atctcgcttg attgccagat ttgatatcta ttaaccccgc ccaatttcct tcaagagtca   3600
ctcaactgca ataaacattg gaaaagactg accatgatta tcgtaattaa agaaaactta   3660
gggctcaggt agtccagcaa tgctctccta ccaagacaag gtgggtgcct tctacaagga   3720
caatgcaaga gccaattcat ccaagctgtc cccagtgaca gaagagcatg ggggcaggag   3780
accaccttat tgttgttttg tccttctcat cctattggtt ggaatcctgg ccctgcttgc   3840
tatcactgga gttcgatttc accaagtatc aactagcaat atggaattta gcagattgct   3900
gaaagaggat atggagaaat cagaggccgt acatcatcaa gtcatagatg tcttgacacc   3960
gctcttcaag attattgggg atgagattgg gttacgttg ccacaaaagc taaacgagat   4020
caaacaattt atccttcaaa agacaaattt cttcaatccg aacagagaat tcgatttccg   4080
cgatctccac tggtgcatta acccgcctag taaggtcaag gtgaattta caaattactg   4140 tgagacaatt gggatcagaa atctattgc atcggcagca atcccatcc ttttatcagc   4200 cctctctggg ggcaggagtg acatattccc accatacaga tgcagtggag ctactacttc   4260
agtaggcaaa gttttccccc tatcagtctc gttatccatg tctttgatct caagaacctc   4320
agagataatc aatatgctga ccgctaccct agacggcgtg tatggcaaaa cttacttgct   4380
agtgcctgat gatatagaac gggagttcga cactcaagag attcgagtct ttgaaatagg   4440
gttcattaaa aggtggctga atgacatgcc attactccaa acaaccaact atatggtcct   4500
cccggagaat tccaaagcca aggtatgtac catagcagtg ggtgagttga cactggcttc   4560
cttgtgtgta gaagagagca ctgtattatt ataccatgac agcagggggtt cacaagatgg   4620
```

```
tattctagta gtgacactgg ggatatttgg ggcaacacct atggatcata ttgaggaagt    4680
gatacctgtc gctcacccat caatggagaa aatacatata acaaaccacc gtggttttat    4740
aaaagattca attgcaacct ggatggtgcc tgccctggcc tctgagaaac aagaagaaca    4800
aaaaggttgg ctggagtcag cttgtcaaag aaaaacctac cccatgtgca accaaacgtc    4860
atgggaaccc ttcggaggag gacagttgcc atcttatggg cggttgacat tacctctaga    4920
tgcaagtgtt gaccttcaac ttaacatatc gttcacatac ggtccggtta tactgaatgg    4980
agatggtatg gattattatg aaagcccact tttgaactcc ggatggctta ccattcctcc    5040
taaaaacgga acaatccttg gattgataaa caaagcaagt agaggagacc agttcactgt    5100
gataccccaa gtattaacat tgcgcccag ggaatcatgt ggaaattgtt atttacctat    5160
tcaaacatct caaattatag atagagatgt cctcatcgag tccaatgtag tggtgttgcc    5220
tacacagagt tttagatatg tcatagcaac gtatgatata tcacgaaatg atcatgcgat    5280
tgtttattat gtttatgacc caatccggac gatttcttat acgcactcat ttagactaac    5340
taccaagggt agacctgatt tcctaaggat tgaatgtttt gtgtgggatg taatttgtg    5400 gtgtcaccaa ttttacagat acgaggctaa catcgccaac tctacaacca gtgttgagaa    5460
tttagtccgt ataagattct catgtaaccg ttcaaatccc tgacagtata atgatacaca    5520
tctcaattgg acttaggcat gatgagtatg gtgaaaaatc ccttacagat gattgaatta    5580
aaccatctcc agcattataa aaaaactaag gatccaggat ccttttagcc atggactctg    5640
tgtcagtgaa ccagattcta taccctgagg tccatctaga tagcccaatt gtaaccaata    5700
agctagtagc tatttagaa tacgcacgaa ttagacatag ctatcaactc cttgatacaa    5760
cattagtgcg taatatcaaa gagagaattt cagaagggtt ctcaaaccag atgatcatta    5820
actgcatcga aatcgggagc attattaatc agaccttgtt atcttatccc aaacacaacc    5880
atgtgatata cccaaattgc aacaaacttc tatttcatgc acaggatcga gtcacctctc    5940
tgaggctgag aaatatattc aaaagaggaa atagcatcta tagcaaaata acagacgggg    6000
tcaaaaaatg cttaaacgat attaatctta atattggttt aggggggcgca ctggacaaga    6060 ctattgggac caaaattgat gaagcaggca taattatgca aagctcacag tggttcgaac    6120 cttccttct atggtttaca attaaaacag aaatgagatc agtgattaaa tcctctactc    6180
acaactgtcg caagcggagg cagaatcctg tctttgtaaa aggtgaatca tttaatgtgc    6240
tagtgtctag ggaccttgta tgtattattg atctcaccag tcacaatgtt tattacctaa    6300
catttgaaat ggtcttgatg tactgtgatg taatagaagg gaggctaatg actgatactg    6360
ctatggcaat tgatcaacgt tactcaactt tgcatgtcag gatcaggtat ctctgggatc    6420
taattgacgg attttccccg gatctgggaa attcaaccta tcaattggtg gctctactgg    6480
agcctctctc attggcttac ttgcagttaa aagacatcac cttctctctc aggggtgctt    6540
ttctgagtca ctgctttgct gaaattcagg agattttaca ggacaatggc ttctatactg    6600
aagagacgtt ccaaacttta acccaagctc tagacttcgt tttcatcaca gaggatatac    6660
atataacagg agaaatcttt tccttcttta gaagtttcgg tcacccaagg ttagaagcaa    6720
taacagcagc agaaaacgta cggaaacaca tgaatcaacc caagtttgtc tcttatgaga    6780
ctatgatgaa gggacatgct atattctgtg ggataatcat taacggttat cgggatagac    6840 atggggaac ttggcctccg atggatcttc ctgttcatgc atctcccatc atcagaaatg    6900
ctcatgcctc aggggaggga atcacctata gtcaatgtat agaaaactgg aaatcctttg    6960
caggaattcg atttaaatgc tttatgcctc ttagcctaga cagtgatttg accatgtacc    7020
```

-continued

```
tgaaagataa ggctttggca gccctaagaa aagagtggga ctcagtgtac ccaaaagaat    7080
tcctcaggta caatccacct cgctccactg agtctcggag acttgttaat gtgtttctag    7140
aggactctca gtttgaccct tataacatga ttatgtacgt tatctcaggt caatatctag    7200
aagatcctga tttcaaccta tcatacagtc tcaaagagaa agagattaaa gaggtaggga    7260
ggctattcgc taaaatgacc tacaaaatgc gagcctgtca ggtcatagca gagaacttga    7320
tatctaatgg aattgggaag tacttcaagg acaatgggat ggcaaaggat gaacacgatc    7380
tcactaaagc attgcacact ctggctgtgt ccggggttcc gaaagacaag aaagacttcc    7440
atcgtggcct cactaaccag agtaaatccc tgaaacctgc accttatcga ggagcacttc    7500
actccgtctc ttccccaagt agtagatata tagacccaaa cccaaatttt tgcaccagta    7560
gaagagaaga caatgacata gagatctatg aaactgtaag tgcatttata actacggatc    7620
tcaaaaagta ctgtctgaat tggcgttatg agaccatcag tatttttgct cagagattaa    7680
atgaaatcta cggtctcccc tcattttttcc aatggttaca cagaagattg gaacagtcga    7740
tcttatacgt aagtgacccc cactgccctc cagatctcga tcgtcatgtg gacttgaata    7800
cagcccctaa ctctcaaata ttcatcaaat acccaatggg gggggtggag ggttattgtc    7860
agaagttgtg gactattaac accataccct atttgtactt ggcggcacat gagagcggtg    7920
tcagaattgc atcacttgtc caaggtgata accaaactat tgctgtcact aaaagagtac    7980
caagcacctg gtcctatgcc ttgaagaaat ctgaagccag tcgagtgacc gcagaatact    8040
ttatagcctt gagacagagg ttacatgatg tcggacatca tttgaaagca aatgaaacaa    8100
taatctcttc ccactttttt gtatactcaa aagggatcta ttatgacggg atgttaatct    8160
cacaatccct gaagagtata gctaggtgtg tatttggtc agaaacaata gtggatgaga    8220
cccgagccgc gtgcagcaac atttcaacaa cattagcgaa agccattgag aaagggtttg    8280
accgatattt agcctacgca ctgaacattt taaaaatcat tcaacaagta ttaatttcat    8340
taggattcac tatcaattca gctatgacac gggatgtgat agaacccctc gtacaagatc    8400
actgtctctt gaccaagatg gcaattctcc ccgcacccat tggcggtctt aattacctca    8460
atatgagtag gctctttgtc aggaatatcg gggatcccgt gacatcttct attgctgacc    8520
tcaaacgaat gatccgatca ggccttcttg gagtggagat tctacatcag gtcatgaccc    8580
aatacccagg tgactcttct tatttagatt gggcaagtga cccttattct gccaatctgc    8640
cctgtgtcca gagcataacc cgactcctta aaaatatcac agccaggcat gtccttatca    8700
acagtccaaa tccgatgctg agaggattgt tccatgatga aagtcaggat gaggatgaag    8760
ctttagcagc tttcttaatg gataggaaaa ttattatccc aagggctgca catgaaattc    8820
tagataacac gatcacaggt gcaagagagg caatcaccgg aatgctagac accacaaagg    8880
ggttgatacg agcaagcatg aaaagaggag gtctaacccc tagaataata acccgtttgt    8940
caacttatga ttatgaacaa tttagggcag gtatcagact gttgtcaggg aaggggcatg    9000
atccgctcat cgatcaagac tcatgttccg tccagctagc gagagcatta aggaaccaca    9060
tgtgggccaa gctggcgaag ggtcgtccta tttatggtct agaagtcccg gatatccttg    9120
aatcaatgaa gggttatatg atcagaagac atgaatcctg tttgctttgt gcatcaggct    9180
ctcataacta tggttggttt tttgtaccag cgaattgcca attggatagt attacagagg    9240
gaacatctgc actgagggtg ccatacatag ggtccacaac agaagaaaga acagacatga    9300
aactagcatt cgtcaaatct cctagtaggt ctctgaaatc agcagtgaga atagcaactg    9360
```

```
tgtactcatg ggcctatggt gatgatgacg aatcttggca agaggcttgg accttggcaa    9420
aacagagagc gaacatctca cttgaggaat tacggatgat tacccccaatt tccacttcta   9480 ctaatctagc tcaccgacta agagacaaga gtactcaagt caaatactca gggacctctc   9540
tcatcagagt ggcacgttat gcaactatct cgaatgataa tctttctttt attatagatg   9600
acaagaaagt ggacacaaat tttatttatc aacaaggtat gctcctgggc ctggggatcc   9660
ttgagcactt atttagattg tcttcaacca ccggcgactc taataccgta ttacatttac   9720
atgttgaaac agattgttgc gtaatacccca tgagcgacca tccaagagtc ccagggctca   9780
gaaatgtcgt cataccaaga aatatctgta caaatccttt gatttatgac agtaacccta   9840
ttattgagaa agatgcagtc agactttata accagagtca cagaaagcac attgtagagt   9900
ttgtcacatg gacaacaggg cagctttatc atgtgctagc taagtctact gctatgtcta   9960
tggttgagat gattacaaag tttgaaaagg accacctaaa tgaagtctct gcgttaattg   10020
gcgatgatga tatcaatagt tttatcactg agtttcttct agttgagcct agattattta   10080
ctgtatatct aggccaatgt gctgcaatca actgggctt tgaaattcat tatcaccgac    10140
cttctggaaa gtaccaaatg ggtgagttgt tgttctcttt cctgagtaga atgagtaaag   10200
gagtcttcaa aattttaacc aatgcattga gccatcctaa agtatataga cggttttggg   10260
acagtgggat gattgaacct attcatggac cctctcttga ctcccaaaac ctacatataa   10320
ctgtatgcaa cctgatctat aactgttaca tgatttacct agaccttctg ttaaatgatg   10380
aattagatga tttctcattc attttatgcg aaagtgacga ggatgtcata cctgaaagat   10440 tgacaacat acaagccagg cacctatgca tcttatctga cctttattgt aaccctcgtg    10500
attgtcccca gattcgtggg ttgacaccaa cacagaaatg tgctgtgtta tcggggtact   10560
taaagtcaaa agccctagaa tcccatgttg gtctgacatg gaatgacaaa cctatcttaa   10620
tagatcaata ttcatgttcc ctgacatatc ttagaagagg ctcaatcaag cagataagac   10680
tgagagtgga tcccggattc atcactgatg ctgttggatg cttagaaagg cgtcctctaa   10740
gaaataattc tacctctaag gcctcagaat taaagtcaga atttgaccca ccgaaagatg   10800
acctggccaa acttctgagt cagctgtcaa caaggacaca taacttaccc attacaggat   10860
taggagtccg gaactatgag gttcactcat tcagaagaat tgggatcaac tctactgcat   10920
gttacaaggc agttgaaata gcttctgtga ttaagaacga atttacgtct gaagaacacg   10980
gattattcct aggagaaggt tcaggtgcaa tgttgacagt atataaagag ctattaagat   11040
tgtcaagatg ttattataac agtggtgtgt cagtagagtc cagaactgga caacgagaga   11100
tttcacctta ccccttctgag gtcagtctgg tggaacatca attaggactc gataaattgg   11160
cgactgtgct tttcaatggc agaccagaag taacttgggt tgggagtgtt gattgttaca   11220
agtacatact gagccagatc tctgctagca gtcttgggtt gattcactcg gatatagagt   11280
cactaccgga caaagacata atcgaaaagt tggaggaatt gtctgctata ttatcaatga   11340
ctttgatatt agggaaggta gggtcagtgt tagtaattaa gatcatgcca gctagtggcg   11400
actgggttca aggatttatt ttatatgcac tcccacattt tcttcgaagt ttcatagttt   11460
acccaagata cagcaatttt gtgtcaacag aggcctacct tgttttttact ggtcttagag   11520 cagggagact agtcaatccg gagggggatta acaacagat tttgcgagtc ggtattcgaa    11580
cttcacctgg gttggtaggg cacatccttt catcaaagca ggcagcatgt gtgcagtctt   11640
tgcacggacc tccattcat gctgaatcct tcaatcctca cctccagggt ttaacaagta    11700
ttgagaaggt attaatcaat tgtgggctta caattaatgg tcttaaggta tgtaagaacc   11760
```

```
tgcttcacca tgatatttcg tcaggcgagg aagggctgaa aggatctatc acgatccttt     11820
accgggaact cgcaaggttc aaggataacc accaatcttc acatggaatg ttccatgcat     11880
accctgtgtt aatcgcaagt caggaaaggg agctcgtatc tatcattgca aagaagtact     11940
gtggctatat tttgctttac tcgggagact tatacgaaat taccaggatt gtccgaaacc     12000
tgaaagccaa ccacataatt ttcgacttgc atcgtaactt atttatggat aatctgtccg     12060
gatctgacag gtctctcatc ctaacgacaa tccccaaaaa gaattggctc tttcagcttg     12120
agacaaaaga gataaaggag tggttcaaat tgttaggtta tagtgcactg attagaaatc     12180
actaacaggt tagtctggct cctagccccc tactattcat tgctatcaaa cttggttata     12240
cgaaaaaaaa caacggttat taataagtta tcatacccag ctttgtctgg t             12291

<210> SEQ ID NO 30
<211> LENGTH: 3396
<212> TYPE: DNA
<213> ORGANISM: canine distemper virus

<400> SEQUENCE: 30
accagacaaa gttggctatg gatagttaaa ttattgaata ttttattaaa aacttagggt       60
caatgatcct accttagaga acaaggtcag ggttcagacc taccaatatg gctagccttc      120
ttaaaagcct cacactgttc aagaggactc gggaccaacc ccctcttgcc tctggctccg      180
ggggagcaat aagaggaata aagcatgtca ttatagtcct aatcccgggt gattcaagca      240
ttgttacaag atctcgacta ttggatagac ttgttaggtt ggttggtgat ccagaaatca      300
acggccctaa attaactggg atcttaatca gtatcctctc cttgttcgtg gaatcccctg      360
gacagttgat ccagaggatc atagacgacc ctgatgtaag catcaagtta gtagaggtaa      420
taccaagcat caactctgtt tgcggtctta catttgcatc cagaggagca agtctggatt      480
ctgaggcaga tgagttcttc aaaattgtag acgaagggtc gaaagctcaa ggcaattag       540 gctggttgga gaataaggat atagtagaca tagaagttga tgatgctgag caattcaata      600
tattactagc ttccatttg gctcaaattt ggatcctgct agctaaagcg gtgactgctc       660
ctgatactgc agccgactcg gagatgagaa ggtggattaa gtatacccag caaagacgtg      720
tggtcggaga atttagaatg aacaaaatct ggcttgatat tgttagaaac aggattgctg      780
aggacctatc tttgaggcga ttcatggtgg cactcatttt ggacatcaaa agatccccag      840
ggaacaagcc tagaattgct gaaatgattt gtgatataga taactacact gtggaagctg      900
ggttagctag tttcatccta actatcaagt ttggcattga aactatgtat ccggctcttg      960
ggttgcatga gttttccgga gaattaacaa ctattgaatc cctcatgatg ctatatcaac     1020
agatgggtga aacagcacca tacatggtta tcttggaaaa ctctgttcaa acaaaattta     1080
gtgcagggtc ctacccattg ctctggagtt atgctatggg ggttggtgtt gaacttgaaa     1140
actccatggg aggattaaat ttcggtcgat cttactttga cccagcctac ttcagactcg     1200
ggcaagaaat ggttagacga tctgccggca aagtaagctc tgcacttgct gccgagcttg     1260
gcatcaccaa ggaggaagct cagctggtgt cagaaatagc atccaagaca acagaggacc     1320
ggacgattcg agctactggt cccaagcaat cccaaattac cttcctgcac tcggaaagat     1380
ccgaagtcgc taatcaacaa ccccgacca tcaacaagag gtccgaaaac cagggaggag      1440
acagataccc cattcacttc agtgatgaaa ggcctccagg gcacacccca gacgtcaaca     1500
gctctgaacg gagtgagcca cgccacgaca cccaaattac ccaagatgat ggaaatgatg     1560
```

```
atgaccggaa atcgatggaa gcaatcgcca agatgaggat gcttactaag atgctcagtc    1620
aacctgggac cagtgaagat agttctcctg tttataatga tagagagcta ctcaattaaa    1680
tattcaagac cagtcctgca tcagtcaaca attatcattc taaactcatt ataaaaaact    1740
taggacccgg gtccaacaaa cccgatcaac cattcatccg accacccgtt ctatccctaa    1800
atggcagagg aacaggccta ccatgtcagc aaagggctgg aatgcctcaa agccctcaga    1860
gagaatcctc ctgacattga ggagattcaa gaggtcagca gcatcagata ccaaacctgc    1920
aacccaggcc aagagaatgg aaccacaggc atgcaggaag aggaggactc tcagaatctc    1980
gatgaatcac acgagccaac aaaaggatca aactatgtcg gccatgtact ccaaaataat    2040
ccgggatgtg agaaagcaa ctctgcgctt gtggaagcag agcagctccc taaagaggac    2100
atccaaccag gacctggaat acgatgttat catgtttatg atcacagcgg tgaagaggtt    2160
aagggaatcg aagatgctga cagtctcgtg gtacctgcag gcactgtcgg taatcgagga    2220
ttcgagagcg gagaaggaag ccctgatgat agcactgagg attctggcga agattattcc    2280
gaaggaaatg cttcatctaa ctggggatat tctttcggcc ttaaaccaga cagggcagct    2340
gatgtgagca tgctgatgga agaggaatta agtgctctgc tcaagacaag cagaaatgta    2400
gggattcaga aaagggatgg gaagactctg cagttcccac ataatcccga aggtaagaca    2460
agggttccgg agtgtggatc cattaaaaag ggcacagaag agaggtcagt ctcacaggga    2520
atggggatag ttgctggatc gacaagtggt gcaacccaat ctgcactcaa gtcaactggg    2580
ggatcatcag agccaagtgt gtctgcgggg aatgtccgcc aacctgcaat gaatgcaaag    2640
atgacccaga atgcaaaact cgagtctggt acgcaactcc ctcccaggac tcaaatgag    2700 gctgagtctg acagtgagta cgatgatgag cttttctctg agatacaaga aattcgatct    2760
gccattacta aactaactga agataatcaa gcaatacttt ctaaactgga taccttatta    2820
ctgcttaaag gagagactga ttcaattaag aaacaaatca gcaaacaaaa tattgcgatt    2880
tccacgattt agggggcatct atcaagcatt atgatagcta tacctggttt tggaaaggac    2940
acgggagacc ctacggcaaa tgtcgacatt aatccagagc tccgccctat catagggagg    3000
gattcaggaa gagcactagc ggaagttctc aagcagcccg catcatcccg cggtaatcgg    3060
aaggacagtg gtattactct gggctcaaaa ggtcaactat tgagagacct ccagctgaaa    3120
cccattgaca aagagtctag ctcggcaatc ggatacaaac caaaggatac cgcaccttct    3180
aaagctgtac ttgcatcatt gatcagatca agcagagttg atcaaagtcg caaacataac    3240
atgctggctc tgcttaaaaa tatcaaggga gatgacaacc taaacgagtt ctaccagatg    3300
gtcaagagta ttactcatgc ttaatctgta gcgttgacta atctactaac cggcgcaaaa    3360
ctgctttcac tatcgcttaa aagcaattat aaaaaa                              3396
```

<210> SEQ ID NO 31
<211> LENGTH: 1755
<212> TYPE: DNA
<213> ORGANISM: canine parvovirus

<400> SEQUENCE: 31

```
atgtctgatg gcgccgtgca gcctgatggc ggacagcctg ctgtgcggaa tgagagagcc     60
accggcagcg gcaatggatc tggcggaggc ggcggagggg gaagtggcgg agtgggaatt    120
agcaccggca ccttcaacaa ccagaccgag ttcaagttcc tggaaaacgg ctgggtggaa    180
atcaccgcca acagcagcag actggtgcac ctgaacatgc ccgagagcga gaactaccgg    240
cgggtggtcg tgaacaacct ggacaagacc gccgtgaacg gcaacatggc cctggacgat    300
```

-continued

```
acccacgccc agatcgtgac accctggtcc ctggtggatg ccaatgcctg gggcgtgtgg    360
ttcaaccccg gcgactggca gctgatcgtg aacaccatga gcgagctgca cctggtgtcc    420
ttcgagcagg aaatcttcaa cgtggtgctg aaaaccgtgt ccgagagcgc cacacagccc    480
cccaccaagg tgtacaacaa cgacctgacc gcctccctga tggtggctct ggacagcaac    540
aacaccatgc ccttcacccc tgccgccatg cggagcgaga cactgggctt ctaccctgg    600 aagcccacca tccctacccc ctggcggtac tacttccagt gggacagaac cctgatcccc    660
agccacacag gcaccagcgg caccctacc aacatctacc acggcaccga ccccgacgac    720
gtgcagttct acaccatcga gaacagcgtg cccgtgcatc tgctgagaac cggcgacgag    780
ttcgccacag gcacattctt tttcgactgc aaaccctgcc ggctgaccca cctggcag    840 accaatagag ccctgggcct gccccccattc ctgaacagtc tgcctcaggc cgagggcggc    900
accaactttg gctatatcgg cgtgcagcag gacaagcgga gaggcgtgac acagatgggc    960
aagaccaact acatcaccga ggccacaat atgcggcctg ccgaagtggg ctacagcgcc   1020
ccctactaca gcttcgaggc cagcacccag ggccccttca agacacctat tgccgccgga   1080
agaggcggag cccagaccga tgagaatcag ggcgccgacg gcaaccccag atacgccttt   1140
ggcagacagc acggccagaa accaccacc accggcgaga cacccgagcg gttcacctat   1200
atcgcccacc aggacaccgg cagataccc gagggcgact ggattcagaa catcaacttc   1260
aacctgcccg tgaccgacga caacgtgctg ctgcccacag atcccatcgg cggcaagacc   1320
ggcatcaact acaccaatat cttcaacacc tacggccctc tgaccgccct gaacaacgtg   1380
ccccccgtgt accccaacgg acagatctgg gacaaagagt tcgacaccga cctgaagccc   1440
cggctgcatg tgaacgcccc tttcgtgtgc cagaacaact gccctggcca gctgtttgtg   1500
aaggtggccc ccaacctgac caacgagtac gaccctgacg ccagcgccaa catgagccgg   1560
atcgtgacct acagcgactt ctggtggaag ggcaagctgg tgttcaaggc caagctgcgg   1620
gcctctcaca cctggaaccc catccagcag atgagcatca acgtggacaa ccagttcaac   1680
tacgtgccca gcaacatcgg cggaatggaa atcgtgttcg agcggtccca gctggccccc   1740
agaaagctgt actaa                                                    1755

<210> SEQ ID NO 32
<211> LENGTH: 1701
<212> TYPE: DNA
<213> ORGANISM: swine influenza virus

<400> SEQUENCE: 32
atgaagaccg tgatcgccct gagttacatc ttctgcctgg tgtttgggca ggacctccct     60
ggtaaaggca caacacggc cacgctgtgc cttgggcacc acgccgtgcc gaacggcacc    120
cttgtgaaaa ctattaccga cgatcagatc gaggtgacca cgccaccga actggttcag    180 aattttagca tgggcaaaat ttgcaataac ccgcaccgca ttctggacgg ggccaactgc    240
acgctgatcg attcattgct gggtgatccc cactgcgatg ctttcaaaa cgaaaagtgg    300 gacttgttca tcgaacgcag caaggcattc agcaactgct acccatacga cgtgcccgaa    360
tacaccagcc tgcgaagcct gatcgcgagc tctgggaccc tggagttcac caatgagaac    420
ttcaattgga ccggagtgac ccaaaacggt ggctccagcg cctgtaaaag gggacccaat    480
aacagcttct ttagcaagtt gaattggctt acaagagcg gcaatactta cccgatgttg    540
aatgtgacca tgcccaacag tgacgacttt gataaactgt acatatgggg cgtgcaccat    600
```

```
cccagcacgg accgcgaaca gataaacctg tacgtgcagg ccagcgggaa gataatcgtg      660
agcaccaagc gcagccagca gaccatcatt cccaacattg gcagccgacc gtgggtgcgc      720
ggtctgagct cccgcatcag catatactgg accattgtca agccgggaga catcctgatc      780
atcaactcta atggcaatct tatcgcccca cgcggctact tcaagatgca gaccggcaaa      840
agcagtgtga tgaggagcga cgccccccatc gacacctgca atagcgaatg catcacccccc    900 aatggcagca tccccaacga caagcctttc cagaacgtga ataagatcac ctacggcgcg      960
tgccccaagt acatcaagca gaacaccctg aagctggcca ccggcatgcg caacatcccc      1020
gagcgacaga cacggggcat ttttggcgca atcgcagggt tcattgagaa tggctgggag      1080
ggaatggtta acggctggta cggcttccgc catcagaact ctgaaggaat cggccaagct      1140
gcggatctga gtccacgca agcagccatc aaccagatca cggcaagct taaccgcgtg        1200 attgaaaaga cgaacgagaa attccaccaa atagagaaag aattcagcga ggtggagggc      1260
cgcatccaag acctcgagcg ctacgtggag gacaccaaga tcgacctgtg gagctacaat      1320
gccgagctcc tggtcgcctt ggaaaaccaa cacaccattg acctgaccga cagcgagatg      1380
aataaactct tcgagaagac ccggaagcaa ctccgagaga cgccgaagca catgggtaat      1440
gggtgtttta agatctacca caagtgcgac aatagctgca tggagagcat ccgaaacgga      1500
acctacgacc acaacgagta ccgcgatgag gcagttaata accgcttcca aatcaaaagc      1560
gtggaactga agagtggcta taaggactgg atactgtgga tcagctttgc cataagctgc      1620
ttcctgctgt gcgccgtttg gttgggtttc atcatgtggg cctgtcaaaa gggcaatatt      1680
cgctgtaaca tctgcatttg a                                                1701
```

<210> SEQ ID NO 33
<211> LENGTH: 1845
<212> TYPE: DNA
<213> ORGANISM: Artificial Sequence
<220> FEATURE:
<223> OTHER INFORMATION: DNA reverse complement of SEQ ID NO:21

<400> SEQUENCE: 33

```
cttaggactc aggtagtcca gcagcaccat gtctgatggc gccgtgcagc ctgatggcgg       60
acagcctgct gtgcggaatg agagagccac cggcagcggc aatggatctg gcggaggcgg     120 cggagggggga agtggcggag tgggaattag caccggcacc ttcaacaacc agaccgagtt     180
caagttcctg gaaaacggct gggtggaaat caccgccaac agcagcagac tggtgcacct     240
gaacatgccc gagagcgaga actaccggcg ggtggtcgtg aacaacctgg acaagaccgc     300
cgtgaacggc aacatggccc tggacgatac ccacgcccag atcgtgacac cctggtccct     360
ggtggatgcc aatgcctggg gcgtgtggtt caaccccggc gactggcagc tgatcgtgaa     420
caccatgagc gagctgcacc tggtgtcctt cgagcaggaa atcttcaacg tggtgctgaa     480
aaccgtgtcc gagagcgcca cacagccccc caccaaggtg tacaacaacg acctgaccgc     540
ctccctgatg gtggctctgg acagcaacaa caccatgccc ttcaccctg ccgccatgcg     600 gagcgagaca ctgggcttct acccctggaa gcccaccatc cctacccccct ggcggtacta   660 cttccagtgg gacagaaccc tgatcccag ccacacaggc accagcggca ccctaccaa      720 catctaccac ggcaccgacc ccgacgacgt gcagttctac accatcgaga acagcgtgcc      780
cgtgcatctg ctgagaaccg gcgacgagtt cgccacaggc acattctttt tcgactgcaa      840
accctgccgc ctgaccccaca cctggcagac caatagagcc ctgggcctgc ccccattcct      900
gaacagtctg cctcaggccg agggcggcac caactttggc tatatcggcg tgcagcagga     960
```

```
caagcggaga ggcgtgacac agatgggcaa gaccaactac atcaccgagg ccacaatcat    1020
gcggcctgcc gaagtgggct acagcgcccc ctactacagc ttcgaggcca gcacccaggg    1080
cccctccaag acacctattg ccgccggaag aggcggagcc cagaccgatg agaatcaggg    1140
cgccgacggc aaccccagat acgcctttgg cagacagcac ggccagaaaa ccaccaccac    1200
cggcgagaca cccgagcggt tcacctatat cgcccaccag gacaccggca gataccccga    1260
gggcgactgg attcagaaca tcaacttcaa cctgcccgtg accgacgaca acgtgctgct    1320
gcccacagat cccatcggcg gcaagaccgg catcaactac accaatatct caacaccta     1380 cggccctctg accgccctga caacgtgccc cccgtgtac cccaacggac agatctggga    1440
caaagagttc gacaccgacc tgaagccccg gctgcatgtg aacgccccct tcgtgtgcca    1500
gaacaactgc cctggccagc tgtttgtgaa ggtggccccc aacctgacca acgagtacga    1560
ccctgacgcc agcgccaaca tgagccggat cgtgacctac agcgacttct ggtggaaggg    1620
caagctggtg ttcaaggcca agctgcgggc ctctcacacc tggaacccca tccagcagat    1680
gagcatcaac gtggacaacc agttcaacta cgtgcccagc aacatcggcg gaatggaaat    1740
cgtgttcgag cggtcccagc tggcccccag aaagctgtac taaatattca agaccagtcc    1800
tgcatcagtc aacaattatc attctaaact cattataaaa aactt                    1845

<210> SEQ ID NO 34
<211> LENGTH: 1791
<212> TYPE: DNA
<213> ORGANISM: Artificial Sequence
<220> FEATURE:
<223> OTHER INFORMATION: DNA reverse complement of SEQ ID NO:22

<400> SEQUENCE: 34
cttaggactc aggtagtcca gcagcaccat gaagaccgtg atcgccctga gttacatctt      60
ctgcctggtg tttgggcagg acctccctgg taaaggcaac aacacggcca cgctgtgcct     120
tgggcaccac gccgtgccga acggcaccct tgtgaaaact attaccgacg atcagatcga     180
ggtgaccaac gccaccgaac tggttcagaa ttttagcatg gcaaaattt gcaataaccc      240 gcaccgcatt ctggacgggg ccaactgcac gctgatcgat tcattgctgg gtgatcccca     300
ctgcgatggc tttcaaaacg aaaagtggga cttgttcatc gaacgcagca aggcattcag     360
caactgctac ccatacgacg tgcccgaata caccagcctg cgaagcctga tcgcgagctc     420
tgggaccctg gagttcacca atgagaactt caattggacc ggagtgaccc aaaacggtgg     480
ctccagcgcc tgtaaaaggg gacccaataa cagcttcttt agcaagttga attggcttta     540
caagagcggc aatacttacc cgatgttgaa tgtgaccatg cccaacagtg acgactttga     600
taaactgtac atatggggcg tgcaccatcc cagcacggac cgcgaacaga taaacctgta     660
cgtgcaggcc agcgggaaga taatcgtgag caccaagcgc agccagcaga ccatcattcc     720
caacattggc agccgaccgt gggtgcgcgg tctgagctcc cgcatcagca tatactggac     780
cattgtcaag ccgggagaca tcctgatcat caactctaat ggcaatctta tcgccccacg     840
cggctacttc aagatgcaga ccggcaaaag cagtgtgatg aggagcgacg ccccatcga     900 cacctgcaat agcgaatgca tcacccccaa tggcagcatc cccaacgaca gcctttcca     960 gaacgtgaat aagatcacct acggcgcgtg ccccaagtac atcaagcaga acaccctgaa    1020
gctggccacc ggcatgcgca acatcccga gcgacagaca cggggcattt ttggcgcaat    1080
cgcagggttc attgagaatg gctgggaggg aatggttaac ggctggtacg gcttccgcca    1140
```

-continued

```
tcagaactct gaaggaatcg gccaagctgc ggatctgaag tccacgcaag cagccatcaa    1200
ccagatcaac ggcaagctta accgcgtgat tgaaaagacg aacgagaaat tccaccaaat    1260
agagaaagaa ttcagcgagg tggagggccg catccaagac ctcgagcgct acgtggagga    1320
caccaagatc gacctgtgga gctacaatgc cgagctcctg gtcgccttgg aaaaccaaca    1380
caccattgac ctgaccgaca gcgagatgaa taaactcttc gagaagaccc ggaagcaact    1440
ccgagagaac gccgaagaca tgggtaatgg gtgttttaag atctaccaca agtgcgacaa    1500
tagctgcatg gagagcatcc gaaacggaac ctacgaccac aacgagtacc gcgatgaggc    1560
agttaataac cgcttccaaa tcaaaagcgt ggaactgaag agtggctata aggactggat    1620
actgtggatc agctttgcca taagctgctt cctgctgtgc gccgtttggt tgggtttcat    1680
catgtgggcc tgtcaaaagg gcaatattcg ctgtaacatc tgcatttgaa tattcaagac    1740
cagtcctgca tcagtcaaca attatcattc taaactcatt ataaaaaact t             1791
```

<210> SEQ ID NO 35
<211> LENGTH: 584
<212> TYPE: PRT
<213> ORGANISM: canine parvovirus

<400> SEQUENCE: 35

```
Met Ser Asp Gly Ala Val Gln Pro Asp Gly Gly Gln Pro Ala Val Arg
1               5                   10                  15

Asn Glu Arg Ala Thr Gly Ser Gly Asn Gly Ser Gly Gly Gly Gly Gly
            20                  25                  30

Gly Gly Ser Gly Gly Val Gly Ile Ser Thr Gly Thr Phe Asn Asn Gln
        35                  40                  45

Thr Glu Phe Lys Phe Leu Glu Asn Gly Trp Val Glu Ile Thr Ala Asn
    50                  55                  60

Ser Ser Arg Leu Val His Leu Asn Met Pro Glu Ser Glu Asn Tyr Arg
65                  70                  75                  80

Arg Val Val Val Asn Asn Leu Asp Lys Thr Ala Val Asn Gly Asn Met
                85                  90                  95

Ala Leu Asp Asp Thr His Ala Gln Ile Val Thr Pro Trp Ser Leu Val
            100                 105                 110

Asp Ala Asn Ala Trp Gly Val Trp Phe Asn Pro Gly Asp Trp Gln Leu
        115                 120                 125

Ile Val Asn Thr Met Ser Glu Leu His Leu Val Ser Phe Glu Gln Glu
    130                 135                 140

Ile Phe Asn Val Val Leu Lys Thr Val Ser Glu Ser Ala Thr Gln Pro
145                 150                 155                 160

Pro Thr Lys Val Tyr Asn Asn Asp Leu Thr Ala Ser Leu Met Val Ala
                165                 170                 175

Leu Asp Ser Asn Asn Thr Met Pro Phe Thr Pro Ala Ala Met Arg Ser
            180                 185                 190

Glu Thr Leu Gly Phe Tyr Pro Trp Lys Pro Thr Ile Pro Thr Pro Trp
        195                 200                 205

Arg Tyr Tyr Phe Gln Trp Asp Arg Thr Leu Ile Pro Ser His Thr Gly
    210                 215                 220

Thr Ser Gly Thr Pro Thr Asn Ile Tyr His Gly Thr Asp Pro Asp Asp
225                 230                 235                 240

Val Gln Phe Tyr Thr Ile Glu Asn Ser Val Pro Val His Leu Leu Arg
                245                 250                 255

Thr Gly Asp Glu Phe Ala Thr Gly Thr Phe Phe Phe Asp Cys Lys Pro
```

260                 265                 270
Cys Arg Leu Thr His Thr Trp Gln Thr Asn Arg Ala Leu Gly Leu Pro
            275                 280                 285

Pro Phe Leu Asn Ser Leu Pro Gln Ala Glu Gly Gly Thr Asn Phe Gly
        290                 295                 300

Tyr Ile Gly Val Gln Gln Asp Lys Arg Arg Gly Val Thr Gln Met Gly
305                 310                 315                 320

Lys Thr Asn Tyr Ile Thr Glu Ala Thr Ile Met Arg Pro Ala Glu Val
                325                 330                 335

Gly Tyr Ser Ala Pro Tyr Tyr Ser Phe Glu Ala Ser Thr Gln Gly Pro
            340                 345                 350

Phe Lys Thr Pro Ile Ala Ala Gly Arg Gly Gly Ala Gln Thr Asp Glu
        355                 360                 365

Asn Gln Gly Ala Asp Gly Asn Pro Arg Tyr Ala Phe Gly Arg Gln His
    370                 375                 380

Gly Gln Lys Thr Thr Thr Thr Gly Glu Thr Pro Glu Arg Phe Thr Tyr
385                 390                 395                 400

Ile Ala His Gln Asp Thr Gly Arg Tyr Pro Glu Gly Asp Trp Ile Gln
                405                 410                 415

Asn Ile Asn Phe Asn Leu Pro Val Thr Asp Asp Asn Val Leu Leu Pro
            420                 425                 430

Thr Asp Pro Ile Gly Gly Lys Thr Gly Ile Asn Tyr Thr Asn Ile Phe
        435                 440                 445

Asn Thr Tyr Gly Pro Leu Thr Ala Leu Asn Asn Val Pro Pro Val Tyr
    450                 455                 460

Pro Asn Gly Gln Ile Trp Asp Lys Glu Phe Asp Thr Asp Leu Lys Pro
465                 470                 475                 480

Arg Leu His Val Asn Ala Pro Phe Val Cys Gln Asn Asn Cys Pro Gly
                485                 490                 495

Gln Leu Phe Val Lys Val Ala Pro Asn Leu Thr Asn Glu Tyr Asp Pro
            500                 505                 510

Asp Ala Ser Ala Asn Met Ser Arg Ile Val Thr Tyr Ser Asp Phe Trp
        515                 520                 525

Trp Lys Gly Lys Leu Val Phe Lys Ala Lys Leu Arg Ala Ser His Thr
    530                 535                 540

Trp Asn Pro Ile Gln Gln Met Ser Ile Asn Val Asp Asn Gln Phe Asn
545                 550                 555                 560

Tyr Val Pro Ser Asn Ile Gly Gly Met Glu Ile Val Phe Glu Arg Ser
                565                 570                 575

Gln Leu Ala Pro Arg Lys Leu Tyr
            580

<210> SEQ ID NO 36
<211> LENGTH: 566
<212> TYPE: PRT
<213> ORGANISM: swine influenza virus

<400> SEQUENCE: 36

Met Lys Thr Val Ile Ala Leu Ser Tyr Ile Phe Cys Leu Val Phe Gly
1               5                   10                  15

Gln Asp Leu Pro Gly Lys Gly Asn Asn Thr Ala Thr Leu Cys Leu Gly
            20                  25                  30

His His Ala Val Pro Asn Gly Thr Leu Val Lys Thr Ile Thr Asp Asp
        35                  40                  45

```
Gln Ile Glu Val Thr Asn Ala Thr Glu Leu Val Gln Asn Phe Ser Met
 50                  55                  60
Gly Lys Ile Cys Asn Asn Pro His Arg Ile Leu Asp Gly Ala Asn Cys
 65                  70                  75                  80
Thr Leu Ile Asp Ser Leu Leu Gly Asp Pro His Cys Asp Gly Phe Gln
                     85                  90                  95
Asn Glu Lys Trp Asp Leu Phe Ile Glu Arg Ser Lys Ala Phe Ser Asn
                    100                 105                 110
Cys Tyr Pro Tyr Asp Val Pro Glu Tyr Thr Ser Leu Arg Ser Leu Ile
                115                 120                 125
Ala Ser Ser Gly Thr Leu Glu Phe Thr Asn Glu Asn Phe Asn Trp Thr
130                 135                 140
Gly Val Thr Gln Asn Gly Gly Ser Ser Ala Cys Lys Arg Gly Pro Asn
145                 150                 155                 160
Asn Ser Phe Phe Ser Lys Leu Asn Trp Leu Tyr Lys Ser Gly Asn Thr
                    165                 170                 175
Tyr Pro Met Leu Asn Val Thr Met Pro Asn Ser Asp Asp Phe Asp Lys
                180                 185                 190
Leu Tyr Ile Trp Gly Val His His Pro Ser Thr Asp Arg Glu Gln Ile
                195                 200                 205
Asn Leu Tyr Val Gln Ala Ser Gly Lys Ile Ile Val Ser Thr Lys Arg
210                 215                 220
Ser Gln Gln Thr Ile Ile Pro Asn Ile Gly Ser Arg Pro Trp Val Arg
225                 230                 235                 240
Gly Leu Ser Ser Arg Ile Ser Ile Tyr Trp Thr Ile Val Lys Pro Gly
                    245                 250                 255
Asp Ile Leu Ile Ile Asn Ser Asn Gly Asn Leu Ile Ala Pro Arg Gly
                260                 265                 270
Tyr Phe Lys Met Gln Thr Gly Lys Ser Ser Val Met Arg Ser Asp Ala
                275                 280                 285
Pro Ile Asp Thr Cys Asn Ser Glu Cys Ile Thr Pro Asn Gly Ser Ile
290                 295                 300
Pro Asn Asp Lys Pro Phe Gln Asn Val Asn Lys Ile Thr Tyr Gly Ala
305                 310                 315                 320
Cys Pro Lys Tyr Ile Lys Gln Asn Thr Leu Lys Leu Ala Thr Gly Met
                325                 330                 335
Arg Asn Ile Pro Glu Arg Gln Thr Arg Gly Ile Phe Gly Ala Ile Ala
                340                 345                 350
Gly Phe Ile Glu Asn Gly Trp Glu Gly Met Val Asn Gly Trp Tyr Gly
                355                 360                 365
Phe Arg His Gln Asn Ser Glu Gly Ile Gly Gln Ala Ala Asp Leu Lys
                370                 375                 380
Ser Thr Gln Ala Ala Ile Asn Gln Ile Asn Gly Lys Leu Asn Arg Val
385                 390                 395                 400
Ile Glu Lys Thr Asn Glu Lys Phe His Gln Ile Glu Lys Glu Phe Ser
                405                 410                 415
Glu Val Glu Gly Arg Ile Gln Asp Leu Glu Arg Tyr Val Glu Asp Thr
                420                 425                 430
Lys Ile Asp Leu Trp Ser Tyr Asn Ala Glu Leu Leu Val Ala Leu Glu
                435                 440                 445
Asn Gln His Thr Ile Asp Leu Thr Asp Ser Glu Met Asn Lys Leu Phe
450                 455                 460
Glu Lys Thr Arg Lys Gln Leu Arg Glu Asn Ala Glu Asp Met Gly Asn
```

```
                465                 470                 475                 480
Gly Cys Phe Lys Ile Tyr His Lys Cys Asp Asn Ser Cys Met Glu Ser
                    485                 490                 495
Ile Arg Asn Gly Thr Tyr Asp His Asn Glu Tyr Arg Asp Glu Ala Val
                500                 505                 510
Asn Asn Arg Phe Gln Ile Lys Ser Val Glu Leu Lys Ser Gly Tyr Lys
                515                 520                 525
Asp Trp Ile Leu Trp Ile Ser Phe Ala Ile Ser Cys Phe Leu Leu Cys
    530                 535                 540
Ala Val Trp Leu Gly Phe Ile Met Trp Ala Cys Gln Lys Gly Asn Ile
545                 550                 555                 560
Arg Cys Asn Ile Cys Ile
                565

<210> SEQ ID NO 37
<211> LENGTH: 4152
<212> TYPE: RNA
<213> ORGANISM: Artificial Sequence
<220> FEATURE:
<223> OTHER INFORMATION: encodes a PEDV S protein

<400> SEQUENCE: 37
ucacugcacu cucacuuucu caaacaccuc agcgggcugg agccggggug cucuacagca      60
gccgcugaag caggcgcagc agcagccgca gcagccgcag cagccggugg agaugcagca     120
gaacaccagc agggacacca cgaagaucag cacgaugaac acgaucagcc acacccacca     180
uggccacuug auguaggucu ccacucuguu cagccacucc agguccacca ggguguuguu     240
gauguuguag aucagggacu gcagcuccuc ggugugutuu cucagggacu cgcuucucug     300
cuccaggucg gcgaucucgc cggucagguu cagguaggug gcguugaaca cguccagggg     360
caggcugggg ccgguucugu uuggcaggga ggccaggauc ucuccaggg ucuuguucac       420
gucgauguag ucugggauca cgucggcag cuggucucug ucagguuca cguaggucac        480
cacgcaggac ucgaucugca cgaagucgcu cacgguggc uuucuuggcu cgaacauccg       540
ucuggagcuc acgaaauacu cggugcggu ugguucugc agcucguggg ugaacagcac        600
caggccgggc ucucucaggg ucagggcgau ucgucguuc acgcacaggc cggcgauggc       660
gaucacgucg augaagucgc cuggcaccag cacggugugc aggaacagca ggcccugugg      720
ggcggccugc accagggaga agaugugcuc gccgucgccg ccgcagaagc cguaucucug     780
gcucugggac uucacgcacu cguucaccuu cugcuggggcc agcuuucugg aggccugcac    840
cucggugtuac uuggucaggg ucuggccac gaaggcguuc agggcggaca gucugccggu     900
gaucagucug uccaccugca cguccggcgga caggaugucc agccuggagu agaugucguc    960
gauggagcug gagauggccu ggaaguugug cugcagcugc acggucagcu gggucagggc     1020
ggcgcccugg gaguucacca ccucccugcac cuuggucagg gcguggccca cgguuucag     1080
gcccuuggag gucuggcuga uggccucuu acgcucucg aaggcggagg ugauguugcc       1140
gauggcgcug uugaagcucu cggccagcag cugcugguuu cucugcagca cgucggucug    1200
cagggccagg uaguucaguc uggccugcac ggcguagcug aagggcaggg cggcggcgga    1260
ggugaagccg cccagcacca ugccgccgau cagggaggcg cuuacaugu gcagcuucuc    1320
ggcguccacc acgccuggca gcaccaucac gccgcuguaa uacgggcgc acaccaggug     1380
ggccacggau cugccgutugc ugcaucucuu guagccucg ccacggugc caggccguu      1440
ggucaccacc uuguugaagg cggcguccuc gaugaagcuc cucuucugca ccacucugcc    1500
```

```
gcuggcuggg ucguacacgc ucacgcccag cacguuggug aaguuguagc cgucgccguu    1560
gaaggagcug augguggcca gcugcagggc cuccucggag auggucagca ugcuguucac    1620
cuccacggac uccagccugg cgcucagcug cagggcgcuc ucgauggucu gcaggcggc     1680 gguguacugg ucagcagcu gcuugcaucu ggaguugccg uugcacacgu agguggcgca     1740
guccacggac acggggugu uguacagcug cagguacucg guucugaugc ucauggagaa     1800 guugguggg auggagaugu ugccggucac gguggggcg aucuucaccu ggccgcucug      1860
ggauggcacg uagccgaugg agccgcucuu gcacacgccg auguuggagu acaccagcac    1920
uggcucggug caguuggagc cgucguugcu ggguagaag aagccuggca gcucucuggu     1980
ggaguugaag gugcuggagg acaggcugga gaucacgccc acgaugucgu cguccacgua    2040
ggcggccugc ucgcugaagg agcagggggu cacgcuguac acggcgccgg aggucacguu    2100
cuugaaggcc agcagcuggc cgcugucgga ggguaguac acgccggcca ggaaggagcu    2160
guuggucagg gugaugaugc ccucgcccuu gaagccguag auggucuacu ggugcacac    2220 guccagggug augaagcuca cgucggucac gcccuccagg ggcuuggggg ugccggugau    2280
cagcucgccc ucgugaaacu ggaaguacag gcuggugaac uucacgccgg agccgaacuc    2340
uggguagccg aacaggucga uggugcaggc gcuggccagc aggcugguggg acacgcagaa   2400 cuugcugaag gacagguagu cguuacggga cugcagggug aagggcagu uggaguccug     2460 gcucuugcuc acguagccgu agcuguuggu cacguuguag aacaggcuga uggugaacug    2520
ccuggugucc acgcagaagc uggagaagcc guugauggug gugucggagg cgaucagguu    2580
ggcgccggag uggccgccga aggaggcgcu cacggugaug uucacgaagg aguggucguu    2640
gaaggauggc agggucacga agcugauugg cugcucgugg ucagcaggu uucuggagcu    2700 gauggggag aagccgucgu ccaggucgaa ggccaccugg cugcacuuca gcuggacac     2760 ugggucgucg caguacagga ugcgcuggau ggcggugccc ugcaccucga ucagggcguc    2820
cacgaaguug guggaggcga ugguccagaa gccgcucacg ucgucgucgg ugccgguggcc   2880 ggugaaguug auggucacgg cguccagcag gcccagguc agguagccga agccgnuuac     2940
guacacgucg ccguacuugg ugaucacgau cucucucacg gugggugca gcacggccag     3000 gaacuuguac acguugcgu uguaggauc caccuucagg aagcagauag auggcaccug      3060
gguggcgccc aguggggaugg ugaagggca gguggggg ucggagcugu uggagcacac      3120
gaagcucagg uuggugccca gggcggugug cagcacgaug cugcccuccgg ccaggaucac   3180 ggaggugucg uugauguuga aucaggggc cucggggcc cucuggcgg cggcgccguu       3240 gcacacgccg uccaugggcu gguugaagcu gaagaacugg cccaggccgu agaucuuugg    3300
gauggccagc aggcaguuca ccagcagugg cugguuggac accaccuugc cgucagcag     3360 gguggagucg uugcucagca ggaaccaguu guugaaggag aagcccucgg ggauguggcc    3420
guugcugucg guggcgaaca cguucacggc guagccgcug caguuggcgg ugcagggcuc    3480
guaguagaug ccguccucgc cggcgcuggu cacguucagc auguaguagg uuggggugua    3540
cacguacugc auggcgcagc uccgcuuguu guagcaccug guggccacuc uggaccaguc    3600
guucuucagg uagaaguggu agaucuuguc ggcgaacacg ucacucugu cguugcccca    3660 ggugaugccc accacgaugu ucuugccguc cugcauguag gcuggauggg cccuguugaa   3720
caggcaguuu cugccgguggg ucacgucguu cacgggggg ccccagggcu uguuguuggg    3780
gaacuggcag auucucagcc uggcgauggc guuggggcuug ccguuggugg ccuugugcag   3840
```

-continued

| | |
|---|---|
| guacagcugg uagccgcuug ggucgaaggg cuccuggcug augccgaucu cgaagcccug | 3900 |
| gccggcgucg auguagcuca ggaagaugcc gugcacgccg gaggcggucu ccaggccggu | 3960 |
| gccgcaguac caggagcugg aguucaugcu uggcagguag ccgcccagca ccaccacggc | 4020 |
| gggggccugc acguugaacu uggagaagaa ccgucugaag uugauugugg acuggcaucu | 4080 |
| ugugacaucc ugagggaggc ugagggugga gagcacgggg aggaagagcc agaaguaguu | 4140 |
| gagggauuuc au | 4152 |

<210> SEQ ID NO 38
<211> LENGTH: 4155
<212> TYPE: RNA
<213> ORGANISM: Artificial Sequence
<220> FEATURE:
<223> OTHER INFORMATION: encodes a PEDV S protein

<400> SEQUENCE: 38

| | |
|---|---|
| uuaucacugc acucucacuu ucucaaacac cucagcgggc uggagccggg guccucuaca | 60 |
| gcagccgcug aagcaggcgc agcagcagcc gcagcagccg cagcagccgg uggagaugca | 120 |
| gcagaacacc agcagggaca ccacgaagau cagcacgaug aacacgauca gccacaccca | 180 |
| ccauggccac uugauguagg ucuccacucu guucagccac ccagguccca ccaggguguu | 240 |
| guugauguug uagaucaggg acugcagcuc ucggugguug uuucucaggg acucgcuucu | 300 |
| cugcuccagg ucggcgaucu cgccggucag guucagguag guggcguuga acacguccag | 360 |
| gggcaggcug ggccgguuc uguuuggcag ggaggccagg aucgucca gggucuuguu | 420 |
| cacgucgaug uagucuggga ucacgucugg cagcuggucu cuggucaggu ucacguaggu | 480 |
| caccacgcag gacucgaucu gcacgaaguc gcucacggug ggcuucuug gcucgaacau | 540 |
| ccgucuggag cucacgaaau acucggggc ggugugguuc ugcagcucgu gggugaacag | 600 |
| caccaggccg ggcucucuca gggucagggc gaucucgucg uucacgcaca ggccggcgau | 660 |
| ggcgaucacg ucgaugaagu cgccuggcac cagcacggug ugcaggaaca gcaggcccug | 720 |
| ugggggcggcc ugcaccaggg agaagaugug cucgccgucg ccgccgcaga agccguaucu | 780 |
| cuggcucugg gacuucacgc acucguucac cuucugcugg gccagcuuuc uggaggccug | 840 |
| caccucggug uacuuggucca gggucugggc cacgaaggcg uucagggcgg acagucugcc | 900 |
| ggugaucagu cuguccaccu gcacgucggc ggacaggaug uccagccugg aguagaugc | 960 |
| gucgauggag cuggagaugg ccuggaaguu gucugcagc ugcacgguca gcuggggucag | 1020 |
| ggcggcgccc uggagauuca ccaccuccug caccuuggcuc agggcguggg ccacggugu | 1080 |
| caggcccuug gaggucuggc ugauggccuc cuucacgcuc ucgaaggcgg aggugauguu | 1140 |
| gccgauggcg cuguugaagc ucucggcag cagcugcugg uuucucugca gcacgucggu | 1200 |
| cugcagggcc agguaguuca gucuggccug cacggcguag cugaagggca gggcggcggc | 1260 |
| ggaggugaag ccgcccagca ccaugccgcc gaucagggag cgcuguaca ugucagcuu | 1320 |
| cucggcgucc accacgccug gcagcaccau cacgccgcug uaauacuggg cgcacaccag | 1380 |
| gucggccacg gaucugccgu ugcugcaucu cuuguagucc ucguccacgg ugcccaggcc | 1440 |
| guuggucacc accuuguuga aggcggcguc ucgaugaag cuccucuucu gcaccacucu | 1500 |
| gccgcuggcu gggucguaca cgcucacgcc cagcacguug ugaaguugu agccgucgcc | 1560 |
| guugaaggag cugauggugg ccagcugcag ggccuccucg gagauggca gcaugcuguu | 1620 |
| caccuccacg gauccagcc uggcgcucag cugcagggcg cucucgaugg ucuugcaggc | 1680 |
| ggcguguac uggucagca gcugcuugca ucuggaguug ccguugcaca cguagguggc | 1740 |

-continued

```
gcaguccacg gacacggggg uguuguacag cugcagguac ucgguucuga ugcucaugga      1800
gaaguuggug gggauggaga uguugccggu cacggugggg gcgaucuuca ccuggccgcu      1860
cugggauggc acguagccga uggagccgcu cuugcacacg ccgauguugg aguacaccag      1920
cacuggcucg gugcaguugg agccgucguu gcugugguag aagaagccug gcagcucucu      1980 ggugggaguug aaggugcugg aggacaggcu ggagaucacg cccacgaugu cgucguccac     2040
guaggcggcc ugcucgcuga aggagcaggg ggucacgcgc uacacggcgc cggaggucac      2100
guucuugaag gccagcagcu ggccgcuguc ggaggguguag uacacgccgg ccaggaagga    2160
gcuguugguc agggugauga ugcccucgcc cuugaagccg uagauggugu acuggugca      2220 cacguccagg gucaugaagc ucacgucggu cacgcccucc aggggcuuug ggugccggu      2280 gaucagcucg cccucggugc acuggaagua caggcuggug aacuucacgc cggagccgaa     2340
cucuggguag ccgaacaggu cgauggugca ggcgcuggcc agcaggcugg uggacacgca     2400
gaacuugcug aaggacaggu agucguucac ggacugcagg gugaagggggc aguuggaguc    2460 cuggcucuug cucacguagc cguagcuguu ggucacguug uagaacaggc ugauggugaa     2520
cugccuggug uccacgcaga agcuggagaa gccguugaug guggugucgg aggcgaucag     2580
guuggcgccg gaguggccgc cgaaggaggc gcucacggug auguucacga aggagugguc     2640
guugaaggau ggcaggguca cgaagcugau uggcugcucg uggcucagca gguuucugga    2700 gcugauggggg uagaagccgu cguccagguc gaaggccacc uggcugcacu ucagcuggga    2760
cacugggucg ucgcaguaca ggaugcgcug gauggcggug cccugcaccu cgaucagggc     2820
guccacgaag uugguggagg cgauggucca gaagccgcuc acgucgucgu cggugccgug    2880
gccggugaag uugaugguca cggcguccag cagccccagg ugcagguagc cgaagccguu     2940
cacguacacg ucgccguacu uggugaucac gaucucucuc acgguggggug gcagcacggc    3000 caggaacuug uacacguugc uguuguaggu guccaccuuc aggaagcagu aguauggcac     3060 cugggguggcg cccaguggga uggugaaggu ggccagguggg ggucggagc uguuggagca    3120 cacgaagcuc agguugguguc ccagggcggu gugcagcacg augcugcccu cggccaggau    3180 cacggagggug ucguugaugu ugaaucucag ggccucuggg gcccucuggg cggcggcgcc    3240
guugcacacg ccguccaugg ucugguugaa gcugaagaac uggcccaggc cguagaucuu    3300
ugggauggcc agcaggcagu ucaccagcag uggcugguug acaccaccu ugccgugcag     3360 caggguggag ucguugcuca gcaggaacca guuguugaag gagaagcccu cggggaugug    3420
gccguugcug ucgguggcga acacguucac ggcguagccg cugcaguugg cggugcaggg    3480
cucguaguag augccguccu cgccggcgcu ggucacguuc agcauguagu agguuggggu    3540
guacacguac ugcauggcgc agcuccgcuu guuguagcac cuggugggcca cucuggacca     3600 gucguucuuc agguagaagu gguagaucuu gucggcgaac acgucacucu gucguuguc      3660 ccaggugaug cccaccacga uguucuugcc guccugcaug uaggcuggga uggccuuguu     3720
gaacaggcag uuucugccgg uggucacguc guucacggug gggcccaggg ucuuguuguu    3780
ggggaacugg cagauucuca gccuggcgau ggcguuguggg uugccguugg uggccuugug    3840
cagguacagc uggguagccgc uugggucgaa gggucccugg cugaugccga ucucgaagcc    3900
cuggccggcg ucgauguagc ucaggaagau gccgugcacg ccggaggcgg ucuccaggcc    3960
ggugccgcag uaccaggagc uggaguucau gcuggcaggg uagccgccca gcaccaccac    4020
ggcgggggcc ugcacguuga acuuggagaa gaaccgucug aaguugauug uggacuggca    4080
```

```
ucuugugaca uccugaggga ggcugagggu ggagagcacg gggaggaaga gccagaagua    4140
guugagggau uucau                                                    4155

<210> SEQ ID NO 39
<211> LENGTH: 4242
<212> TYPE: RNA
<213> ORGANISM: Artificial Sequence
<220> FEATURE:
<223> OTHER INFORMATION: combination of SEQ ID NOs:14, 1, 38, 13, and 7

<400> SEQUENCE: 39
aaguuuuuua uaaugaguuu agaaugauaa uuguugacug augcaggacu ggucuugaau      60
auuuaucacu gcacucucac uuucucaaac accucagcgg gcuggagccg ggguccucua     120
cagcagccgc ugaagcaggc gcagcagcag ccgcagcagc cgcagcagcc gguggagaug     180
cagcagaaca ccagcaggga caccacgaag aucagcacga ugaacacgau cagccacacc     240
caccauggcc acugaugua ggucuccacu cuguucagcc acuccagguc caccagggug      300
uuguugaugu uguagaucag ggacugcagc uccucggugg uguuucucag ggacucgcuu     360
cucugcucca ggucggcgau cucgccgguc agguucaggu agguggcguu gaacacgucc     420
aggggcaggc uggggccggu ucuguuuggc agggaggcca ggaucucguc caggggucuuu    480 uucacgucga uguagucugg gaucacgucu ggcagcuggu cucuggucag guucacguag     540
gucaccacgc aggacucgau cugcacgaag ucgucacgg ugggcuuucu uggcucgaac      600
auccgucugg agcucacgaa auacucgggu gcggguguu ucugcagcuc gggguguaac      660
agcaccaggc cgggcucucu cagggucagg gcgaucucgu cguucacgca caggccggcg     720
auggcgauca cgucgaugaa gucgccuggc accagcacgg ugcaggaa cagcaggccc       780 ugugggggcgg ccugcaccag ggagaagaug ugcucgccgu cgccgccgca gaagccguau    840
cucuggcucu gggacuucac gcacucguuc accuucgcu gggccagcuu ucuggaggcc     900
ugcaccucgg uguacuuggu cagggucugg gccacgaagg cguucagggc ggacagucug     960
ccggugauca gucuguccac cugcacgucg gcggacagga uguccagccu ggaguagaug    1020
ucgucgaugg agcuggagau ggccuggaag uugugcugca gcugcacggu cagcugggc    1080 agggcggcgc ccugggaguu caccaccucc ugcaccuugg ucagggcgug ggccacggug    1140
uucaggcccu uggaggucug gcugauggcc uccuucacgc ucgaaaggc ggaggugaug    1200 uugccgaugg cgcuguugaa gcucucggcc agcagcugcu gguuucucug cagcacgucg    1260
gucugcaggg ccagguaguu cagucuggcc ugcacggcgu agcugaaggg cagggcggcg    1320 gcggaggug agccgcccag caccaugccg ccgaucaggg aggcgcugua caugugcagc    1380 uucucgcgu ccaccacgcc uggcagcacc aucacgccgc uguaauacug ggcgcacacc     1440
aggucggcca cggaucugcc guugcugcau cucuuguagu ccgucgccac ggugcccagg    1500 ccguuggucca ccaccuuguu gaaggcggcg uccucgauga agcuccucuu cugcaccacu   1560
cugccgcugg cugggucgua cacgcucacg cccagcacgu uggugaaguu guagccgucg    1620
ccguugaagg agcugauggu ggccagcugc agggccuccu cggagauggu cagcaugcug    1680
uucaccucca cggacuccag ccuggcgcuc agcugcaggg cgcucgaau ggucuugcag    1740 gcggcggugu acugggucag cagcugcuug caucuggagu ugccguugca cacguaggug    1800
gcgcagucca cggacacggg gguguuguac agcugcaggu acucgguucu gaugcucaug    1860
gagaaguugg uggggauggga gauguugccg gucacgguggg gggcgaucuu caccuggccg   1920 cucuggaug gcacguagcc gauggagccg cucuugcaca cgccgauguu ggaguacacc    1980
```

```
agcacuggcu cggugcaguu ggagccgucg uugcuguggu agaagaagcc uggcagcucu    2040
cugguggagu ugaaggugcu ggaggacagg cuggagauca cgcccacgau gucgucgucc    2100
acguaggcgg ccugcucgcu gaaggagcag ggggucacgc uguacacggc gccggagguc    2160
acguucuuga aggccagcag cuggccgcug ucggaggugu aguacacgcc ggccaggaag    2220
gagcuguugg ucaggguagau gaugcccucg cccuugaagc cguagauggu guacuuggug    2280
cacacgucca gggucaugaa gcucacgucg gucacgcccu ccaggggcuu uggggugccg    2340
gugaucagcu cgcccucggu gaacuggaag uacaggcugg ugaacuucac gccggagccg    2400
aacucugggu agccgaacag gucgauggug caggcgcugg ccagcaggcu gguggacacg    2460
cagaacuugc ugaaggacag guagucguuc acggacugca ggugaaggg gcaguuggag    2520 uccuggcucu ugcucacgua gccguagcug uggucacgu uguagaacag gcugauggug    2580
aacugccugg uguccacgca gaagcuggag aagccguuga ugguggaguc ggaggcgauc    2640
agguuggcgc cggaguggcc gccgaaggag gcgcucacgg ugauguucac gaaggagugg    2700
ucguugaagg auggcagggu cacgaagcug auuggcugcu cguggcucag cagguuucug    2760
gagcugaugg gguagaagcc gucguccagg ucgaaggcca ccuggcugca cuucagcugg    2820
gacacugggu cgucgcagua caggaugcgc uggauggcgg ugcccugcac cucgaucagg    2880
gcguccacga aguuggugga ggcgauggug cagaagccgc ucacgucguc ucggugccg    2940 uggccgguga aguugauggu cacggcgucc agcaggccca ggugcaggua gccgaagccg    3000
uucacguaca cgucgccgua cuuggugauc acgaucucuc ucacgguggg uggcagcacg    3060
gccaggaacu uguacacguu gcuguuguag ugguccaccu ucaggaagca guaguauggc    3120 accuggugg cgcccagugg gauggugaag guggccaggu ggggucgga gcuguuggag    3180 cacacgaagc ucagguuggu gcccagggcg gugugcagca cgaugcugcc cucggccagg    3240
aucacgaagg ugucguugau guugaaucuc agggccucug gggcccucug gcggcggcg    3300 ccguugcaca cgccguccau ggucugguug aagcugaaga acuggcccag gccguagauc    3360
uuugggaugg ccagcaggca guucaccagc aguggcuggu uggacaccac cuugccgugc    3420
agcagggugg agucguugcu cagcaggaac caguuguuga aggagaagcc cucggggaug    3480
uggccguugc ugucggaggc gaacacguuc acggcguagc cgcugcaguu ggcggugcag    3540
ggcucguagu agaugccguc cucgccggcg cuggucacgu ucagcaugua guagguuggg    3600
guguacacgu acugcauggc gcagcuccgc uuguuguagc accggauggc cacucuggac    3660
cagucguucu ucagguagaa gguguagauc uugucggcga acacggucac ucugucguug    3720
ucccagguga ugcccaccac gauguucuug ccguccugca guaggcugg gauggccuug    3780 uugaacaggc aguucugcc gguggucacg ucguucacg uggggcccag ggucuuguug    3840 uugggaacu ggcagauucu cagccuggcg augcguugu gguugccguu gguggccuug    3900
ugcagguaca gcugguagcc gcuugggucg aagggcuccu ggcugaugcc gaucucgaag    3960
cccuggccgg cgucgaugua gcucaggaag augccgugca cgccggaggc ggucuccagg    4020
ccggugccgc aguaccagga gcuggaguuc augcuuggca gguagccgcc cagcaccacc    4080
acggcggggg ccugcacguu gaacuggag aagaaccguc ugaaguugau uggaggacugg    4140 caucuuguga cauccugagg gaggcugagg guggagagca cggggaggaa gagccagaag    4200
uaguugaggg auuucauggu gcugcuggac uaccugaguc cu                       4242
```

<210> SEQ ID NO 40

<211> LENGTH: 4242
<212> TYPE: RNA
<213> ORGANISM: Artificial Sequence
<220> FEATURE:
<223> OTHER INFORMATION: combination of SEQ ID NOs:1, 38, 13, 7, and 14

<400> SEQUENCE: 40

| | | | | | |
|---|---|---|---|---|---:|
| uuuuuuauaa | ugaguuuaga | augauaauug | uugacugaug | caggacuggu | cuugaauauu | 60 |
| uaucacugca | cucucacuuu | cucaaacacc | ucagcgggcu | ggagccgggg | uccucuacag | 120 |
| cagccgcuga | agcaggcgca | gcagcagccg | cagcagccgc | agcagccggu | ggagaugcag | 180 |
| cagaacacca | gcagggacac | cacgaagauc | agcacgauga | acacgaucag | ccacacccac | 240 |
| cauggccacu | ugauguaggu | cuccacucug | uucagccacu | ccagguccac | caggguguug | 300 |
| uugauguugu | agaucaggga | cugcagcucc | ucgguggugu | uucucaggga | cucgcuucuc | 360 |
| ugcuccaggu | cggcgaucuc | gccggucagg | uucagguagg | uggcguugaa | cacguccagg | 420 |
| ggcaggcugg | ggccgguucu | guuuggcagg | gaggccagga | ucgccuccag | ggucuuguuc | 480 |
| acgucgaugu | agucugggau | cacgucuggc | agcuggucuc | uggucagguu | cacguagguc | 540 |
| accacgcagg | acucgaucug | cacgaagucg | cucacgguuc | gcuuucuugg | cucgaacauc | 600 |
| cgucuggagc | ucacgaaaua | cucgguggcg | guguggaauc | gcagcucgug | ggugaacagc | 660 |
| accaggccgg | gcucucucag | ggucagggcg | aucucgucgu | ucacgcacag | gccggcgaug | 720 |
| gcgaucacgu | cgaugaaguc | gccuggcacc | agcacgugug | caggaacag | caggcccugu | 780 |
| ggggcggccu | gcaccaggga | gaagaugugc | ucgccgucgc | cgccgcagaa | gccguaucuc | 840 |
| uggcucuggg | acuucacgca | cucguucacc | uucugcuggg | ccagcuuucu | ggaggccugc | 900 |
| accucggugu | acuuggucag | ggucugggcc | acgaaggcgu | ucagggcgga | cagucugccg | 960 |
| gugaucaguc | uguccaccug | cacgucgcg | gacaggaugu | ccagccugga | guagaugucg | 1020 |
| ucgauggagc | uggagauggc | cuggaaguug | ugcugcagcu | gcacggucag | cuggucagg | 1080 |
| gcggcgcccu | gggaguucac | caccuccgc | accuugguca | gggcgugggc | cacgguguuc | 1140 |
| aggcccuugg | aggucuggcu | gauggccucc | uucacgcucu | cgaaggcgga | ggugauguug | 1200 |
| ccgauggcgc | uguugaagcu | cucggccagc | agcugcuggu | uucucugcag | cacgucgguc | 1260 |
| ugcagggcca | gguaguucag | ucuggccugc | acggcguagc | ugaagggcag | ggcggcggcg | 1320 |
| gaggugaagc | cgcccagcac | caugccgccg | aucaggagg | cgcuguacau | gugcagcuuc | 1380 |
| ucggcgucca | ccacgccugg | cagcaccauc | acgccgcugu | aauacgggc | gcacaccagg | 1440 |
| ucggccacgg | aucugccguu | gcugcaucuc | uguagccu | cgccacggu | gccaggccg | 1500 |
| uuggucacca | ccuuguugaa | ggcggcgucc | ucgaugaagc | uccuucucug | caccacucug | 1560 |
| ccgcuggcug | ggucguacac | gcucacgccc | agcacguugg | ugaaguugua | gccgucgccg | 1620 |
| uugaaggagc | ugaugguggc | cagcugcagg | gccuccucgg | agauggucag | caugcuguuc | 1680 |
| accuccacgg | acuccagccu | ggcgcucagc | ugcagggcgc | ucucgauggu | cuugcaggcg | 1740 |
| gcgguguacu | gggucagcag | cugcuugcau | cuggaguugc | cguugcacac | guaggugggc | 1800 |
| cagccacgg | acacggggu | uuuguacagc | ugcagguacu | cgguucugau | gcucauggag | 1860 |
| aaguggugg | ggauggagau | guugccgguc | acguggggg | cgaucuucac | cuggccgcuc | 1920 |
| ugggauggca | cguagccgau | ggagccgcuc | uugcacacgc | cgauguugga | guacaccagc | 1980 |
| acuggcucgg | ugcaguugga | gccgucguug | cuguggauga | agaagccugg | cagcucucug | 2040 |
| guggaguuga | aggugcugga | ggacaggcug | gagaucacgc | ccacgaugc | gucguccacg | 2100 |
| uaggcggccu | gcucgcugaa | ggagcagggg | gucacgcugu | acacggcgcc | ggaggucacg | 2160 |

```
uucuugaagg ccagcagcug gccgcugucg gagguguagu acacgccggc caggaaggag    2220 cguugguca gggugaugau gcccucgccc uugaagccgu agauggugua cuuggugcac    2280
acguccaggg ucaugaagcu cacgucgguc acgcccucca ggggcuuugg ggugccggug    2340
aucagcucgc ccucgugaa cuggaaguac aggcugguga acuucacgcc ggagccgaac    2400 ucugggguagc cgaacagguc gauggugcag gcgcuggcca gcaggcuggu ggacacgcag    2460
aacuugcuga aggacaggua gucuucacg gacugcaggg ugaaggggca guuggagucc    2520
uggcucuugc ucacguagcc guagcuguug gucacguugu agaacaggcu gauggugaac    2580
ugccuggugu ccacgcagaa gcuggagaag ccguugaugg uggugucgga ggcgaucagg    2640
uuggcgccgg aguggccgcc gaaggaggcg cucacgguga guucacgaa ggaguggucg    2700 uugaaggaug gcaggucac gaagcugauu ggcugcucgu ggcucagcag guuucuggag    2760
cugauggggu agaagccguc guccaggucg aaggccaccu ggcugcacuu cagcugggac    2820
acugggucgu cgcaguacag gaugcgcugg auggcgguge ccugcaccuc gaucagggcg    2880
uccacgaagu uggggaggc gauguccag aagccgcuca cgucgucguc ggugccgugg    2940
ccggugaagu ugauggucac ggcguccagc aggcccaggu gcagguagcc gaagccguuc    3000
acguacacgu cgccguacuu ggugaucacg aucucucuca cgguggggugg cagcacggcc    3060 aggaacuugu acacguugcu guuguaggug uccaccuuca ggaagcagua guauggcacc    3120 ugggugggcgc ccagugggau ggugaaggug gccaggugg ggucggagcu guuggagcac    3180
acgaagcuca gguuggugcc cagggcggug ugcagcacga ugcugcccuc ggccaggauc    3240
acggaggugu cguugauguu gaaucucagg gccucgggg cccucgggc ggcggcgccg    3300 uugcacacgc cguccauggu cugguugaag cugaagaacu ggcccaggcc guagaucuuu    3360
gggauggcca gcaggcaguu caccagcagu ggcugguugg acaccaccuu gccgugcagc    3420 agggguggagu cguugcucag caggaaccag uguuugaagg agaagcccuc ggggauguga    3480
ccguugcugu cgguggcgaa cacguucacg gcguagccgc ugcaguuggc ggugcagggc    3540
ucguaguaga gccguccuc gccggcgcug ucacguuca gcauguagua gguugggggug    3600 uacacguacu gcauggcgca gcuccgcuug uuguagcacc ugguggccac ucuggaccag    3660
ucguucuuca gguagaagug guagaucuug ucggcgaaca cggucacucu gucguugucc    3720
caggugaugc ccaccacgau guucuugccg uccugcaugu aggcugggau ggccuuguug    3780
aacaggcagu uucugccggu ggucacgucg uucacggugg ggcccagggu cuuguuguug    3840
gggaacuggc agauucucag ccuggcgaug gcguugugg ugccguuggu ggccuugugc    3900
agguacagcu gguagccgcu uggggucgaag ggccuccuggc ugaugccgau cucgaagccc    3960
uggccggcgu cgauguagcu caggaagaug ccgugcacgc cggaggcggu uccaggccg    4020 gugccgcagu accaggagcu ggaguucaug cuuggcaggu agccgcccag caccaccacg    4080
gcgggggccu gcacguugaa cuuggagaag aaccgcucga guugauugu ggacuggcau    4140 cuugugacau ccugagggag gcugaggug gagagcacgg ggaggaagag ccagaaguag    4200
uugagggauu ucauggugcu gcuggacuac cugaguccua ag                     4242
```

<210> SEQ ID NO 41
<211> LENGTH: 4245
<212> TYPE: RNA
<213> ORGANISM: Artificial Sequence
<220> FEATURE:
<223> OTHER INFORMATION: combination of SEQ ID NOs:14, 1, 38, 13, 7, and 14

<400> SEQUENCE: 41

```
aaguuuuuua uaaugaguuu agaaugauaa uuguugacug augcaggacu ggucuugaau    60
auuuaucacu gcacucucac uuucucaaac accucagcgg gcuggagccg ggguccucua   120
cagcagccgc ugaagcaggc gcagcagcag ccgcagcagc cgcagcagcc gguggagaug   180
cagcagaaca ccagcaggga caccacgaag aucagcacga ugaacacgau cagccacacc   240
caccauggcc acuugaugua ggucuccacu cguucagcc acccaggu caccagggug     300
uuguugaugu uguagaucag ggacugcagc uccucggugg uguuucucag ggacucgcuu   360
cucugcucca ggucggcgau cucgccgguc agguucaggu agguggcguu gaacacgucc   420
aggggcaggc uggggccggu ucuguuuggc agggaggcca ggaucucguc caggucuug    480
uucacgucga guagucugg gaucacgucu ggcagcuggu cucggucag guucacguag    540
gucaccacgc aggacucgau cugcacgaag ucgcucacgg ugggcuuucu uggcucgaac   600
auccgucugg agcucacgaa auacucggug cggugugg ucugcagcuc guggguggaac   660
agcaccaggc cgggcucucu cagggucagg gcgaucucgu cguucacgca caggccggcg   720
auggcgauca cgucgaugaa gucgccuggc accagcacgg ugcaggaa cagcaggccc    780
ugugggggcgg ccugcaccag ggagaagaug ugcucgccgu cgccgccgca gaagccguau   840
cucuggcucu gggacuucac gcacucguuc accuucugcu gggccagcuu ucuggaggcc   900
ugcaccucgg uguacuuggu cagggucugg gccacgaagg cguucagggc ggacagucug   960
ccggugauca gucuguccac cugcacgucg cggacagga uguccagccu ggaguagaug  1020
ucgucgaugg agcuggagau ggccuggaag uugugcugca gcugcacggu cagcugguc   1080
agggcggcgc ccuggagau caccaccucc ugcaccuugg ucaggcgug ggccacgguug   1140
uucaggcccu uggaggucug gcugauggcc uccuucacgc ucucgaaggc ggagugaug    1200
uugccgaugg cgcuguugaa gcucucggcc agcagcugcu gguuucucug cagcacgucg   1260
gucucucaggg ccagguaguu cagucuggcc ugcacggcgu agcugaaggg cagggcggcg  1320
gcggaggugag agccgcccag caccauggcc ccgaucaggg aggcgcugua caugugcagc  1380
uucucggcgu ccaccacgcc uggcagcacc aucgccgcc uguaauacug ggcgcacacc   1440
ggucggcca cgggaucugcc guuggcugcau cucuguagu ccucguccac ggugcccagg   1500
ccguugguca ccaccuuguu gaaggcggcg uccucgauga agcuccucuu cugcaccacu   1560
cugccgcugg cugggucgua cacgcucacg cccagcacgu uggugaaguu guagccgucg  1620
ccguugaagg agcugauggu ggccagcugc agggccuccu cggagauggu cagcaugcug   1680
uucaccucca cggacuccag ccuggcgcuc agcugcaggg cgcucucgau ggucuugcag   1740
gcggcgugu acugggucag cagcugcuug caucuggagu ugccguugca cacguaggu    1800
gcgcaguccaa cggacacggg ggguuguac agcugcaggu acucgguucu gaugcucaug   1860
gagaaguugg uggggaugga gauguugccg ucacggugg gggcgaucuu caccuggccg   1920
cucugggaug gcacguagcc gauggagccg cucuugcaca cgccgauguu ggaguacacc   1980
agcacuggcu cggugcaguu ggagccgucg uugcuguggu agaagaagcc uggcagcucu   2040
cugguggagu ugaaggugcu ggaggacagg cuggagauca cgcccacgau gucgucgucc   2100
acguaggcgg ccugcucgcu gaaggagcag gggggcacgc uguacacggc gccggagguc   2160
acguucuuga aggccagcag cuggccgcug ucggaggugu aguacacgcc ggccaggaag   2220
gagcuguugg ucagggugau gaugcccucg cccuugaagc cguagauggu guacuuggug   2280
```

-continued

| | |
|---|---|
| cacacgucca gggucaugaa gcucacgucg gucacgcccu ccaggggcuu uggggugccg | 2340 |
| gugaucagcu cgcccucggu gaacuggaag uacaggcugg ugaacuucac gccgagccg | 2400 |
| aacucugggu agccgaacag gucgauggug caggcgcugg ccagcaggcu ggugga cacg | 2460 |
| cagaacuugc ugaaggacag guaucgucuuc acggacugca gggugaaggg gcaguuggag | 2520 |
| uccuggcucu ugcucacgua gccguagcug uuggucacgu guagaacag gcugaugug | 2580 |
| aacugccugg uguccacgca gaagcuggag aagccguuga uggugguguc ggaggcgauc | 2640 |
| agguuggcgc cggagugcc gccgaaggag gcgcucacgg ugauguucac gaaggagugg | 2700 |
| ucguugaagg auggcagggu cacgaagcug auuggcugcu cguggcucag cagguuucug | 2760 |
| gagcugaugg gguagaagcc gucguccagg ucgaaggcca ccuggcugca cuucagcugg | 2820 |
| gacacugggu cgucgcagua caggaugcgc uggauggcgg ugcccugcac cucgaucagg | 2880 |
| gcguccacga aguggugga ggcgaugguc cagaagccgc ucacgucguc gucggugccg | 2940 |
| uggccgguga aguugauggu cacggcgucc agcaggccca ggugcaggua gccgaagccg | 3000 |
| uucacguaca cgucgccgua cuggugaauc acgaucucuc ucacguggg uggcagcacg | 3060 |
| gccaggaacu guacacgu gcuguuguag guguccaccu ucaggaagca guaguauggc | 3120 |
| accugggug cgcccagugg gauggugaag guggccaggu ggggucgga gcuguuggag | 3180 |
| cacacgaagc ucagguuggu gcccagggcg gugugcagca cgaugcugcc cucggccagg | 3240 |
| aucacgagg ugucguugau guugaaucuc agggccucug ggcccucug ggcggcggcg | 3300 |
| ccguugcaca cgccguccau ggucuggug aagcugaaga acuggcccag gccguagauc | 3360 |
| uuugggaugg ccagcaggca guucaccagc aguggcuggu uggacaccac cuugccguc | 3420 |
| agcagggugg agucguugcu cagcaggaac caguuguuga aggagaagcc cucggggaug | 3480 |
| uggccguugc ugucgguggc gaacacguuc acggcguagc cgcugcaguu ggcgguggcag | 3540 |
| ggcucguagu agaugccguc cucgccggcg cuggucacgu ucagcaugua guagguuggg | 3600 |
| guguacacgu acugcauggc gcagcuccgc uguuguagc accugguggc cacucuggac | 3660 |
| cagucguucu ucagguagaa guggaugauc uugucggcga acacggucac ucugucguug | 3720 |
| ucccagguga ugcccaccac gauguucuug ccguccugca guaggcugg dauggccuug | 3780 |
| uugaacaggc aguuucugcc gguggucacg ucguucacgg uggggcccag ggucuuguug | 3840 |
| uuggggaacu ggcagauucu cagccuggcg auggcguugu gguugccguu gguggccuug | 3900 |
| ugcaggu aca gcugguagcc gcuugggucg aagggcuccu ggcugaugcc gaucucgaag | 3960 |
| cccuggccgg cgucgaugua gcucaggaag augccgucaa cgccggaggc ggucccagg | 4020 |
| ccggugccgc aguaccagga gcuggaguuc augcuuggca gguagccgcc cagcaccacc | 4080 |
| acggcggggg ccugcacguu gaacuuggag aagaaccguc ugaaguugau uguggacugg | 4140 |
| caucuuguga cauccugagg gaggcugagg guggagagca cgggggggaa gagccagaag | 4200 |
| uaguugaggg auuucauggu gcugcuggac uaccgagauc cuaag | 4245 |

<210> SEQ ID NO 42
<211> LENGTH: 4152
<212> TYPE: DNA
<213> ORGANISM: porcine epidemic diarrhea virus

<400> SEQUENCE: 42

| | |
|---|---|
| atgaaatccc tcaactactt ctggctcttc ctccccgtgc tctccaccct cagcctccct | 60 |
| caggatgtca aagatgcca gtccacaatc aacttcagac ggttcttctc caagttcaac | 120 |
| gtgcaggccc ccgccgtggt ggtgctgggc ggctacctgc caagcatgaa ctccagctcc | 180 |

```
tggtactgcg gcaccggcct ggagaccgcc tccggcgtgc acggcatctt cctgagctac      240
atcgacgccg gccagggctt cgagatcggc atcagccagg agcccttcga cccaagcggc      300
taccagctgt acctgcacaa ggccaccaac ggcaaccaca acgccatcgc caggctgaga      360
atctgccagt tccccaacaa caagaccctg gccccaccg tgaacgacgt gaccaccggc       420
agaaactgcc tgttcaacaa ggccatccca gcctacatgc aggacggcaa gaacatcgtg      480
gtgggcatca cctgggacaa cgacagagtg accgtgttcg ccgacaagat ctaccacttc      540
tacctgaaga cgactggtc cagagtggcc accaggtgct acaacaagcg gagctgcgcc       600
atgcagtacg tgtacacccc aacctactac atgctgaacg tgaccagcgc cggcgaggac      660
ggcatctact acgagccctg caccgccaac tgcagcggct acgccgtgaa cgtgttcgcc      720
accgacagca acgccacat ccccgagggc ttctccttca caactggtt cctgctgagc        780 aacgactcca ccctgctgca cggcaaggtg gtgtccaacc agccactgct ggtgaactgc      840
ctgctggcca tcccaaagat ctacggcctg ggccagttct tcagcttcaa ccagaccatg      900
gacggcgtgt gcaacggcgc cgccgcccag agggccccag aggccctgag attcaacatc      960
aacgacacct ccgtgatcct ggccgagggc agcatcgtgc tgcacaccgc cctgggcacc     1020
aacctgagct tcgtgtgctc caacagctcc gaccccacc tggccaccctt caccatccca     1080 ctgggcgcca cccaggtgcc atactactgc ttcctgaagg tggacaccta caacagcaac     1140
gtgtacaagt tcctggccgt gctgccaccc accgtgagag agatcgtgat caccaagtac     1200
ggcgacgtgt acgtgaacgg cttcggctac ctgcacctgg gcctgctgga cgccgtgacc     1260
atcaacttca ccggccacgg caccgacgac gacgtgagcg gcttctggac catcgcctcc     1320
accaacttcg tggacgccct gatcgaggtg cagggcaccg ccatccagcg catcctgtac     1380
tgcgacgacc cagtgtccca gctgaagtgc agccaggtgg ccttcgacct ggacgacggc     1440
ttctacccca tcagctccag aaacctgctg agccacgagc agccaatcag cttcgtgacc     1500
ctgccatcct tcaacgacca ctccttcgtg aacatcaccg tgagcgcctc cttcggcggc     1560
cactccggcg ccaacctgat cgcctccgac accaccatca acggcttctc cagcttctgc     1620
gtggacacca ggcagttcac catcagcctg ttctacaacg tgaccaacag ctacggctac     1680
gtgagcaaga gccaggactc caactgcccc ttcaccctgc agtccgtgaa cgactacctg     1740
tccttcagca agttctgcgt gtccaccagc ctgctggcca gcgcctgcac catcgacctg     1800
ttcggctacc agagttcgg ctccggcgtg aagttcacca gcctgtactt ccagttcacc     1860
gagggcgagc tgatcaccgg cacccccaaag cccctgagg gcgtgaccga cgtgagcttc     1920
atgaccctgg acgtgtgcac caagtacacc atctacggct tcaagggcga gggcatcatc    1980
accctgacca acagctcctt cctgccggc gtgtactaca cctccgacag cggccagctg     2040
ctggccttca gaacgtgac ctccggcgcc gtgtacagcg tgacccctg ctccttcagc       2100 gagcaggccg cctacgtgga cgacgacatc gtgggcgtga tctccagcct gtcctccagc    2160
accttcaact ccaccagaga gctgccaggc ttcttctacc acagcaacga cggctccaac    2220
tgcaccgagc cagtgctggt gtactccaac atcggcgtgt gcaagagcgg ctccatcggc    2280
tacgtgccat cccagagcgg ccaggtgaag atcgccccca ccgtgaccgg caacatctcc    2340
atccccacca acttctccat gagcatcaga accgagtacc tgcagctgta caacaccccc    2400
gtgtccgtgg actgcgccac ctacgtgtgc aacggcaact ccagatgcaa gcagctgctg    2460
acccagtaca ccgccgcctg caagaccatc gagagcgccc tgcagctgag cgccaggctg    2520
```

-continued

```
gagtccgtgg aggtgaacag catgctgacc atctccgagg aggccctgca gctggccacc    2580
atcagctcct tcaacggcga cggctacaac ttcaccaacg tgctgggcgt gagcgtgtac    2640
gacccagcca gcggcagagt ggtgcagaag aggagcttca tcgaggacgc cgccttcaac    2700
aaggtggtga ccaacggcct gggcaccgtg gacgaggact acaagagatg cagcaacggc    2760
agatccgtgg ccgacctggt gtgcgcccag tattacagcg gcgtgatggt gctgccaggc    2820
gtggtggacg ccgagaagct gcacatgtac agcgcctccc tgatcggcgg catggtgctg    2880
ggcggcttca cctccgccgc cgccctgccc ttcagctacg ccgtgcaggc cagactgaac    2940
tacctggccc tgcagaccga cgtgctgcag agaaaccagc agctgctggc cgagagcttc    3000
aacagcgcca tcggcaacat cacctccgcc ttcgagagcg tgaaggaggc catcagccag    3060
acctccaagg gcctgaacac cgtggcccac gccctgacca aggtgcagga ggtggtgaac    3120
tcccagggcg ccgccctgac ccagctgacc gtgcagctgc agcacaactt ccaggccatc    3180
tccagctcca tcgacgacat ctactccagg ctggacatcc tgtccgccga cgtgcaggtg    3240
gacagactga tcaccggcag actgtccgcc ctgaacgcct tcgtggccca gaccctgacc    3300
aagtacaccg aggtgcaggc ctccagaaag ctggcccagc agaaggtgaa cgagtgcgtg    3360
aagtcccaga gccagagata cggcttctgc ggcggcgacg gcgagcacat cttctccctg    3420
gtgcaggccg ccccacaggg cctgctgttc ctgcacaccg tgctggtgcc aggcgacttc    3480
atcgacgtga tcgccatcgc cggcctgtgc gtgaacgacg agatcgccct gacccctgaga    3540
gagcccggcc tggtgctgtt cacccacgag ctgcagaacc acaccgccac cgagtatttc    3600
gtgagctcca acggatgtt cgagccaaga aagcccaccg tgagcgactt cgtgcagatc    3660
gagtcctgcg tggtgaccta cgtgaacctg accagagacc agctgccaga cgtgatccca    3720
gactacatcg acgtgaacaa gaccctggac gagatcctgg cctccctgcc aaacagaacc    3780
ggccccagcc tgccctgga cgtgttcaac gccacctacc tgaacctgac cggcgagatc    3840
gccgacctgg agcagagaag cgagtccctg agaaacacca ccgaggagct gcagtccctg    3900
atctacaaca tcaacaacac cctggtggac ctggagtggc tgaacagagt ggagacctac    3960
atcaagtggc catggtgggt gtggctgatc gtgttcatcg tgctgatctt cgtggtgtcc    4020
ctgctggtgt tctgctgcat ctccaccggc tgctgcggct gctgcggctg ctgctgcgcc    4080
tgcttcagcg gctgctgtag aggaccccgg ctccagcccg ctgaggtgtt tgagaaagtg    4140
agagtgcagt ga                                                         4152

<210> SEQ ID NO 43
<211> LENGTH: 4155
<212> TYPE: DNA
<213> ORGANISM: porcine epidemic diarrhea virus

<400> SEQUENCE: 43
atgaaatccc tcaactactt ctggctcttc ctccccgtgc tctccaccct cagcctccct      60
caggatgtca caagatgcca gtccacaatc aacttcagac ggttcttctc caagttcaac    120
gtgcaggccc ccgccgtggt ggtgctgggc ggctacctgc caagcatgaa ctccagctcc    180
tggtactgcg caccggcct ggagaccgcc tccggcgtgc acggcatctt cctgagctac    240
atcgacgccg gccagggctt cgagatcggc atcagccagg agcccttcga cccaagcggc    300
taccagctgt acctgcacaa ggccaccaac ggcaaccaca cgccatcgc caggctgaga    360
atctgccagt tccccaacaa caagaccctg ggccccaccg tgaacgacgt gaccaccggc    420
agaaactgcc tgttcaacaa ggccatccca gcctacatgc aggacggcaa gaacatcgtg    480
```

```
gtgggcatca cctgggacaa cgacagagtg accgtgttcg ccgacaagat ctaccacttc    540
tacctgaaga acgactggtc cagagtggcc accaggtgct acaacaagcg gagctgcgcc    600
atgcagtacg tgtacacccc aacctactac atgctgaacg tgaccagcgc cggcgaggac    660
ggcatctact acgagccctg caccgccaac tgcagcggct acgccgtgaa cgtgttcgcc    720
accgacagca acggccacat ccccgagggc ttctccttca caactggttc ctgctgagc     780 aacgactcca ccctgctgca cggcaaggtg tgtccaacc agccactgct ggtgaactgc     840
ctgctggcca tcccaaagat ctacggcctg gccagttct tcagcttcaa ccagaccatg     900
gacggcgtgt gcaacggcgc cgccgcccag agggccccag aggccctgag attcaacatc    960
aacgacacct ccgtgatcct ggccgagggc agcatcgtgc tgcacaccgc cctgggcacc    1020
aacctgagct tcgtgtgctc caacagctcc gaccccacc tggccacctt caccatccca     1080
ctgggcgcca cccaggtgcc atactactgc ttcctgaagg tggacaccta acagcaac     1140 gtgtacaagt cctggccgt gctgccaccc accgtgagag agatcgtgat caccaagtac    1200
ggcgacgtgt acgtgaacgg cttcggctac ctgcacctgg gcctgctgga cgccgtgacc    1260
atcaacttca ccggccacgg caccgacgac gacgtgagcg gcttctggac catcgcctcc    1320
accaacttcg tggacgccct gatcgaggtg cagggcaccg ccatccagcg catcctgtac    1380
tgcgacgacc cagtgtccca gctgaagtgc agccaggtgg ccttcgacct ggacgacggc    1440
ttctacccca tcagctccag aaacctgctg agccacgagc agccaatcag cttcgtgacc    1500
ctgccatcct tcaacgacca ctccttcgtg aacatcaccg tgagcgcctc cttcggcggc    1560
cactccggcg ccaacctgat cgcctccgac accaccatca acggcttctc cagcttctgc    1620
gtggacacca ggcagttcac catcagcctg ttctacaacg tgaccaacag ctacggctac    1680
gtgagcaaga gccaggactc caactgcccc ttcaccctgc agtccgtgaa cgactacctg    1740
tccttcagca agttctgcgt gtccaccagc ctgctggcca cgcctgcac catcgacctg    1800 ttcggctacc agagttcgg ctccggcgtg aagttcacca gcctgtactt ccagttcacc    1860
gagggcgagc tgatcaccgg caccccaaag cccctggagg gcgtgaccga cgtgagcttc    1920
atgaccctgg acgtgtgcac caagtacacc atctacggct caagggcga gggcatcatc    1980 accctgacca acagctcctt cctggccggc gtgtactaca cctccgacag cggccagctg    2040
ctggccttca gaacgtgac ctccggcgcc gtgtacagcg tgacccctg ctccttcagc     2100 gagcaggccg cctacgtgga cgacgacatc gtgggcgtga tctccagcct gtcctccagc    2160
accttcaact ccaccagaga gctgccaggc ttcttctacc acagcaacga cggctccaac    2220
tgcaccgagc cagtgctggt gtactccaac atcggcgtgt gcaagagcgg ctccatcggc    2280
tacgtgccat cccagagcgg ccaggtgaag atcgccccca ccgtgaccgg caacatctcc    2340
atccccacca acttctccat gagcatcaga accgagtacc tgcagctgta caacaccccc    2400
gtgtccgtgg actgcgccac ctacgtgtgc aacggcaact ccagatgcaa gcagctgctg    2460
acccagtaca ccgccgcctg caagaccatc gagagcgccc tgcagctgag cgccaggctg    2520
gagtccgtgg aggtgaacag catgctgacc atctccgagg aggccctgca gctggccacc    2580
atcagctcct tcaacggcga cggctacaac ttcaccaacg tgctgggcgt gagcgtgtac    2640
gacccagcca gcggcagagt ggtgcagaag aggagcttca tcgaggacgc cgccttcaac    2700
aaggtggtga ccaacggcct gggcaccgtg gacgaggact acaagagatg cagcaacggc    2760
agatccgtgg ccgacctggt gtgcgcccag tattacagcg gcgtgatggt gctgccaggc    2820
```

```
gtggtggacg ccgagaagct gcacatgtac agcgcctccc tgatcggcgg catggtgctg      2880
ggcggcttca cctccgccgc cgccctgccc ttcagctacg ccgtgcaggc cagactgaac      2940
tacctggccc tgcagaccga cgtgctgcag agaaaccagc agctgctggc cgagagcttc      3000
aacagcgcca tcggcaacat cacctccgcc ttcgagagcg tgaaggaggc catcagccag      3060
acctccaagg gcctgaacac cgtggcccac gccctgacca aggtgcagga ggtggtgaac      3120
tcccagggcg ccgccctgac ccagctgacc gtgcagctgc agcacaactt ccaggccatc      3180
tccagctcca tcgacgacat ctactccagg ctggacatcc tgtccgccga cgtgcaggtg      3240
gacagactga tcaccggcag actgtccgcc ctgaacgcct tcgtggccca gaccctgacc      3300
aagtacaccg aggtgcaggc ctccagaaag ctggcccagc agaaggtgaa cgagtgcgtg      3360
aagtcccaga gccagagata cggcttctgc ggcggcgacg cgagcacat cttctccctg      3420
gtgcaggccg ccccacaggg cctgctgttc ctgcacaccg tgctggtgcc aggcgacttc      3480
atcgacgtga tcgccatcgc cggcctgtgc gtgaacgacg agatcgccct gaccctgaga      3540
gagcccggcc tggtgctgtt cacccacgag ctgcagaacc acaccgccac cgagtatttc      3600
gtgagctcca gacggatgtt cgagccaaga aagcccaccg tgagcgactt cgtgcagatc      3660
gagtcctgcg tggtgaccta cgtgaacctg accagagacc agctgccaga cgtgatccca      3720
gactacatcg acgtgaacaa gaccctggac gagatcctgg cctccctgcc aaacagaacc      3780
ggccccagcc tgcccctgga cgtgttcaac gccacctacc tgaacctgac cggcgagatc      3840
gccgacctgg agcagagaag cgagtccctg agaaacacca ccgaggagct gcagtccctg      3900
atctacaaca tcaacaacac cctggtggac ctggagtggc tgaacagagt gggagaccta      3960
atcaagtggc catggtgggt gtggctgatc gtgttcatcg tgctgatctt cgtggtgtcc      4020
ctgctggtgt tctgctgcat ctccaccggc tgctgcggct gctgcggctg ctgctgcgcc      4080
tgcttcagcg gctgctgtag aggacccggc tccagcccg ctgaggtgtt tgagaaagtg      4140
agagtgcagt gataa                                                      4155
```

<210> SEQ ID NO 44  
<211> LENGTH: 4245  
<212> TYPE: DNA  
<213> ORGANISM: Artificial Sequence  
<220> FEATURE:  
<223> OTHER INFORMATION: DNA reverse complement of SEQ ID NO:41

<400> SEQUENCE: 44

```
cttaggactc aggtagtcca gcagcaccat gaaatccctc aactacttct ggctcttcct        60
ccccgtgctc tccaccctca gcctccctca ggatgtcaca agatgccagt ccacaatcaa       120
cttcagacgg ttcttctcca agttcaacgt gcaggcccc gccgtggtgg tgctgggcgg       180
ctacctgcca agcatgaact ccagctcctg gtactgcggc accggcctgg agaccgcctc       240
cggcgtgcac ggcatcttcc tgagctacat cgacgccggc cagggcttcg agatcggcat       300
cagccaggag cccttcgacc caagcggcta ccagctgtac ctgcacaagg ccaccaacgg       360
caaccacaac gccatcgcca ggctgagaat ctgccagttc cccaacaaca gaccctgggg       420
ccccaccgtg aacgacgtga ccaccggcag aaactgcctg ttcaacaagg ccatcccagc       480
ctacatgcag gacggcaaga acatcgtggt gggcatcacc tgggacaacg acagagtgac       540
cgtgttcgcc gacaagatct accacttcta cctgaagaac gactggtcca gagtggccac       600
caggtgctac aacaagcgga gctgcgccat gcagtacgtg tacacccaa cctactacat       660
gctgaacgtg accagcgccg cgaggacgg catctactac gagccctgca ccgccaactg       720
```

```
cagcggctac gccgtgaacg tgttcgccac cgacagcaac ggccacatcc ccgagggctt    780
ctccttcaac aactggttcc tgctgagcaa cgactccacc ctgctgcacg gcaaggtggt    840
gtccaaccag ccactgctgg tgaactgcct gctggccatc ccaaagatct acggcctggg    900
ccagttcttc agcttcaacc agaccatgga cggcgtgtgc aacggcgccg ccgcccagag    960
ggccccagag gccctgagat caacatcaa cgacacctcc gtgatcctgg ccgagggcag   1020
catcgtgctg cacaccgccc tgggcaccaa cctgagcttc gtgtgctcca acagctccga   1080
cccccacctg gccaccttca ccatcccact gggcgccacc caggtgccat actactgctt   1140
cctgaaggtg acacctaca acagcaacgt gtacaagttc ctggccgtgc tgccacccac    1200
cgtgagagag atcgtgatca ccaagtacgg cgacgtgtac gtgaacggct cggctacct    1260 gcacctgggc ctgctggacg ccgtgaccat caacttcacc ggccacgca ccgacgacga   1320 cgtgagcggc ttctggacca tcgcctccac caacttcgtg gacgccctga tcgaggtgca   1380
gggcaccgcc atccagcgca tcctgtactg cgacgaccca gtgtcccagc tgaagtgcag   1440
ccaggtggcc ttcgacctgg acgacggctt ctaccccatc agctccagaa acctgctgag   1500
ccacgagcag ccaatcagct tcgtgaccct gccatccttc aacgaccact ccttcgtgaa   1560
catcaccgtg agcgcctcct tcggcggcca ctccggcgcc aacctgatcg cctccgacac   1620
caccatcaac ggcttctcca gcttctgcgt ggacaccagg cagttcacca tcagcctgtt   1680
ctacaacgtg accaacagct acggctacgt gagcaagagc caggactcca actgccctt   1740 cacctgcag tccgtgaacg actacctgtc cttcagcaag ttctgcgtgt ccaccagcct   1800
gctggccagc gcctgcacca tcgacctgtt cggctaccca gagttcggct ccggcgtgaa   1860
gttcaccagc ctgtacttcc agttcaccga gggcgagctg atcaccggca ccccaaagcc   1920
cctggagggc gtgaccgacg tgagcttcat gaccctggac gtgtgcacca gtacaccat   1980 ctacggcttc aagggcgagg gcatcatcac cctgaccaac agctccttcc tggccggcgt   2040
gtactacacc tccgacagcg ccagctgct ggccttcaag aacgtgacct ccggcgccgt   2100
gtacagcgtg accccctgct ccttcagcga gcaggccgcc tacgtggacg acgacatcgt   2160
gggcgtgatc tccagcctgt cctccagcac cttcaactcc accagagagc tgccaggctt   2220
cttctaccac agcaacgacg gctccaactg caccgagcca gtgctggtgt actccaacat   2280
cggcgtgtgc aagagcggct ccatcggcta cgtgccatcc cagagcggcc aggtgaagat   2340 cgccccacc gtgaccggca acatctccat ccccaccaac ttctccatga gcatcagaac   2400
cgagtacctg cagctgtaca acaccccgt gtccgtggac tgcgccacct acgtgtgcaa   2460
cggcaactcc agatgcaagc agctgctgac ccagtacacc gccgcctgca gaccatcga   2520 gagcgccctg cagctgagcg ccaggctgga gtccgtggag gtgaacagca tgctgaccat   2580
ctccgaggag gccctgcagc tggccaccat cagctccttc aacggcgacg gctacaactt   2640
caccaacgtg ctgggcgtga gcgtgtacga cccagccagc ggcagagtgg tgcagaagag   2700
gagcttcatc gaggacgccg ccttcaacaa ggtggtgacc aacggcctgg caccgtgga   2760 cgaggactac aagagatgca gcaacggcag atcgtggcc gacctggtgt gcgcccagta   2820
ttacagcggc gtgatggtgc tgccaggcgt ggtggacgcc gagaagctgc acatgtacag   2880
cgcctccctg atcggcggca tggtgctggg cggcttcacc tccgccgccg ccctgccctt   2940
cagctacgcc gtgcaggcca gactgaacta cctggccctg cagaccgacg tgctgcagag   3000
aaaccagcag ctgctggccg agagcttcaa cagcgccatc ggcaacatca cctccgcctt   3060
```

-continued

```
cgagagcgtg aaggaggcca tcagccagac ctccaagggc ctgaacaccg tggcccacgc    3120
cctgaccaag gtgcaggagg tggtgaactc ccagggcgcc gccctgaccc agctgaccgt    3180
gcagctgcag cacaacttcc aggccatctc cagctccatc gacgacatct actccaggct    3240
ggacatcctg tccgccgacg tgcaggtgga cagactgatc accggcagac tgtccgccct    3300
gaacgccttc gtggcccaga ccctgaccaa gtacaccgag gtgcaggcct ccagaaagct    3360
ggcccagcag aaggtgaacg agtgcgtgaa gtcccgagc cagagatacg gcttctgcgg    3420
cggcgacggc gagcacatct ctcccctggt gcaggccgcc cacagggcc tgctgttcct    3480 gcacaccgtg ctggtgccag gcgacttcat cgacgtgatc gccatcgccg gcctgtgcgt    3540
gaacgacgag atcgccctga ccctgagaga gcccggcctg gtgctgttca cccacgagct    3600
gcagaaccac accgccaccg agtatttcgt gagctccaga cggatgttcg agccaagaaa    3660
gcccaccgtg agcgacttcg tgcagatcga gtcctgcgtg gtgacctacg tgaacctgac    3720
cagagaccag ctgccagacg tgatcccaga ctacatcgac gtgaacaaga ccctggacga    3780
gatcctggcc tccctgccaa acagaaccgg ccccagcctg cccctggacg tgttcaacgc    3840
cacctacctg aacctgaccg gcgagatcgc cgacctggag cagagaagcg agtccctgag    3900
aaacaccacc gaggagctgc agtccctgat ctacaacatc aacaacaccc tggtggacct    3960
ggagtggctg aacagagtgg agacctacat caagtggcca tggtgggtgt ggctgatcgt    4020
gttcatcgtg ctgatcttcg tggtgtccct gctggtgttc tgctgcatct ccaccggctg    4080
ctgcggctgc tgcggctgct gctgcgcctg cttcagcggc tgctgtagag accccggct    4140 ccagcccgct gaggtgtttg agaaagtgag agtgcagtga taaatattca agaccagtcc    4200
tgcatcagtc aacaattatc attctaaact cattataaaa aactt                   4245
```

<210> SEQ ID NO 45
<211> LENGTH: 1383
<212> TYPE: PRT
<213> ORGANISM: porcine epidemic diarrhea virus

<400> SEQUENCE: 45

```
Met Lys Ser Leu Asn Tyr Phe Trp Leu Phe Leu Pro Val Leu Ser Thr
1               5                   10                  15

Leu Ser Leu Pro Gln Asp Val Thr Arg Cys Gln Ser Thr Ile Asn Phe
            20                  25                  30

Arg Arg Phe Phe Ser Lys Phe Asn Val Gln Ala Pro Ala Val Val Val
        35                  40                  45

Leu Gly Gly Tyr Leu Pro Ser Met Asn Ser Ser Trp Tyr Cys Gly
    50                  55                  60

Thr Gly Leu Glu Thr Ala Ser Gly Val His Gly Ile Phe Leu Ser Tyr
65                  70                  75                  80

Ile Asp Ala Gly Gln Gly Phe Glu Ile Gly Ile Ser Gln Glu Pro Phe
                85                  90                  95

Asp Pro Ser Gly Tyr Gln Leu Tyr Leu His Lys Ala Thr Asn Gly Asn
            100                 105                 110

His Asn Ala Ile Ala Arg Leu Arg Ile Cys Gln Phe Pro Asn Asn Lys
        115                 120                 125

Thr Leu Gly Pro Thr Val Asn Asp Val Thr Gly Arg Asn Cys Leu
    130                 135                 140

Phe Asn Lys Ala Ile Pro Ala Tyr Met Gln Asp Gly Lys Asn Ile Val
145                 150                 155                 160

Val Gly Ile Thr Trp Asp Asn Asp Arg Val Thr Val Phe Ala Asp Lys
```

-continued

```
                165                 170                 175
Ile Tyr His Phe Tyr Leu Lys Asn Asp Trp Ser Arg Val Ala Thr Arg
            180                 185                 190

Cys Tyr Asn Lys Arg Ser Cys Ala Met Gln Tyr Val Tyr Thr Pro Thr
            195                 200                 205

Tyr Tyr Met Leu Asn Val Thr Ser Ala Gly Glu Asp Gly Ile Tyr Tyr
            210                 215                 220

Glu Pro Cys Thr Ala Asn Cys Ser Gly Tyr Ala Val Asn Val Phe Ala
225                 230                 235                 240

Thr Asp Ser Asn Gly His Ile Pro Glu Gly Phe Ser Phe Asn Asn Trp
            245                 250                 255

Phe Leu Leu Ser Asn Asp Ser Thr Leu Leu His Gly Lys Val Val Ser
            260                 265                 270

Asn Gln Pro Leu Leu Val Asn Cys Leu Leu Ala Ile Pro Lys Ile Tyr
            275                 280                 285

Gly Leu Gly Gln Phe Phe Ser Phe Asn Gln Thr Met Asp Gly Val Cys
            290                 295                 300

Asn Gly Ala Ala Ala Gln Arg Ala Pro Glu Ala Leu Arg Phe Asn Ile
305                 310                 315                 320

Asn Asp Thr Ser Val Ile Leu Ala Glu Gly Ser Ile Val Leu His Thr
            325                 330                 335

Ala Leu Gly Thr Asn Leu Ser Phe Val Cys Ser Asn Ser Ser Asp Pro
            340                 345                 350

His Leu Ala Thr Phe Thr Ile Pro Leu Gly Ala Thr Gln Val Pro Tyr
            355                 360                 365

Tyr Cys Phe Leu Lys Val Asp Thr Tyr Asn Ser Asn Val Tyr Lys Phe
            370                 375                 380

Leu Ala Val Leu Pro Pro Thr Val Arg Glu Ile Val Ile Thr Lys Tyr
385                 390                 395                 400

Gly Asp Val Tyr Val Asn Gly Phe Gly Tyr Leu His Leu Gly Leu Leu
            405                 410                 415

Asp Ala Val Thr Ile Asn Phe Thr Gly His Gly Thr Asp Asp Asp Val
            420                 425                 430

Ser Gly Phe Trp Thr Ile Ala Ser Thr Asn Phe Val Asp Ala Leu Ile
            435                 440                 445

Glu Val Gln Gly Thr Ala Ile Gln Arg Ile Leu Tyr Cys Asp Asp Pro
            450                 455                 460

Val Ser Gln Leu Lys Cys Ser Gln Val Ala Phe Asp Leu Asp Asp Gly
465                 470                 475                 480

Phe Tyr Pro Ile Ser Ser Arg Asn Leu Leu Ser His Glu Gln Pro Ile
            485                 490                 495

Ser Phe Val Thr Leu Pro Ser Phe Asn Asp His Ser Phe Val Asn Ile
            500                 505                 510

Thr Val Ser Ala Ser Phe Gly Gly His Ser Gly Ala Asn Leu Ile Ala
            515                 520                 525

Ser Asp Thr Thr Ile Asn Gly Phe Ser Ser Phe Cys Val Asp Thr Arg
            530                 535                 540

Gln Phe Thr Ile Ser Leu Phe Tyr Asn Val Thr Asn Ser Tyr Gly Tyr
545                 550                 555                 560

Val Ser Lys Ser Gln Asp Ser Asn Cys Pro Phe Thr Leu Gln Ser Val
            565                 570                 575

Asn Asp Tyr Leu Ser Phe Ser Lys Phe Cys Val Ser Thr Ser Leu Leu
            580                 585                 590
```

-continued

```
Ala Ser Ala Cys Thr Ile Asp Leu Phe Gly Tyr Pro Glu Phe Gly Ser
            595                 600                 605

Gly Val Lys Phe Thr Ser Leu Tyr Phe Gln Phe Thr Glu Gly Glu Leu
            610                 615                 620

Ile Thr Gly Thr Pro Lys Pro Leu Glu Gly Val Thr Asp Val Ser Phe
625                 630                 635                 640

Met Thr Leu Asp Val Cys Thr Lys Tyr Thr Ile Tyr Gly Phe Lys Gly
            645                 650                 655

Glu Gly Ile Ile Thr Leu Thr Asn Ser Ser Phe Leu Ala Gly Val Tyr
            660                 665                 670

Tyr Thr Ser Asp Ser Gly Gln Leu Leu Ala Phe Lys Asn Val Thr Ser
            675                 680                 685

Gly Ala Val Tyr Ser Val Thr Pro Cys Ser Phe Ser Glu Gln Ala Ala
            690                 695                 700

Tyr Val Asp Asp Asp Ile Val Gly Val Ile Ser Ser Leu Ser Ser Ser
705                 710                 715                 720

Thr Phe Asn Ser Thr Arg Glu Leu Pro Gly Phe Phe Tyr His Ser Asn
            725                 730                 735

Asp Gly Ser Asn Cys Thr Glu Pro Val Leu Val Tyr Ser Asn Ile Gly
            740                 745                 750

Val Cys Lys Ser Gly Ser Ile Gly Tyr Val Pro Ser Gln Ser Gly Gln
            755                 760                 765

Val Lys Ile Ala Pro Thr Val Thr Gly Asn Ile Ser Ile Pro Thr Asn
            770                 775                 780

Phe Ser Met Ser Ile Arg Thr Glu Tyr Leu Gln Leu Tyr Asn Thr Pro
785                 790                 795                 800

Val Ser Val Asp Cys Ala Thr Tyr Val Cys Asn Gly Asn Ser Arg Cys
            805                 810                 815

Lys Gln Leu Leu Thr Gln Tyr Thr Ala Ala Cys Lys Thr Ile Glu Ser
            820                 825                 830

Ala Leu Gln Leu Ser Ala Arg Leu Glu Ser Val Glu Val Asn Ser Met
            835                 840                 845

Leu Thr Ile Ser Glu Glu Ala Leu Gln Leu Ala Thr Ile Ser Ser Phe
            850                 855                 860

Asn Gly Asp Gly Tyr Asn Phe Thr Asn Val Leu Gly Val Ser Val Tyr
865                 870                 875                 880

Asp Pro Ala Ser Gly Arg Val Val Gln Lys Arg Ser Phe Ile Glu Asp
            885                 890                 895

Leu Leu Phe Asn Lys Val Val Thr Asn Gly Leu Gly Thr Val Asp Glu
            900                 905                 910

Asp Tyr Lys Arg Cys Ser Asn Gly Arg Ser Val Ala Asp Leu Val Cys
            915                 920                 925

Ala Gln Tyr Tyr Ser Gly Val Met Val Leu Pro Gly Val Val Asp Ala
            930                 935                 940

Glu Lys Leu His Met Tyr Ser Ala Ser Leu Ile Gly Gly Met Val Leu
945                 950                 955                 960

Gly Gly Phe Thr Ser Ala Ala Ala Leu Pro Phe Ser Tyr Ala Val Gln
            965                 970                 975

Ala Arg Leu Asn Tyr Leu Ala Leu Gln Thr Asp Val Leu Gln Arg Asn
            980                 985                 990

Gln Gln Leu Leu Ala Glu Ser Phe  Asn Ser Ala Ile Gly  Asn Ile Thr
            995                 1000                1005
```

| Ser | Ala | Phe | Glu | Ser | Val | Lys | Glu | Ala | Ile | Ser | Gln | Thr | Ser | Lys |
|---|---|---|---|---|---|---|---|---|---|---|---|---|---|---|
| 1010 | | | | | 1015 | | | | | 1020 | | | | |

| Gly | Leu | Asn | Thr | Val | Ala | His | Ala | Leu | Thr | Lys | Val | Gln | Glu | Val |
|---|---|---|---|---|---|---|---|---|---|---|---|---|---|---|
| 1025 | | | | | 1030 | | | | | 1035 | | | | |

| Val | Asn | Ser | Gln | Gly | Ala | Ala | Leu | Thr | Gln | Leu | Thr | Val | Gln | Leu |
|---|---|---|---|---|---|---|---|---|---|---|---|---|---|---|
| 1040 | | | | | 1045 | | | | | 1050 | | | | |

| Gln | His | Asn | Phe | Gln | Ala | Ile | Ser | Ser | Ser | Ile | Asp | Asp | Ile | Tyr |
|---|---|---|---|---|---|---|---|---|---|---|---|---|---|---|
| 1055 | | | | | 1060 | | | | | 1065 | | | | |

| Ser | Arg | Leu | Asp | Ile | Leu | Ser | Ala | Asp | Val | Gln | Val | Asp | Arg | Leu |
|---|---|---|---|---|---|---|---|---|---|---|---|---|---|---|
| 1070 | | | | | 1075 | | | | | 1080 | | | | |

| Ile | Thr | Gly | Arg | Leu | Ser | Ala | Leu | Asn | Ala | Phe | Val | Ala | Gln | Thr |
|---|---|---|---|---|---|---|---|---|---|---|---|---|---|---|
| 1085 | | | | | 1090 | | | | | 1095 | | | | |

| Leu | Thr | Lys | Tyr | Thr | Glu | Val | Gln | Ala | Ser | Arg | Lys | Leu | Ala | Gln |
|---|---|---|---|---|---|---|---|---|---|---|---|---|---|---|
| 1100 | | | | | 1105 | | | | | 1110 | | | | |

| Gln | Lys | Val | Asn | Glu | Cys | Val | Lys | Ser | Gln | Ser | Gln | Arg | Tyr | Gly |
|---|---|---|---|---|---|---|---|---|---|---|---|---|---|---|
| 1115 | | | | | 1120 | | | | | 1125 | | | | |

| Phe | Cys | Gly | Gly | Asp | Gly | Glu | His | Ile | Phe | Ser | Leu | Val | Gln | Ala |
|---|---|---|---|---|---|---|---|---|---|---|---|---|---|---|
| 1130 | | | | | 1135 | | | | | 1140 | | | | |

| Ala | Pro | Gln | Gly | Leu | Leu | Phe | Leu | His | Thr | Val | Leu | Val | Pro | Gly |
|---|---|---|---|---|---|---|---|---|---|---|---|---|---|---|
| 1145 | | | | | 1150 | | | | | 1155 | | | | |

| Asp | Phe | Ile | Asp | Val | Ile | Ala | Ile | Ala | Gly | Leu | Cys | Val | Asn | Asp |
|---|---|---|---|---|---|---|---|---|---|---|---|---|---|---|
| 1160 | | | | | 1165 | | | | | 1170 | | | | |

| Glu | Ile | Ala | Leu | Thr | Leu | Arg | Glu | Pro | Gly | Leu | Val | Leu | Phe | Thr |
|---|---|---|---|---|---|---|---|---|---|---|---|---|---|---|
| 1175 | | | | | 1180 | | | | | 1185 | | | | |

| His | Glu | Leu | Gln | Asn | His | Thr | Ala | Thr | Glu | Tyr | Phe | Val | Ser | Ser |
|---|---|---|---|---|---|---|---|---|---|---|---|---|---|---|
| 1190 | | | | | 1195 | | | | | 1200 | | | | |

| Arg | Arg | Met | Phe | Glu | Pro | Arg | Lys | Pro | Thr | Val | Ser | Asp | Phe | Val |
|---|---|---|---|---|---|---|---|---|---|---|---|---|---|---|
| 1205 | | | | | 1210 | | | | | 1215 | | | | |

| Gln | Ile | Glu | Ser | Cys | Val | Val | Thr | Tyr | Val | Asn | Leu | Thr | Arg | Asp |
|---|---|---|---|---|---|---|---|---|---|---|---|---|---|---|
| 1220 | | | | | 1225 | | | | | 1230 | | | | |

| Gln | Leu | Pro | Asp | Val | Ile | Pro | Asp | Tyr | Ile | Asp | Val | Asn | Lys | Thr |
|---|---|---|---|---|---|---|---|---|---|---|---|---|---|---|
| 1235 | | | | | 1240 | | | | | 1245 | | | | |

| Leu | Asp | Glu | Ile | Leu | Ala | Ser | Leu | Pro | Asn | Arg | Thr | Gly | Pro | Ser |
|---|---|---|---|---|---|---|---|---|---|---|---|---|---|---|
| 1250 | | | | | 1255 | | | | | 1260 | | | | |

| Leu | Pro | Leu | Asp | Val | Phe | Asn | Ala | Thr | Tyr | Leu | Asn | Leu | Thr | Gly |
|---|---|---|---|---|---|---|---|---|---|---|---|---|---|---|
| 1265 | | | | | 1270 | | | | | 1275 | | | | |

| Glu | Ile | Ala | Asp | Leu | Glu | Gln | Arg | Ser | Glu | Ser | Leu | Arg | Asn | Thr |
|---|---|---|---|---|---|---|---|---|---|---|---|---|---|---|
| 1280 | | | | | 1285 | | | | | 1290 | | | | |

| Thr | Glu | Glu | Leu | Gln | Ser | Leu | Ile | Tyr | Asn | Ile | Asn | Asn | Thr | Leu |
|---|---|---|---|---|---|---|---|---|---|---|---|---|---|---|
| 1295 | | | | | 1300 | | | | | 1305 | | | | |

| Val | Asp | Leu | Glu | Trp | Leu | Asn | Arg | Val | Glu | Thr | Tyr | Ile | Lys | Trp |
|---|---|---|---|---|---|---|---|---|---|---|---|---|---|---|
| 1310 | | | | | 1315 | | | | | 1320 | | | | |

| Pro | Trp | Trp | Val | Trp | Leu | Ile | Val | Phe | Ile | Val | Leu | Ile | Phe | Val |
|---|---|---|---|---|---|---|---|---|---|---|---|---|---|---|
| 1325 | | | | | 1330 | | | | | 1335 | | | | |

| Val | Ser | Leu | Leu | Val | Phe | Cys | Cys | Ile | Ser | Thr | Gly | Cys | Cys | Gly |
|---|---|---|---|---|---|---|---|---|---|---|---|---|---|---|
| 1340 | | | | | 1345 | | | | | 1350 | | | | |

| Cys | Cys | Gly | Cys | Cys | Cys | Ala | Cys | Phe | Ser | Gly | Cys | Cys | Arg | Gly |
|---|---|---|---|---|---|---|---|---|---|---|---|---|---|---|
| 1355 | | | | | 1360 | | | | | 1365 | | | | |

| Pro | Arg | Leu | Gln | Pro | Tyr | Glu | Val | Phe | Glu | Lys | Val | His | Val | Gln |
|---|---|---|---|---|---|---|---|---|---|---|---|---|---|---|
| 1370 | | | | | 1375 | | | | | 1380 | | | | |

<210> SEQ ID NO 46
<211> LENGTH: 200
<212> TYPE: RNA

```
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(200)
<223> OTHER INFORMATION: This sequence may encompass 100-200 nucleotides

<400> SEQUENCE: 46
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa                                                 200

<210> SEQ ID NO 47
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 aataaa                                                                  6
```

PARAMYXOVIRIDAE EXPRESSION SYSTEM

SEQUENCE LISTING

The instant application contains a Sequence Listing which has been submitted electronically in ASCII format and is hereby incorporated by reference in its entirety. Said ASCII copy, created on Aug. 10, 2022, is named 01-3273-US-1_SL.txt and is 142,658 bytes in size.

BACKGROUND OF THE INVENTION

A. Field of the Invention

The present invention relates to the field of (vector) vaccines, and especially to an enhanced arrangement of nucleotide sequences for expressing an exogenous gene of interest by means of a Paramyxoviridae virus containing said exogenous gene. The present invention further concerns related expression cassettes and vectors, which are suitable to express genes of interest, especially antigen encoding sequences. The viral vectors of the present invention are useful for producing an immunogenic composition or vaccine.

B. Background and Description of the Related Art

Paramyxoviruses of the Paramyxoviridae family are negative-sense, single-stranded, RNA viruses that are responsible for many prevalent animal and human diseases. Examples of paramyxoviruses are Newcastle disease virus infecting poultry and other avian species or measles virus causing disease in human beings. These viruses currently comprise 49 species, which are divided into 7 genera, among them the genus Morbillivirus with seven species.

Canine distemper (CD) is a highly infectious, febrile disease of dogs and other. The mortality rate is high, ranging between 30 and 80 percent. Dogs surviving CD often have permanent central nerve system damage. The established etiology of CD is infection by a member of the Paramyxoviridae family, Morbillivirus genus known as CD virus (CDV). In general, Paramyxoviruses are enveloped viruses containing an 18-20 kb single stranded RNA genome of negative polarity. The genome encodes 5 to 7 structural proteins including a fusion (F) and either a hemagglutinin-neuraminidase (HN) or hemagglutinin (H) glycoprotein. The membrane glycoprotein hemagglutinin (H) is responsible for attachment of the virus to the host cell, and the fusion glycoprotein (F) causes membrane fusion between the virus and the infected cell or between the infected and adjacent uninfected cells.

The genome termini of members of Paramyxoviridae consist of extragenic regions, called the 3'-leader and 5'-trailer: the 3'-leader region contains the genome promoter, and the trailer encodes the 3' end of the antigenome, which is the full-length positive-sense replicative intermediate, which contains the antigenome promoter. Each gene starts with a conserved gene start (GS) sequence and ends with a conserved gene end (GE) sequence. Transcription begins at the 3'-leader region and proceeds in a sequential manner by a start-stop mechanism by which the individual genes are transcribed into individual, separate mRNAs. The genes are separated by non-coding intergenic sequences (IGS) that are conserved in length and sequence among the different gene junctions for some genera (Respirovirus, Morbillivirus, and Henipavirus) and are non-conserved in sequence or length for others (Rubulavirus, Avulavirus, Pneumovirus, and Metapneumovirus).

For CDV, both F and H glycoproteins are found present in the viral envelope and on the surface of infected cells. By inference from analyses with other Morbillivirus members, the CDV F and H glycoproteins appear important and are essential for CDV infection and its immunobiology. Poxvirus based recombinant CDV vaccines have been developed to protect and treat dogs (U.S. Pat. No. 5,756,102). US patent application U.S. Ser. No. 09/587,964 disclosed DNA plasmid based vaccines expressing CDV antigens.

Wang et al. (Vaccine 30: 5067-5072 (2012)) have generated a recombinant CDV vaccine strain expressing the rabies virus glycoprotein by using reverse genetics.

However, a disadvantage seen in practice is that such a virus strain, presumably mediated by homologous recombination between duplicated non-coding region sequence(s), may lose the inserted gene over time.

Thus, there is a strong need for an expression system which allows to stably insert a foreign gene into a Paramyxoviridae virus genome.

Furthermore, canine distemper virus and canine parvovirus (CPV) are two major pathogens of canids and other carnivores with a global distribution. The epidemiology of these two viruses in carnivore populations and their successful control are highly dependent on active immunization of susceptible hosts. The vaccination schemes most often comprise the usage of polyvalent vaccines containing among others attenuated live canine parvovirus and canine distemper components. However, the successful immunization is dependent on the age category, previous immune status and the presence of maternally derived immunity. There is a strong need to find improved vaccines protecting against major pathogens of canids such as canine distemper virus and canine parvovirus.

SUMMARY OF THE INVENTION

The solution to the above technical problem(s) is achieved by the description and the embodiments characterized in the claims.

Thus, the invention in its different aspects is implemented according to the claims.

The invention is based on the surprising finding that the insertion of an expression cassette, comprising a foreign gene flanked at the 5' end by a 5' non-coding region of a nucleoprotein (N) gene of a CDV virus, between the phosphoprotein (P) gene and the matrix protein (M) gene of a CDV virus genome (see FIG. 1), creates a virus vector allowing to accommodate, maintain and express the foreign gene even over long periods of time. This allows the generation of genetically stable transgene Paramyxoviridae based vectors such as CDV based vectors.

In a first aspect, the invention thus provides an expression cassette for insertion between two adjacent essential genes (1; 2) of a Paramyxoviridae virus such that the first gene (1) is located in 3' direction and the second gene (2) is located in 5' direction of the expression cassette, wherein said expression cassette comprises a first nucleotide sequence, wherein said first nucleotide sequence is a nucleotide sequence of interest, and a second nucleotide sequence flanking the 5' end of the first nucleotide sequence, wherein said second nucleotide sequence is the 5' non-coding region of a gene, wherein said gene is selected from the group consisting of the essential genes of a Paramyxoviridae virus excluding the first gene (1).

The expression cassette of the present invention is preferably an RNA molecule. Preferably, said expression cassette is an isolated expression cassette.

The expression cassette according to the invention preferably further comprises
a third nucleotide sequence flanking the 3' end of the first nucleotide sequence, wherein said third nucleotide sequence comprises or consists of the 3' non-coding region of a gene, wherein said gene is selected from the group consisting of the essential genes of a Paramyxoviridae virus excluding the second gene (2).

In a specific aspect, the present invention uses the Lederle vaccine strain of CDV (deposited at the ATCC under the accession number VR-128) as a backbone (genotype represented by GenBank Accession DQ903854.1, AY288311 or AY286480) or an at least 70%, 80%, 85%, 90%, 91%, 92%, 93%, 94%, 95%, 96%, 97%, 98%, 99% identical sequence thereof, such as from virus derived by additional passages thereof (e.g. Canine Distemper Virus, Lederle Avirulent, Catalog No. NR-3845, Biodefense and Emerging Infections Research Resources Repository, P.O. Box 4137, Manassas, Va. 20108-4137, USA).

The plasmid map in FIG. 2 exemplarily shows a DNA construct to generate a vector according to the invention.

The vector according to the invention is in particular useful for the vaccination of mammals, in particular of swine.

The present invention further concerns a vector for dual immunization against CDV and another virus, especially CDV and another canine virus such as CPV. This dual immunization vector expresses CDV antigens from the vector backbone and other canine antigens such as CPV VP2, which are inserted as transgene.

The invention thus also provides a canine distemper virus (CDV) vector comprising a heterologous RNA sequence of interest, which is preferably located between a P gene and an M gene of a CDV, and wherein said heterologous RNA sequence of interest encodes a Canine Parvovirus (CPV) VP2 protein.

Furthermore, the present invention contemplates vectors for inducing an immune response against swine influenza virus or porcine epidemic diarrhea virus in pigs, Thus, in the context of the present invention also Paramyxoviridae virus vectors are provided comprising an expression cassette with a heterologous RNA sequence, which encodes H3-subtype hemagglutinin of swine influenza virus or a Spike protein of porcine epidemic diarrhea virus.

The present invention further concerns mammalian host cells comprising such vectors and methods of generating vector vaccines using such host cells, as well as immunogenic compositions and vaccines comprising the CDV vector of the present invention.

DETAILED DESCRIPTION OF THE INVENTION

The present invention solves the problems inherent in the prior art and provides a distinct advance in the state of the art.

The present invention shows by in vitro data the investigation of CDV recombinants created in accordance with the teaching provided herein (i.e., CDV vectors) encoding VP2 proteins from either 2b or 2c CPV genotypes. The viruses showed good growth kinetics on production in Vero cells, reaching peak titres at 6 days post infection in roller bottles.

The recombinants showed strong expression characteristics of transgenes (VP2) as determined by immunofluorescence and Western Blot, which qualifies them as dual CDV-CPV vaccine candidates. In addition, such viruses were tested for genetic stability for 20 cell passages on Vero cells. Both viruses remained fully genetically stable, indicating that they are susceptible for vaccine bio-processing.

The present invention further demonstrates by in vivo results that CDV vector according to the invention replicated in swine host, targeting lymphatic cells. By sampling and testing the various organs, the virus was detected in lymph nodes, spleen or tonsils of vaccinated animals. Importantly, all sentinel animals remained sero-negative until the end of the study, indicating that the recombinant CDV viruses were not spread from animal to animal upon vaccination.

Concerning the efficacy, all animals vaccinated with CDV-VP2 seroconverted against canine parvovirus 2 (as measured by CPV-virus neutralization test). Particular increase in neutralizing antibody titres was detected after the $2^{nd}$ vaccination (see FIG. 6). The levels of neutralizing antibodies at 21 days after second immunization reached the levels of 1:40 to 1:400, which according to the literature, represents a protective titre range in a real host (canids) (Glover et al. 2012, Taguchi et al. 2011).

Furthermore, the use of a CDV vector according to the invention encoding H3-subtype hemagglutinin (H3) of swine influenza virus lead to the development of active immunity in H3N2-Maternally Derived Antibody-positive (H3N2-MDA-positive) piglets despite the presence of such passively present maternal immunity.

Further, a CDV vector according to the invention encoding Spike protein of porcine epidemic diarrhea virus (PEDV) was intranasally administered to sows, which then resulted, through antibody positive colostrum intake, in passive immunization of piglets seen by a reduced incidence or severity of the clinical signs, letality and virus shedding after a challenge with PEDV.

Generally, the present invention provides an expression cassette, which is also termed "the expression cassette of the present invention" hereinafter, for insertion between two adjacent essential genes (1; 2) of a Paramyxoviridae virus such that the first gene (1) is located in 3' direction and the second gene (2) is located in 5' direction of the expression cassette, wherein said expression cassette comprises
a first nucleotide sequence, wherein said first nucleotide sequence is a nucleotide sequence of interest, and
a second nucleotide sequence flanking the 5' end of the first nucleotide sequence, wherein said second nucleotide sequence is the 5' non-coding region of a gene, wherein said gene is selected from the group consisting of the essential genes of a Paramyxoviridae virus excluding the first gene (1), and
a third nucleotide sequence flanking the 3' end of the first nucleotide sequence, wherein said third nucleotide sequence comprises or consists of the 3' non-coding region of a gene, wherein said gene is selected from the group consisting of the essential genes of a Paramyxoviridae virus excluding the second gene (2).

Preferably, said third nucleotide sequence consists of
the 3' non-coding region of a gene selected from the group consisting of the essential genes of a Paramyxoviridae virus excluding the second gene (2), and
a sequence flanking the 5' end of said 3' non-coding region, wherein said sequence flanking the 5' end of said 3' non-coding region encodes a consensus sequence for initiation or enhancing of translation, and wherein said consensus sequence for initiation or enhancing of translation is optionally a Kozak sequence.

According to another preferred aspect, the expression cassette of the present invention consists of
said first to third nucleotide sequences, and
a further nucleotide sequence flanking the 5' end of the second nucleotide sequence or flanking the 3' end of said third nucleotide sequence, wherein said further nucleotide sequence is an intergenic sequence of a Paramyxoviridae virus.

Said two adjacent genes (1; 2) of a Paramyxoviridae virus are preferably selected from the group consisting of the essential genes of a Paramyxoviridae virus, and/or
said essential genes of a Paramyxoviridae virus are
the N, P, M, F, H and L gene of a Paramyxoviridae virus, or
the N, P, M, F, HN and L gene of a Paramyxoviridae virus, or
the N, P, M, F, G, and L gene of a Paramyxoviridae virus.

According to one exemplary embodiment, the invention provides an expression cassette for insertion between the P gene and the M gene of a Paramyxoviridae virus, wherein
said group consisting of the essential genes of a Paramyxoviridae virus excluding the first gene (1) is the group consisting of the essential genes of a Paramyxoviridae virus excluding the P gene of a Paramyxoviridae virus, and wherein said gene is optionally selected from the group consisting of the N, M, F, H and L gene of a Paramyxoviridae virus, and
said group consisting of the essential genes of a Paramyxoviridae virus excluding the second gene (2) is the group consisting of the essential genes of a Paramyxoviridae virus excluding the M gene of a Paramyxoviridae virus, and wherein said gene is optionally selected from the group consisting of the H, P, F, L and N gene of a Paramyxoviridae virus.

Preferably, said second nucleotide sequence is the 5' non-coding region of a gene selected from the essential genes of a Paramyxoviridae virus located in 3' direction of the expression cassette, excluding the 5' non-coding region of the first gene (1), and/or said third nucleotide sequence comprises or consists of the 3' non-coding region of an essential gene of a Paramyxoviridae virus located in 5' direction of the expression cassette, excluding the 3' non-coding region of the second gene (2).

According to another preferred aspect, said first nucleotide sequence of the expression cassette of the present invention is operably linked to the gene start (GS) sequence included in said third nucleotide sequence and/or to the genome promoter of a Paramyxoviridae virus.

Said first to third nucleotide sequences and said further nucleotide sequence of the expression cassette of the present invention are preferably RNA sequences, such that said first nucleotide sequence is then a first RNA sequence, said second nucleotide sequence is a second RNA sequence, said third nucleotide sequence is a third RNA sequence, and said further nucleotide sequence is a further RNA sequence.

In one example, the expression cassette of the present invention comprises
a first RNA sequence, wherein said first RNA sequence is an RNA sequence of interest, and
a second RNA sequence flanking the 5' end of the first RNA sequence, wherein said second RNA sequence is the 5' non-coding region of an N gene of a Paramyxoviridae virus, and a third RNA sequence flanking the 3' end of the first RNA sequence, wherein said third RNA sequence consists of the 3' non-coding region of a gene selected from the group consisting of hemagglutin (H) gene of a Paramyxoviridae virus, phosphoprotein (P) gene of a Paramyxoviridae virus, fusion protein (F) gene of a Paramyxoviridae virus, large polymerase protein (L) gene of a Paramyxoviridae virus, and nucleoprotein (N) gene of a Paramyxoviridae virus, and
a sequence flanking the 5' end of said 3' non-coding region, wherein said sequence flanking the 5' end of said 3' non-coding region encodes a Kozak sequence, and
optionally a further RNA sequence flanking the 5' end of the second nucleotide sequence or flanking the 3' end of said third nucleotide sequence, wherein said further nucleotide sequence is an intergenic sequence of a Paramyxoviridae virus.

For purposes of illustration, a schematic representation of an arrangement of RNA sequences as described herein, in connection with exemplary specific sequences provided hereinafter, is given in FIG. 3.

Preferably, the expression cassette of the present invention is non-naturally occurring and/or is included in the genome of an isolated Paramyxoviridae virus vector.

The Paramyxoviridae virus, as mentioned herein, is particularly a virus of the genus Morbillivirus, and wherein the virus of the genus Morbillivirus is preferably selected from the group consisting of canine distemper virus (CDV), feline morbillivirus (FeMV), and peste-des-petits-ruminants virus (PPRV), and wherein the virus of the genus Morbillivirus is most preferably a canine distemper virus (CDV). For instance, in the case that a CDV is chosen as the Paramyxoviridae virus, then the Paramyxoviridae virus vector described hereinafter is in particular a CDV vector.

According to a another aspect, the present invention furthermore relates to a Paramyxoviridae virus vector, comprising the expression cassette of the present invention, and wherein said Paramyxoviridae virus vector is also termed "the Paramyxoviridae virus vector of the present invention" herein. The Paramyxoviridae virus vector of the present invention is preferably an isolated Paramyxoviridae virus vector.

In one preferred aspect, the invention relates to said Paramyxoviridae virus vector or to the expression cassette of the present invention, wherein
said 5' non-coding region is the 5' non-coding region of an N gene of a Paramyxoviridae virus, and/or
said 3' non-coding region is the 3' non-coding region of an H gene of a Paramyxoviridae virus,
and/or wherein said expression cassette is inserted between a P gene and an M gene of a Paramyxoviridae virus.

Thus, the invention also relates to a Paramyxoviridae virus vector comprising an RNA sequence inserted between two adjacent essential genes (1; 2) of a Paramyxoviridae virus such that the first gene (1) is located in 3' ( direction and the second gene (2) is located in 5' direction of said inserted RNA sequence, and wherein said inserted RNA sequence comprises or consists of
a first RNA sequence, wherein said first RNA sequence is a nucleotide sequence of interest, and
a second RNA sequence flanking the 5' end of the first RNA sequence, wherein said second RNA sequence is the 5' non-coding region of a gene, wherein said gene is selected from the group consisting of the essential genes of a Paramyxoviridae virus excluding the first gene (1), and a third RNA sequence flanking the 3' end of the first RNA sequence, wherein said third RNA sequence comprises or consists of the 3' non-coding region of a gene, wherein said gene is selected from the group consisting of the essential genes of a Paramyxoviridae virus excluding the second gene (2).

Preferably, said first RNA sequence is operably linked to the gene start (GS) sequence included in said third RNA sequence and/or to the genome promoter of a Paramyxoviridae virus.

In accordance with a particular preferred aspect, said two adjacent genes (1; 2) of a Paramyxoviridae virus are selected from the group consisting of the essential genes of a Paramyxoviridae virus
and/or said essential genes of a Paramyxoviridae virus are
the N, P, M, F, H and L gene of a Paramyxoviridae virus, or
the N, P, M, F, HN and L gene of a Paramyxoviridae virus, or
the N, P, M, F, G, and L gene of a Paramyxoviridae virus.

According to a further preferred aspect, said third RNA sequence of the Paramyxoviridae virus vector of the present invention consists of
the 3' non-coding region of a gene selected from the group consisting of the essential genes of a Paramyxoviridae virus excluding the second gene (2), and
a sequence flanking the 5' end of said 3' non-coding region, wherein said sequence flanking the 5' end of said 3' non-coding region encodes a consensus sequence for initiation or enhancing of translation, and wherein said consensus sequence for initiation or enhancing of translation is optionally a Kozak sequence.

In one example, wherein said two adjacent essential genes (1; 2) of a Paramyxoviridae virus are the P gene and the M gene of a Paramyxoviridae virus, then
said group consisting of the essential genes of a Paramyxoviridae virus excluding the first gene (1) is the group consisting of the essential genes of a Paramyxoviridae virus excluding the P gene of a Paramyxoviridae virus, and wherein said gene is optionally selected from the group consisting of the N, M, F, H and L gene of a Paramyxoviridae virus, and
said group consisting of the essential genes of a Paramyxoviridae virus excluding the second gene (2) is the group consisting of the essential genes of a Paramyxoviridae virus excluding the M gene of a Paramyxoviridae virus, and wherein said gene is optionally selected from the group consisting of the H, P, F, L and N gene of a Paramyxoviridae virus.

In the context of the Paramyxoviridae virus vector of the present invention, preferably
said second nucleotide sequence is the 5' non-coding region of a gene, wherein the gene is selected from the essential genes of a Paramyxoviridae virus located in 3' direction of the expression cassette excluding the first gene (1), which in particular means that the 5' non-coding region of the first gene (1) is not selected, respectively, and/or
said third nucleotide sequence comprises or consists of the 3' non-coding region of a gene, wherein the gene is selected from the essential genes of a Paramyxoviridae located in 5' direction of the expression cassette excluding the second gene (2), which in particular means that the 3' non-coding region of the second gene (2) is not selected, respectively.

It is furthermore preferred, regarding the Paramyxoviridae virus vector of the present invention, that
said 5' non-coding region is a 5' non-coding region of an N gene of a Paramyxoviridae virus, and/or
said 3' non-coding region is a 3' non-coding region of an H gene of a Paramyxoviridae virus.

Preferably, the expression cassette or the Paramyxoviridae virus vector of the present invention in particular comprises
a first RNA sequence, wherein said first RNA sequence is an RNA sequence of interest, and
a second RNA sequence flanking the 5' end of the first RNA sequence, wherein said second RNA sequence is the 5' non-coding region of a nucleoprotein (N) gene of a Paramyxoviridae virus, and
a third RNA sequence flanking the 3' end of the first RNA sequence, wherein said third RNA sequence consists of
the 3' non-coding region of a H, HN, F, or L gene of a Paramyxoviridae virus, and
a sequence flanking the 5' end of said 3' non-coding region, wherein said sequence flanking the 5' end of said 3' non-coding region encodes a Kozak sequence.

According to a another preferred aspect, the Paramyxoviridae virus vector of the present invention further comprises
a fourth RNA sequence flanking the 5' end of the second RNA sequence, wherein said fourth RNA sequence is an intergenic sequence of a Paramyxoviridae virus, and/or
a fifth RNA sequence flanking the 3' end of the fourth RNA sequence, wherein said fifth RNA sequence is an intergenic sequence of a Paramyxoviridae virus.

Preferably, said third RNA sequence of the expression cassette of the present invention or of the Paramyxoviridae virus vector of the present invention comprises or consists of a 3' non-coding region of an H gene of a Paramyxoviridae virus and/or said expression cassette is preferably inserted between a P gene and an M gene of a Paramyxoviridae virus.

According to a particularly preferred aspect, the invention also relates to (A) an expression cassette of the present invention comprising
a first RNA sequence, wherein said first RNA sequence is a heterologous or exogenous RNA sequence of interest, and
a second RNA sequence flanking the 5' end of the first RNA sequence, wherein said second RNA sequence is the 5' non-coding region of an N gene of a CDV, and
a third RNA sequence flanking the 3' end of the first RNA sequence, wherein said third RNA sequence consists of
the 3' non-coding region of a H, HN, F, or L gene of a Paramyxoviridae virus, and
a sequence flanking the 5' end of said 3' non-coding region, wherein said sequence flanking the 5' end of said 3' non-coding region encodes a Kozak sequence,
and wherein said expression cassette preferably further comprises
a fourth RNA sequence flanking the 5' end of the second RNA sequence, wherein said fourth RNA sequence is an intergenic sequence of a CDV, or
a fifth RNA sequence flanking the 3' end of the third RNA sequence, wherein said fifth RNA sequence is an intergenic sequence of a CDV, and, respectively, the invention also relates to (B) a Paramyxoviridae virus vector of the present invention comprising the expression cassette of (A), wherein this vector is also termed "CDV vector of the present invention" herein.

Preferably, said first nuleic acid sequence of the expression cassette of the present invention or of the Paramyxoviridae virus vector of the present invention is operably linked to the gene start (GS) sequence included in said third RNA sequence and/or to the genome promoter of a Paramyxoviridae virus.

In the context of the expression cassette of the present invention or the Paramyxoviridae virus vector of the present invention, said Paramyxoviridae virus is preferably a CDV and said 5' non-coding region of a gene of a CDV is selected from the group consisting of the 5' non-coding region of an N gene of a CDV, wherein the 5' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:1, the 5' non-coding region of a P gene of a CDV, wherein the 5' non-coding region of a P gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:2, the 5' non-coding region of an M gene of a CDV, wherein the 5' non-coding region of an M gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:3, the 5' non-coding region of an F gene of a CDV, wherein the 5' non-coding region of an F gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:4, the 5' non-coding region of an H gene of a CDV, wherein the 5' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:5, and the 5' non-coding region of an L gene of a CDV, wherein the 5' non-coding region of an L gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:6.

Within the context of the expression cassette of the present invention or the Paramyxoviridae virus vector of the present invention, said Paramyxoviridae virus is preferably a CDV and said 3' non-coding region of a gene of a CDV is selected from the group consisting of the 3' non-coding region of an H gene of a CDV, wherein the 3' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:7, the 3' non-coding region of an N gene of a CDV, wherein the 3' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:8, the 3' non-coding region of a P gene of a CDV, wherein the 3' non-coding region of a P gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:9, the 3' non-coding region of an M gene of a CDV, wherein the 3' non-coding region of an M gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:10, the 3' non-coding region of an F gene of a CDV, wherein the 3' non-coding region of an F gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:11, and the 3' non-coding region of an L gene of a CDV, wherein the 3' non-coding region of an L gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:12.

Preferably, said second nucleotide sequence or said second RNA sequence of the expression cassette of the present invention or of the Paramyxoviridae virus vector of the present invention is the 5' non-coding region of an N gene of a CDV, and wherein said 5' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:1.

Regarding the expression cassette of the present invention or the Paramyxoviridae virus vector of the present invention, preferably said 3' non-coding region of a gene selected from the group consisting of the essential genes of a Paramyxoviridae virus excluding the second gene (2) is the 3' non-coding region of an H gene of a CDV, and wherein said 3' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:7, and/or said sequence flanking the 5' end of said 3' non-coding region sequence encodes a Kozak sequence being 5 to 8 nucleotides in length, and wherein the Kozak sequence preferably consists of or comprises an RNA sequence being at least 70%, 80%, 85%, 90%, 91%, 92%, 93%, 94%, 95%, 96%, 97%, 98%, or 99% identical with the sequence of SEQ ID NO:13.

Preferably, said intergenic sequence of the expression cassette of the present invention or of the Paramyxoviridae virus vector of the present invention is an intergenic sequence of a CDV, and wherein said intergenic sequence of a CDV preferably consists of or comprises an RNA sequence being at least 66% identical with the sequence of SEQ ID NO:14.

Preferably, said nucleotide sequence of interest, as described herein in the context of the expression cassette of the present invention or of the Paramyxoviridae virus vector of the present invention, is a gene of interest or an antigen encoding sequence, and/or said nucleotide sequence of interest is preferably non-naturally occurring and/or recombinant.

In particular, said nucleotide sequence of interest is preferably recombinant and/or heterologous and/or exogenous.

Said nucleotide sequence of interest preferably encodes an antigen from a disease-causing agent, wherein the disease-causing agent is preferably a disease-causing agent capable of infecting a companion animal, such as a canine or feline and/or any other domestic or wild carnivore, or capable of infecting a food producing animal such as swine or cattle.

According to one preferred aspect of the present invention, the Paramyxoviridae virus is a Paramyxoviridae virus capable of infecting an animal of a first biological family and the nucleotide sequence of interest encodes an antigen from a disease-causing agent capable of infecting an animal of said first biological family, and wherein said disease-causing agent is preferably different from said Paramyxoviridae virus.

Said animal of said first biological family is preferably selected from the group consisting of an animal of the family canidae, an animal of the family felidae and an animal of the family suidae, and wherein said animal of said first biological family is most preferably a canine, feline or swine such as a dog, cat or pig Optionally, said Paramyxoviridae virus capable of infecting an animal of a first biological family is a CDV and said disease-causing agent capable of infecting an animal of said first biological family is a Canine Parvovirus (CPV) or, optionally said Paramyxoviridae virus capable of infecting an animal of a first biological family is a La Piedad Michoacán Mexico virus (LPMV) and said disease-causing agent capable of infecting an animal of said first biological family is a swine influenza virus (SwIV).

As another preferred option, said Paramyxoviridae virus capable of infecting an animal of a first biological family is a La Piedad Michoacán Mexico virus (LPMV) and said disease-causing agent capable of infecting an animal of said first biological family is a porcine epidemic diarrhea virus (PEDV).

According to a particularly preferred aspect, said nucleotide sequence of interest encodes an antigen from a canine parvovirus (CPV), feline parvovirus (FPV) or swine influenza virus (SwIV).

As another preferred option, said nucleotide sequence of interest preferably encodes an antigen from a porcine epidemic diarrhea virus (PEDV).

Said nucleotide sequence of interest preferably encodes
a Protoparvovirus capsid protein, and wherein said Protoparvovirus capsid protein is preferably selected from the group consisting of Carnivore protoparvovirus 1 (CPV or FPV) capsid protein, Primate protoparvovirus 1 capsid protein, Rodent protoparvovirus 1 capsid protein, Rodent protoparvovirus 2 capsid protein, Ungulate parvovirus 1 (PPV) capsid protein, or
an influenza virus envelope protein, wherein said envelope protein is optionally hemagglutinin and/or wherein said influenza virus is optionally selected from the group consisting of influenza A virus, influenza B virus and influenza C virus, and wherein the influenza A virus is preferably selected from the group of the influenza viruses H3N2, H3N1, H1N1, H1N2, H2N1, H2N3 and H911.

As another preferred option, said nucleotide sequence of interest encodes a coronavirus Spike (S) protein, and wherein said coronavirus S protein is preferably selected from the group consisting of Alpaca coronavirus S protein, Alphacoronavirus 1 S protein, Human coronavirus 229E S protein, Human Coronavirus NL63 S protein, Porcine epidemic diarrhea virus (PEDV) S protein, Human coronavirus OC43 S protein, Human coronavirus HKU1 S protein, Murine coronavirus S protein, Severe acute respiratory syndrome-related coronavirus (SARS-CoV) S protein, Middle East respiratory syndrome-related coronavirus (MERS-CoV) S protein and Avian infectious bronchitis virus (IBV) S protein.

In particular, said nucleotide sequence of interest encodes
a Canine Parvovirus (CPV) VP2 protein, and wherein said CPV VP2 protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:35; or
an H3-subtype hemagglutinin (H3), in particular H3 of a swine influenza virus, and wherein said H3 preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:36.

As another preferred option, said nucleotide sequence of interest encodes a porcine epidemic diarrhea virus (PEDV) spike (S) protein, and wherein said PEDV S protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:45.

More preferably, said nucleotide sequence of interest encodes
a Canine Parvovirus (CPV) VP2 protein, and wherein said sequence encoding a CPV VP2 protein in particular consists of or comprises an RNA sequence being at least 70%, 80%, 85%, 90%, 91%, 92%, 93%, 94%, 95%, 96%, 97%, 98%, or 99% identical with the sequence of SEQ ID NO:15; or
an H3-subtype hemagglutinin (H3), preferably H3 of a swine influenza virus, and wherein said sequence encoding H3 preferably consists of or comprises an RNA sequence being at least 70%, 80%, 85%, 90%, 91%, 92%, 93%, 94%, 95%, 96%, 97%, 98%, or 99% identical with the sequence of SEQ ID NO:16.

As another preferred option, said nucleotide sequence of interest encodes a porcine epidemic diarrhea virus (PEDV) spike (S) protein, and wherein said sequence encoding a PEDV S protein preferably consists of or comprises an RNA sequence being at least 70%, 80%, 85%, 90%, 91%, 92%, 93%, 94%, 95%, 96%, 97%, 98%, or 99% identical with the sequence of SEQ ID NO:37 or SEQ ID NO:38.

According to another preferred aspect according to the invention, said expression cassette consists of or said Paramyxoviridae virus vector comprises
a polynucleotide having an RNA sequence being at least 70%, 80%, 85%, 90%, 91%, 92%, 93%, 94%, 95%, 96%, 97%, 98%, or 99% identical with the sequence of SEQ ID NO:17 or SEQ ID NO:18, or
a polynucleotide having an RNA sequence being at least 70%, 80%, 85%, 90%, 91%, 92%, 93%, 94%, 95%, 96%, 97%, 98%, or 99% identical with the sequence of SEQ ID NO:19 or SEQ ID NO:20.

As another preferred option, said expression cassette consists of or said Paramyxoviridae virus vector comprises a polynucleotide having an RNA sequence being at least 70%, 80%, 85%, 90%, 91%, 92%, 93%, 94%, 95%, 96%, 97%, 98%, or 99% identical with the sequence of SEQ ID NO:39 or SEQ ID NO:40.

Preferably, the Paramyxoviridae virus vector of the present invention comprises
- an RNA sequence being at least 70%, 80%, 85%, 90%, 91%, 92%, 93%, 94%, 95%, 96%, 97%, 98%, or 99% identical with the sequence of SEQ ID NO:21; or
- an RNA sequence being at least 70%, 80%, 85%, 90%, 91%, 92%, 93%, 94%, 95%, 96%, 97%, 98%, or 99% identical with the sequence of SEQ ID NO:22.

As another preferred option, the Paramyxoviridae virus vector of the present invention comprises an RNA sequence being at least 70%, 80%, 85%, 90%, 91%, 92%, 93%, 94%, 95%, 96%, 97%, 98%, or 99% identical with the sequence of SEQ ID NO:41.

According to a another preferred aspect, the Paramyxoviridae virus vector of the present invention further comprises
- a sixth RNA sequence flanking the 5' end of the fourth RNA sequence, wherein said sixth RNA sequence consists of or comprises an RNA sequence being at least 70%, 80%, 85%, 90%, 91%, 92%, 93%, 94%, 95%, 96%, 97%, 98%, or 99% identical with the sequence of SEQ ID NO:23, and/or
- a seventh RNA sequence flanking the 3' end of the fifth RNA sequence, wherein said seventh RNA sequence consists of or comprises an RNA sequence being at least 70%, 80%, 85%, 90%, 91%, 92%, 93%, 94%, 95%, 96%, 97%, 98%, or 99% identical with the sequence of SEQ ID NO:24.

The invention further provides a canine distemper virus vector, also termed "vector for dual CDV-CPV immunization" herein, wherein said vector comprises a heterologous RNA sequence of interest, wherein said heterologous RNA sequence of interest is preferably located between a P gene and an M gene of a CDV, and wherein said heterologous RNA sequence of interest encodes a Canine Parvovirus (CPV) VP2 protein, and wherein said sequence encoding a CPV VP2 protein optionally consists of or comprises an RNA sequence being at least 70%, 80%, 85%, 90%, 91%, 92%, 93%, 94%, 95%, 96%, 97%, 98%, or 99% identical with the sequence of SEQ ID NO:15, and wherein preferably said heterologous RNA sequence of interest is operably linked to a gene start (GS) sequence located in 3' direction of said heterologous RNA sequence, wherein said GS sequence is most preferably included in an exogenous 3' non-coding region of an H gene of a CDV, and/or to the genome promoter of a CDV.

As another preferred option, said heterologous RNA sequence of interest encodes a CPV VP2 protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:35.

Particularly, said heterologous RNA sequence of interest in the vector for dual CDV-CPV immunization is operably linked to
- an exogenous 3' non-coding region of an H gene of a CDV, in particular to the GS sequence included therein, wherein said exogenous 3' non-coding region of an H gene of a CDV preferably flanks the 3' end of said heterologous RNA sequence of interest encoding a CPV VP2 protein, and/or
- the genome promoter of a CDV.

The invention further provides a nucleic acid molecule, which encodes the expression cassette of the present invention or the Paramyxoviridae virus vector of the present invention, wherein said nucleic acid molecule is preferably a DNA molecule, and wherein said nucleic acid molecule is preferably an isolated nucleic acid molecule.

Additionally, the present invention provides a DNA molecule, which is also termed "the DNA molecule of the present invention" hereinafter, wherein said molecule comprises
(i) a DNA sequence encoding a polypeptide of interest,
(ii) a DNA sequence flanking the 3' end of the sequence of (i) and being at least 70%, 80%, 85%, 90%, 91%, 92%, 93%, 94%, 95%, 96%, 97%, 98%, or 99% identical with the sequence of SEQ ID NO:25,
(iii) a DNA sequence flanking the 5' end of the sequence of (i) and being at least 70%, 80%, 85%, 90%, 91%, 92%, 93%, 94%, 95%, 96%, 97%, 98%, or 99% identical with the sequence of SEQ ID NO:26, and
(iv) a DNA sequence flanking the 5' end of the sequence of (iii) and being at least 70%, 80%, 85%, 90%, 91%, 92%, 93%, 94%, 95%, 96%, 97%, 98%, or 99% identical with the sequence selected of SEQ ID NO:27.

The DNA molecule of the present invention preferably further comprises
(v) a DNA sequence flanking the 5' end of the sequence of (ii) and being at least 66% identical with the sequence of SEQ ID NO:28, and/or
(vi) a DNA sequence flanking the 3' end of the sequence of (iv) and being at least 66% identical with the sequence of SEQ ID NO:28.

Preferably, the DNA molecule of the present invention is an isolated DNA molecule.

According to another preferred aspect, the DNA molecule of the present invention further comprises
(vii) a DNA sequence flanking the 3' end of the sequence of (v) and being at least 70%, 80%, 85%, 90%, 91%, 92%, 93%, 94%, 95%, 96%, 97%, 98%, or 99% identical with the sequence of SEQ ID NO:29, and/or
(viii) a DNA sequence flanking the 5' end of the sequence of (vi) and being at least 70%, 80%, 85%, 90%, 91%, 92%, 93%, 94%, 95%, 96%, 97%, 98%, or 99% identical with the sequence of SEQ ID NO:30.

Preferably, the sequence of (i) is
- a DNA sequence encoding a Canine Parvovirus (CPV) VP2 protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:31, or
- a DNA sequence encoding an H3-subtype hemagglutinin (H3), preferably H3 of a swine influenza virus, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:32.

As another preferred option, the sequence of (i) is a DNA sequence encoding a PEDV S protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:42 or SEQ ID NO:43.

According to another preferred aspect, the DNA molecule of the present invention comprises
- a DNA sequence being at least 70%, 80%, 85%, 90%, 91%, 92%, 93%, 94%, 95%, 96%, 97%, 98%, or 99% identical with the sequence of SEQ ID NO:33, or
- a DNA sequence being at least 70%, 80%, 85%, 90%, 91%, 92%, 93%, 94%, 95%, 96%, 97%, 98%, or 99% identical with the sequence of SEQ ID NO:34.

As another preferred option, the DNA molecule of the present invention comprises a DNA sequence being at least 70%, 80%, 85%, 90%, 91%, 92%, 93%, 94%, 95%, 96%, 97%, 98%, or 99% identical with the sequence of SEQ ID NO:44.

The invention further provides a mammalian host cell containing
the expression cassette of the present invention,
the Paramyxoviridae virus vector of the present invention or the vector for dual CDV-CPV immunization described herein, or
the DNA molecule of the present invention,
and wherein said mammalian host cell is preferably an isolated mammalian host cell.

The present invention also provides
the expression cassette of the present invention,
the Paramyxoviridae virus vector of the present invention, or
the DNA molecule of the present invention
for use as a medicament, preferably as a vaccine.

Additionally, in the context of the invention, a DNA construct is provided comprising the DNA molecule of the present invention, wherein said DNA construct is in particular a DNA vector such as a plasmid. DNA vectors or plasmids into which the DNA molecule of the present invention can be inserted will be recognized by those of ordinary skill in the art. The DNA construct, as described herein, is preferably an isolated DNA construct. As used herein, the term "comprising the DNA molecule" is in particular understood to be equivalent to the term "comprising the sequence of the DNA molecule".

Further, the present invention provides an RNA transcript of the DNA construct described herein, wherein said RNA transcript is preferably an isolated RNA transcript.

The present invention also provides a cell transfected with the DNA construct described herein, wherein said cell is preferably an isolated cell.

Further, the present invention provides a cell transfected with the RNA transcript mentioned herein, wherein said cell is preferably an isolated cell.

Preferably, the cell or mammalian host cell, respectively, is a Vero cell.

Furthermore, in the context of the present invention, a method for the preparation of an infectious Paramyxoviridae virus containing a heterologous gene, in particular for preparing the Paramyxoviridae virus vector of the present invention is provided, wherein said method comprises the steps of:
a. providing a host cell expressing a heterologous RNA polymerase;
b. transfecting the host cell with the DNA construct described herein, and wherein the DNA molecule of the present invention included in the DNA construct is transcribed by the heterologous RNA polymerase, and
c. isolating the viruses produced by the cells.

Since a Paramyxoviridae virus has a negative stranded RNA genome, the presence of an RNA polymerase, preferably of T7 RNA polymerase or the RNA polymerase encoded by the Paramyxoviridae virus, in the transfected cells is required. Most preferred is the use of the T7 RNA polymerase. The presence of the RNA polymerase in the transfected cells can be provided, for instance, by co-transfection of a plasmid coding for and expressing the RNA polymerase or by penetrating the cells with RNA polymerase protein. According to the invention, in this regard, the use of transgenic cells producing RNA polymerase is particularly preferred, such as the transfection of the DNA construct into BHK-21 cells expressing T7 polymerase or into BSR-T7/5 cells. Alternatively, the cells can also be transfected with the mRNA that codes for the RNA polymerase and which is translated into the RNA polymerase when transfected into the host cells.

According to another aspect, the invention further provides the use of the Paramyxoviridae virus vector of the invention or of the cell described herein for the manufacture of an immunogenic composition or a vaccine.

In still another aspect, the present invention also provides an immunogenic composition, which is also termed "the immunogenic composition of the present invention" herein, wherein said immunogenic composition comprises
a. the Paramyxoviridae virus vector of the present invention, wherein said vector is optionally an infectious and/or attenuated virus or wherein said vector is optionally an attenuated and/or modified live virus, and
b. a recombinant protein expressed by said vector and/or a virus like particle comprising a plurality of a recombinant protein expressed by said vector, and
c. optionally a pharmaceutical- or veterinary-acceptable carrier or excipient, preferably said carrier is suitable for oral, intradermal, intramuscular or intranasal application.

Preferably, said recombinant protein expressed by the vector is
a parvovirus VP2 antigen such as CPV VP2 protein, or
an influenza virus envelope protein, wherein said envelope protein is optionally hemagglutinin such as H3.

It is in particular understood that the phrase "expressed by said vector" or "expressed by the vector", respectively, as used herein, is in particular equivalent to "expressed in a cell infected with the vector" or "expressed in a cell infected with said vector", respectively.

According to another preferred aspect, the immunogenic composition of the present invention comprises or consists of
a. any of the above mentioned vectors encoding a CPV VP2 protein, and wherein said vector is preferably a CDV vector, in particular the CDV vector of the present invention, or a vector for dual CDV-CPV immunization, as described herein, and
b. a polypeptide comprising or consisting of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, wherein said polypeptide is preferably a recombinant protein expressed by said vector,
c. and optionally a pharmaceutical- or veterinary-acceptable carrier or excipient, wherein said carrier is preferably suitable for oral, intradermal, intramuscular or intranasal application.

As another preferred option, said recombinant protein expressed by said vector is a coronavirus S protein, and wherein said coronavirus S protein is optionally a PEDV S protein, in particular comprising or consisting of an amino acid sequence being at least 70%, 80%, 85%, 90%, 91%, 92%, 93%, 94%, 95%, 96%, 97%, 98%, or 99% identical with the sequence of SEQ ID NO:45.

The invention also provides a vaccine or pharmaceutical composition, which is hereinafter also termed "the vaccine or the pharmaceutical composition of the present invention, wherein said vaccine or pharmaceutical composition comprises
a. any of the vectors described herein in the context of the present invention, and
b. a recombinant protein expressed by said vector and/or a virus like particle comprising a plurality of a recombinant protein expressed by said vector, and c. a pharmaceutical- or veterinary-acceptable carrier or excipient, wherein said carrier is preferably suitable for oral, intradermal, intramuscular or intranasal application, and
d. optionally said vaccine further comprises an adjuvant, and wherein said recombinant protein expressed by the vector is preferably
   parvovirus VP2 antigen such as CPV VP2 protein, or
   an influenza virus envelope protein, wherein said envelope protein is optionally hemagglutinin such as H3.

Preferably, the vaccine or pharmaceutical composition of the present invention comprises or consists of
a. any of the above mentioned vectors encoding a CPV VP2 protein or an influenza virus hemagglutinin, and wherein said vector is preferably a CDV vector, in particular the CDV vector of the present invention, or a vector for dual CDV-CPV immunization, as described herein, and
b. a polypeptide comprising or consisting of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, wherein said polypeptide is preferably a recombinant protein expressed by said vector, and
c. a pharmaceutical- or veterinary-acceptable carrier or excipient, preferably said carrier is suitable for oral, intradermal, intramuscular or intranasal application,
d. and optionally an adjuvant.

As another preferred option, said recombinant protein expressed by said vector, which is included in the vaccine or pharmaceutical composition of the present invention, is a coronavirus S protein, and wherein said coronavirus S protein is optionally a PEDV S protein, in particular comprising or consisting of an amino acid sequence being at least 70%, 80%, 85%, 90%, 91%, 92%, 93%, 94%, 95%, 96%, 97%, 98%, or 99% identical with the sequence of SEQ ID NO:45.

The present invention further provides a method for the preparation of an immunogenic composition or a vaccine for reducing the incidence or the severity of one or more clinical signs associated with or caused by an infection, comprising the following steps:
a. infecting a mammalian host cell with any of the vectors described herein in the context of the present invention,
b. cultivating the infected cells under suitable conditions,
c. collecting infected cell cultures,
d. optionally purifying the collected infected cell cultures of step c)
e. optionally mixing said collected infected cell culture with a pharmaceutically acceptable carrier,
and wherein the immunogenic composition or vaccine is preferably reducing the severity of one or more clinical signs associated with or caused by
   an infection with CDV and CPV, or
   an infection with an influenza virus, wherein said influenza virus is optionally selected from the group consisting of influenza A virus, influenza B virus and influenza C virus, and wherein the influenza A virus is preferably selected from the group of the influenza viruses H3N2, H3N1, H1N1, H1N2, H2N1, H2N3 and H9l1.

As another preferred option, said immunogenic composition or vaccine reduces the severity of one or more clinical signs associated with or caused by an infection with a coronavirus, wherein said coronavirus is optionally selected from the group consisting of Alpaca coronavirus, Alphacoronavirus 1, Human coronavirus 229E, Human Coronavirus NL63, Porcine epidemic diarrhea virus (PEDV), Human coronavirus OC43, Human coronavirus HKU1, Murine coronavirus, Severe acute respiratory syndrome-related coronavirus (SARS-CoV), Middle East respiratory syndrome-related coronavirus (MERS-CoV) and Avian infectious bronchitis virus (IBV).

The present invention also relates to
   the immunogenic composition of the present invention or
   the vaccine or pharmaceutical composition of the present invention
for use in a method of reducing or preventing the clinical signs or disease caused by an infection with at least one pathogen in an animal or for use in a method of treating or preventing an infection with at least one pathogen in an animal, preferably said animal is a companion animal, such as a canine or feline and/or any other domestic or wild carnivore, or a food producing animal such as swine, and wherein said infection with at least one pathogen is preferably
   an infection with CDV and/or CPV, wherein said infection is most preferably an infection with CDV and/or CPV, or
   an infection with swine influenza virus, wherein the swine influenza virus is optionally a subtype H3 influenza virus, and wherein said subtype H3 influenza virus is preferably a swine influenza virus of the subtype H3N2 or H3N1.

As another preferred option, said infection with at least one pathogen is an infection with PEDV.

In particular, the present invention also relates to the immunogenic composition or the vaccine of the present invention or the pharmaceutical composition of the present invention for use in a method for
   inducing an immune response against CPV and CDV in an animal, preferably in a canine, or
   inducing an immune response against swine influenza virus in a pig, wherein the swine influenza virus is optionally a subtype H3 influenza virus, and wherein said subtype H3 influenza virus is preferably a swine influenza virus of the subtype H3N2 or H3N1.

As another preferred option, the immunogenic composition or the vaccine of the present invention or the pharmaceutical composition of the present invention is for use in a method for inducing an immune response against PEDV in a pig, in particular in a preferably pregnant sow.

In one aspect, the immunogenic composition or the vaccine of the present invention or the pharmaceutical composition of the present invention is for use in a method of reducing or preventing the clinical signs or disease caused by an infection with a PEDV in a piglet, wherein the piglet is to be suckled by a sow to which the immunogenic composition has been adminstered, and wherein said sow is preferably a sow to which the immunogenic composition has been administered while/when said sow has been pregnant, in particular with said piglet.

According to a particular preferred aspect of the present invention, in such use the immunogenic composition or the vaccine of the present invention or the pharmaceutical composition of the present invention is to be administered mucosally, preferably intranasally, such as to said sow.

Additionally, the present invention provides a method of immunizing an animal such as a companion animal, such as a canine or feline and/or any other domestic or wild carnivore, or a food producing animal including swine against a clinical disease caused by at least one pathogen in said animal, said method comprising the step of administering to the animal the immunogenic composition of the present invention or the vaccine or pharmaceutical composition of the present invention, wherein said immunogenic composition or vaccine fails to cause clinical signs of infection but is capable of inducing an immune response that immunizes the animal against pathogenic forms of said at least one pathogen, and wherein said at least one pathogen is preferably CDV or CPV or SwIV or, most preferably, CDV and CPV.

The present invention further provides a method for inducing the production of antibodies specific for PEDV in a sow, wherein said method comprises administering the immunogenic composition of the present invention or the vaccine or pharmaceutical composition of the present invention, in particular comprising a Paramyxoviridae virus vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:45, to said sow.

Further, the present invention in particular provides a method of reducing or preventing the clinical signs or disease caused by an infection with a PEDV in a piglet, wherein said method comprises
administering the immunogenic composition of the present invention or the vaccine or pharmaceutical composition of the present invention, in particular comprising a Paramyxoviridae virus vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:45, to a sow, and
allowing said piglet to be suckled by said sow.

Preferably, said sow is a sow being pregnant, in particular with said piglet

More preferably, such method of reducing or preventing the clinical signs or disease caused by an infection with a PEDV in a piglet, comprises the steps of
administering the immunogenic composition of the present invention or the vaccine or pharmaceutical composition of the present invention, in particular comprising a Paramyxoviridae virus vector of the present invention encoding a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:45, to a sow being pregnant with said piglet,
allowing said sow to give birth to said piglet, and
allowing said piglet to be suckled by said sow.

Preferably, the immunogenic composition of the present invention or the vaccine or pharmaceutical composition of the present invention is administered to the animal intramuscularly or mucosally, such as by intranasal administration.

Most preferably in such method of reducing or preventing the clinical signs or disease caused by an infection with a PEDV in a piglet said immunogenic composition or said vaccine or pharmaceutical composition is administered mucosally, preferably intranasally, to said sow.

According to still another preferred aspect, the present invention also provides a kit for inducing an immune response against at least one pathogen in an animal or for vaccinating an animal, preferably a companion animal, such as a canine or feline and/or any other domestic or wild carnivore, or food producing animal such as swine or cattle, against a disease associated with at least one pathogen and/or reducing the incidence or the severity of one or more clinical signs associated with or caused by at least one pathogen in an animal comprising:

a) a syringe or a dispenser capable of administering a vaccine to said animal; and
b) the immunogenic composition of the present invention or the vaccine or pharmaceutical composition of the present invention, and
c) optionally an instruction leaflet,
wherein said at least one pathogen is preferably CDV or CPV or SwIV or PEDV, and wherein said at least one pathogen is most preferably CDV and CPV.

Definitions

Unless defined otherwise, all technical and scientific terms used herein have the same meaning as is commonly understood by one of skill in the art to which this invention belongs at the time of filing. The meaning and scope of terms should be clear; however, in the event of any latent ambiguity, definitions provided herein take precedent over any dictionary or extrinsic definition. Further, unless otherwise required by context, singular terms shall include pluralities and plural terms shall include the singular. Herein, the use of "or" means "and/or" unless stated otherwise. Furthermore, the use of the term "including", as well as other forms such as "includes" and "included" is not limiting. All patents and publications referred to herein are incorporated by reference herein.

The practice of the present invention will employ, unless otherwise indicated, conventional techniques of virology, molecular biology, microbiology, recombinant DNA technology, protein chemistry and immunology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); Protein purification methods—a practical approach (E. L. V. Harris and S. Angal, eds., IRL Press at Oxford University Press); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting. It must be noted that, as used in this specification and the appended claims, the singular forms "a", "an" and "the" include plural referents unless the content clearly dictates otherwise. Thus, for example, reference to "an antigen" includes a mixture of two or more antigens, reference to "an excipient" includes mixtures of two or more excipients, and the like.

Paramyxoviridae Definitions

It is in particular understood that the term "Paramyxoviridae virus", as used herein, is equivalent to the term "paramyxovirus", as frequently used in the context of viruses of the family Paramyxoviridae.

The term "5' non-coding region of an N gene of a Paramyxoviridae virus", as used herein, in particular relates to an RNA sequence of an expressable N gene of a preferably infectious Paramyxoviridae virus, said RNA sequence flanking the 5' end of the coding sequence (i.e. the 5' end of the RNA triplet complementary to the stop codon) and comprising the gene end sequence of said gene. Thus, more particular, the "5' non-coding region sequence", as mentioned herein, is an RNA sequence identical to the entire 5' non-coding sequence of an expressable N gene of a preferably infectious Paramyxoviridae virus. Still more particular, the "5' non-coding region", as mentioned herein, is an RNA sequence identical to the non-coding sequence of an N gene of a Paramyxoviridae virus, wherein said non-coding sequence is flanked by (a) the coding sequence and (b) the intergenic sequence connecting said N gene with the P gene.

The term "3' non-coding region" of a specific gene (e.g. H gene) of a Paramyxoviridae virus, as used herein, in particular relates to an RNA sequence of an expressable specific gene (e.g. H gene) of a preferably infectious Paramyxoviridae virus, said RNA sequence flanking the 3' end of the coding sequence (i.e. the 3' end of the RNA triplet complementary to the start codon) and comprising the gene start sequence of said gene. Thus, more particular, the "3' non-coding region sequence", as mentioned herein, is an RNA sequence identical to the entire 3' non-coding sequence of an expressable specific gene (e.g. H gene) of a preferably infectious Paramyxoviridae virus. Still more particular, the "3' non-coding region", as mentioned herein, is an RNA sequence identical to the non-coding sequence of a specific gene (e.g. H, gene) of a Paramyxoviridae virus, wherein said non-coding sequence is flanked by (a) the coding sequence and (b) the intergenic sequence connecting said gene with the next gene in 3' direction.

As used herein, the term "intergenic region" in particular refers to the RNA sequence connecting the 5' end of a gene of a Paramyxoviridae virus with the 3' start of the adjacent gene in 5' direction of a Paramyxoviridae virus.

The term "gene start sequence", as used herein, is in particular equivalent to the term "gene start signal".

As used herein, it is understood that the term "genome promoter of a Paramyxoviridae virus" is equivalent to the term "genome leader sequence of a Paramyxoviridae virus", and that the term "genome promoter of a CDV" is equivalent to the term "genome leader sequence of a CDV", respectively.

Molecular Biology Definitions

The phrase "sequence flanking the 5' end of" as described herein is in particular equivalent to the phrase "sequence covalently linked with the 5' end of" or, respectively, with the phrase "sequence, wherein the 3' terminal nucleotide thereof is covalently linked with the 5' terminal nucleotide of", and wherein it is particularly understood that said two terminal nucleotides are linked covalently between the phosphate group attached to the 5' carbon of the pentose and the 3' carbon atom of the adjacent pentose.

The phrase "sequence flanking the 3' end of" as described herein is in particular equivalent to the phrase "sequence covalently linked with the 3' end of" or, respectively, to the phrase "sequence, wherein the 5' terminal nucleotide thereof" is covalently linked with the 3' terminal nucleotide of", and wherein it is particularly understood that said two terminal nucleotides are linked covalently between the 3' carbon atom of the pentose and the phosphate group attached to the 5' carbon of the adjacent pentose.

It is understood, that the term "Kozak sequence" as used in the context of the present invention in particular relates to a nucleotide sequence which codes for an mRNA sequence taking part in the recognition of a translational start site by the ribosome. Preferably, an RNA sequence encoding a Kozak sequence in the context of the present invention is an RNA sequence which may be transcribed into a sequence of an mRNA molecule flanking the 5' end of the start codon (AUG) therein and playing a role in the initiation of the translation process.

The term "vector" as it is known in the art refers to a polynucleotide construct, typically a plasmid or a bacterial artificial chromosome, used to transmit genetic material to a host cell. Vectors can be, for example, bacteria, viruses, phages, bacterial artificial chromosomes, cosmids, or plasmids. A vector as used herein can be composed of or contain either DNA or RNA. In some embodiments, a vector is composed of DNA. In some embodiments a vector is an infectious virus. Such a viral vector contains a viral genome which was manipulated in a way that it carries a foreign gene which has no function in the replication of the viral vector neither in cell culture nor in a host animal. According to specific aspects of the present disclosure a vector may be used for various aspects such as mere transmission of genetic material, for the transfection of host cells or organisms, for use as vaccines, e.g. DNA vaccines or for gene expression purposes. Gene expression is a term describing the biosynthesis of a protein in a cell as directed by a specific polynucleotide sequence called gene. In a specific aspect a vector may be an "expression vector", which is a vector that is capable of directing the expression of a protein encoded by one or more genes carried by the vector when it is present in the appropriate environment.

Vectors and methods for making and/or using vectors (or recombinants) for expression can be by or analogous to the methods disclosed in: U.S. Pat. Nos. 4,603,112, 4,769,330, 5,174,993, 5,505,941, 5,338,683, 5,494,807, 4,722,848, 5,942,235, 5,364,773, 5,762,938, 5,770,212, 5,942,235, 382, 425, PCT publications WO 94/16716, WO 96/39491, WO 95/30018; Paoletti, "Applications of pox virus vectors to vaccination: An update, "PNAS USA 93: 11349-11353, October 1996; Moss, "Genetically engineered poxviruses for recombinant gene expression, vaccination, and safety," PNAS USA 93: 11341-11348, October 1996; Smith et al., U.S. Pat. No. 4,745,051(recombinant baculovirus); Richardson, C. D. (Editor), Methods in Molecular Biology 39, "Baculovirus Expression Protocols" (1995 Humana Press Inc.); Smith et al., "Production of Human Beta Interferon in Insect Cells Infected with a Baculovirus Expression Vector", Molecular and Cellular Biology, December, 1983, Vol. 3, No. 12, p. 2156-2165; Pennock et al., "Strong and Regulated Expression of *Escherichia coli* B-Galactosidase in Infect Cells with a Baculovirus vector, "Molecular and Cellular Biology March 1984, Vol. 4, No. 3, p. 406; EPAO 370 573; U.S. application No. 920,197, filed Oct. 16, 1986; EP Patent publication No. 265785; U.S. Pat. No. 4,769,331 (recombinant herpesvirus); Roizman, "The function of herpes simplex virus genes: A primer for genetic engineering of novel vectors," PNAS USA 93:11307-11312, October 1996; Andreansky et al., "The application of genetically engineered herpes simplex viruses to the treatment of experimental brain tumors," PNAS USA 93: 11313-11318, October 1996; Robertson et al., "Epstein-Barr virus vectors for gene delivery to B lymphocytes", PNAS USA 93: 11334-11340, October 1996; Frolov et al., "Alphavirus-based expression vectors: Strategies and applications," PNAS USA 93: 11371-11377, October 1996; Kitson et al., J. Virol. 65, 3068-3075, 1991; U.S. Pat. Nos. 5,591,439, 5,552,143; WO 98/00166; allowed U.S. application Ser. Nos. 08/675, 556, and 08/675,566 both filed Jul. 3, 1996 (recombinant adenovirus); Grunhaus et al., 1992, "Adenovirus as cloning vectors," Seminars in Virology (Vol. 3) p. 237-52, 1993; Ballay et al. EMBO Journal, vol. 4, p. 3861-65, Graham, Tibtech 8, 85-87, April, 1990; Prevec et al., J. Gen Virol. 70, 42434; PCT WO 91/11525; Felgner et al. (1994), J. Biol. Chem. 269, 2550-2561, Science, 259: 1745-49, 1993; and McClements et al., "Immunization with DNA vaccines encoding glycoprotein D or glycoprotein B, alone or in combination, induces protective immunity in animal models of herpes simplex virus-2 disease", PNAS USA 93: 11414-11420, October 1996; and U.S. Pat. Nos. 5,591,639, 5,589,466, and 5,580,859, as well as WO 90/11092, WO93/19183, WO94/21797, WO95/11307, WO95/20660; Tang et al., Nature, and Furth et al., Analytical Biochemistry, relating to DNA expression vectors, inter alia. See also WO 98/33510; Ju et al., Diabetologia, 41: 736-739, 1998 (lentiviral expression system); Sanford et al., U.S. Pat. No. 4,945,050; Fischbach et al. (Intracel); WO 90/01543; Robinson et al., Seminars in Immunology vol. 9, pp. 271-283 (1997), (DNA vector systems); Szoka et al., U.S. Pat. No. 4,394,448 (method of inserting DNA into living cells); McCormick et al., U.S. Pat. No. 5,677,178 (use of cytopathic viruses); and U.S. Pat. No. 5,928,913 (vectors for gene delivery); as well as other documents cited herein.

The term "viral vector" describes a genetically modified virus which was manipulated by recombinant DNA technique in a way so that its entry into a host cell results in a specific biological activity, e.g. the expression of a transgene carried by the vector. In a specific aspect the transgene is an antigen. A viral vector may or may not be replication competent in the target cell, tissue, or organism. It is in particular understood, that the term "viral vector", as used herein, is equivalent to the term "virus vector".

Generation of a viral vector can be accomplished using any suitable genetic engineering techniques well known in the art, including, without limitation, the standard techniques of restriction endonuclease digestion, ligation, transformation, plasmid purification, DNA sequencing, transfection in cell cultures, for example as described in Sambrook et al. (Molecular Cloning: A Laboratory Manual. Cold Spring Harbor Laboratory Press, N.Y. (1989)) or K. Maramorosch and H. Koprowski (Methods in Virology Volume VIII, Academic Press Inc. London, UK (2014)).

A viral vector can incorporate sequences from the genome of any known organism. The sequences can be incorporated in their native form or can be modified in any way to obtain a desired activity. For example, the sequences can comprise insertions, deletions or substitutions.

A viral vector can include coding regions for two or more proteins of interest. For example, the viral vector can include the coding region for a first protein of interest and the coding region for a second protein of interest. The first protein of interest and the second protein of interest can be the same or different. In some embodiments, the viral vector can include the coding region(s) for a third or a fourth protein of interest. The third and the fourth protein of interest can be the same or different. The total length of the two or more proteins of interest encoded by one viral vector can vary. For example, the total length of the two or more proteins can be at least about 200 amino acids. At least about 250 amino acids, at least about 300 amino acids, at least about 350 amino acids, at least about 400 amino acids, at least about 450 amino acids, at least about 500 amino acids, at least about 550 amino acids, at least about 600 amino acids, at least about 650 amino acids, at least about 700 amino acids, at least about 750 amino acids, at least about 800 amino acids, or longer.

The terms "viral vector" and "viral construct" can be used interchangeably.

The term "construct", as used herein, refers to a recombinant nucleic acid such as a plasmid, a BAC, or a recombinant virus that has been artificially generated.

The term "plasmid" refers to cytoplasmic DNA that replicates independently of the bacterial chromosome within a bacterial host cell. In a specific aspect of the present invention the term "plasmid" and/or "transfer plasmid" refers to an element of recombinant DNA technology useful for construction of e.g. an expression cassette for insertion into a viral vector. In another specific aspect the term "plasmid" may be used to specify a plasmid useful for DNA vaccination purposes.

As used herein, the terms "nucleic acid" and "polynucleotide" are interchangeable and refer to any nucleic acid. The term "nucleic acid sequence" is understood to be equivalent to the term "nucleotide sequence". The term "nucleotide sequence" is understood to be equivalent to the term "polynucleotide sequence".

The term "nucleic acid", "nucleic acid sequence", "nucleotide sequence", "polynucleotide", "polynucleotide sequence", "RNA sequence" or "DNA sequence" as used herein refers to an oligonucleotide, nucleotide or polynucleotide and fragments and portions thereof and to DNA or RNA of genomic or synthetic origin, which may be single or double stranded and represent the sense or antisense strand. The sequence may be a non-coding sequence, a coding sequence or a mixture of both. The nucleic acid sequences of the present invention can be prepared using standard techniques well known to one of skill in the art.

The terms "nucleic acid" and "polynucleotide" also specifically include nucleic acids composed of bases other than the five biologically occurring bases (adenine, guanine, thymine, cytosine and uracil).

As used herein, the term "promoter" or "promoter sequence" means a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and animals such as mammals (including horses, pigs, cattle and humans), birds or insects. A promoter can be inducible, repressible, and/or constitutive. Inducible promoters initiate increased levels of transcription from DNA under their control in response to some change in culture conditions, such as a change in temperature (Ptashne, 2014). Examples of promoters well known to the person skilled in the art are for example SV40 large T, HCMV and MCMV immediate early gene 1, human elongation factor alpha promoter, baculovirus polyhedrin promoter.

The term "complementary nucleotide sequences" describes one strand of the two paired strands of polynucleotides such as DNA or RNA. The nucleotide sequence of the complementary strand mirrors the nucleotide sequence of its paired strand so that for each adenosin it contains a thymin (or uracil for RNA), for each guanine a cytosin, and vice versa. The complementary nucleotide sequence of e.g. 5'-GCATAC-3' is 3'-CGTATG-5' or for RNA 3'-CGUAUG-5'.

The terms "gene", "gene of interest", as used herein have the same meaning and refer to a polynucleotide sequence of any length that encodes a product of interest. The gene may further comprise regulatory sequences preceding (5' non-coding or untranslated sequences) and following (3' non-coding or untranslated sequences) the coding sequence. The selected sequence can be full length or truncated, a fusion or tagged gene, and can be a cDNA, a genomic DNA, or a DNA fragment. It is generally understood that genomic DNA encoding for a polypeptide or RNA may include non-coding regions (i.e. introns) that are spliced from mature messenger RNA (mRNA) and are therefore not present in cDNA encoding for the same polypeptide or RNA. It can be the native sequence, i.e. naturally occurring form(s), or can be mutated, or comprising sequences derived from different sources or otherwise modified as desired. These modifications include codon optimizations to optimize codon usage in the selected host cell or tagging. Furthermore they can include removal or additions of cis-acting sites such as (cryptic) splice donor, acceptor sites and branch points, polyadenylation signals, TATA-boxes, chi-sites, ribosomal entry sites, repeat sequences, secondary structures (e.g. stem loops), binding sites for transcription factors or other regulatory factors, restriction enzyme sites etc. to give just a few, but not limiting examples. The selected sequence can encode a secreted, cytoplasmic, nuclear, membrane bound or cell surface polypeptide.

"Essential gene" or "essential genes", respectively, as used herein is in particular intended to encompass genes that are obligatory for replication in the host cell.

The term "nucleotide sequence of interest" as used herein is a more general term than gene of interest as it does not necessarily comprise a gene but may comprise elements or parts of a gene or other genetic information, e.g. ori (origin of replication). A nucleotide sequence of interest may be any DNA or RNA sequence independently of whether it comprises a coding sequence or not.

The term "transcription" describes the biosynthesis of mRNA in a cell.

The term "expression" as used herein refers to transcription and/or translation of a nucleic acid sequence within a host cell. According to specific aspects of the present invention the term "expression" refers to transcription and/or translation of a heterologous and/or exogenous nucleic acid sequence within a host cell. The level of expression of a desired product in a host cell may be determined on the basis of either the amount of corresponding RNA or mRNA that is present in the cell, or the amount of the desired polypeptide encoded by the selected sequence. For example, mRNA transcribed from a selected sequence can be quantitated by Northern blot hybridization, ribonuclease RNA protection, in situ hybridization to cellular RNA or by RTqPCR (reverse transcription followed by quantitative PCR). Proteins expressed from a selected sequence can be quantitated by various methods, e.g. by ELISA, by Western blotting, by radioimmunoassays, by immunoprecipitation, by assaying for the biological activity of the protein, or by immunostaining of the protein followed by FACS analysis.

The term "expression cassette" or "transcription unit" or "expression unit" defines a region within a vector, construct or polynucleotide sequence that contains one or more genes to be transcribed, wherein the nucleotide sequences encoding the transcribed gene(s) as well as the polynucleotide sequences containing the regulatory elements contained within an expression cassette are operably linked to each other. They are transcribed from a promoter and transcription is terminated by at least one polyadenylation signal. In one specific aspect, they are transcribed from one single promoter. As a result, the different genes are at least transcriptionally linked. More than one protein or product can be transcribed and expressed from each transcription unit (multicistronic transcription unit). Each transcription unit will comprise the regulatory elements necessary for the transcription and translation of any of the selected sequences that are contained within the unit. And each transcription unit may contain the same or different regulatory elements. For example, each transcription unit may contain the same terminator, IRES element or introns may be used for the functional linking of the genes within a transcription unit. A vector or polynucleotide sequence may contain more than one transcription The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). Specifically the tissue culture infectious dose fifty per milliliter (TCID50/ml) gives the dilution of a virus preparation at which 50% of a number of cell cultures inoculated in parallel with that dilution are infected.

"Transcription-regulatory elements" normally comprise a promoter upstream of the gene sequence to be expressed, transcription initiation and termination sites and a polyadenylation signal.

The term "transcription initiation site" refers to a nucleic acid in the construct corresponding to the first nucleic acid incorporated into the primary transcript, i.e. the mRNA precursor. The transcription initiation site may overlap with the promoter sequences.

The "termination signal" or "terminator" or "polyadenylation signal" or "polyA" or transcription termination site" or "transcription termination element" is a signal sequence which causes cleavage at a specific site at the 3' end of the eukaryotic mRNA and post-transcriptional incorporation of a sequence of about 100-200 adenine nucleotides (polyA tail) (SEQ ID NO: 46) at the cleaved 3' end, and thus causes RNA polymerase to terminate transcription. The polyadenylation signal comprises the sequence AATAAA (SEQ ID NO: 47) about 10-30 nucleotides upstream of the cleavage site and a sequence located downstream. Various polyadenylation elements are known such as tk polyA, SV40 late and early polyA, BGH polyA (described for example in U.S. Pat. No. 5,122,458) or hamster growth hormone polyA (WO2010010107).

"Translation regulatory elements" comprise a translation initiation site (AUG), a stop codon and a polyA signal for each individual polypeptide to be expressed. An internal ribosome entry site (IRES) may be included in some constructs. In order to optimize expression it may be advisable to remove, add or alter 5'- and/or 3'-untranslated regions of the nucleic acid sequence to be expressed to eliminate any potentially extra inappropriate alternative translation initiation codons or other sequences that may interfere with or reduce expression, either at the level of transcription or translation. Consensus ribosome binding sites (Kozak sequence) can be inserted immediately upstream of the start codon to enhance translation and thus expression. Increased A/U contents around this ribosome binding site further a more efficient ribosome binding.

By definition, every polynucleotide sequence or every gene inserted in a host cell and the respective protein or RNA encoded thereby is referred to as "exogenous", "exogenous sequence", "exogenous gene", "exogenous coding sequence", with respect to the host cell, when it comes from a different (virus) species. As used herein in respect to a sequence or gene of interest such as an antigen the term "exogenous" means that said sequence or gene of interest, specifically said antigen is expressed out of its natural species context. Accordingly, the CPV VP2 antigen is one example (see example 2) of an exogenous antigen in respect to the Paramyxoviridae virus vector. As used herein, the term "exogenous RNA" or "exogenous nucleic acid sequence" in particular refers to a nucleic acid sequence that was introduced into the genome of a Paramyxoviridae virus from an external source, such as from a recombinant sequence. Examples of such external source comprise Paramyxoviridae virus sequences as well as non Paramyxoviridae virus derived sequences. More particular, the introduction of the exogenous nucleic acid sequence results in a genome or a gene, respectively, having a non-naturally occurring portion. As used herein, the term "exogenous RNA" thus in particular refers to a nucleotide sequence, which is not naturally found in the Paramyxoviridae virus genome. Such non-naturally occurring portion or not naturally found sequence, respectively, can also be the result of the insertion of one naturally occurring nucleotide sequence into another naturally occurring nucleotide sequence.

By definition, every polynucleotide sequence or every gene inserted in a host cell and the respective protein or RNA encoded thereby is referred to as "heterologous, "heterologous sequence", "heterologous gene", "heterologous coding sequence", "transgene" or "heterologous protein" with respect to the host cell. This applies even if the sequence to be introduced or the gene to be introduced is identical to an endogenous sequence or an endogenous gene of the host cell. For example, a 5' non-coding region of an N gene of a Paramyxoviridae virus introduced into a Paramyxoviridae viral vector at a different site or in modified form than in the Paramyxoviridae wild type virus is by definition a heterologous sequence. As used herein in respect to a sequence or gene of interest such as an antigen, the term "heterologous" means that said sequence or gene of interest, specifically said antigen, is expressed out of its natural subspecies context.

The term "non-naturally occurring" means any sequence or gene of interest such as an antigen, which is not occurring in this context naturally, such as a hybrid sequence or a sequence or gene of interest such as an antigen from a different species, or sequence or gene of interest such as an antigen, which is not a product of nature due to artificial mutation, insertion, deletion or the like.

The term "recombinant" is used exchangeably with the terms "non-naturally occurring", "heterologous" and "exogenous" throughout the specification of this present invention. Thus, a "recombinant" protein is a protein expressed from a either a heterologous or an exogenous polynucleotide sequence. The term recombinant as used with respect to a virus, means a virus produced by artificial manipulation of the viral genome. A virus comprising a heterologous or an exogenous sequence such as an exogenous antigen encoding sequence is a recombinant virus. The term recombinant virus and the term non-naturally occurring virus are used interchangeably.

Thus, the term "heterologous vector" means a vector that comprises a heterologous or an exogenous polynucleotide sequence. The term "recombinant vector" means a vector that comprises a heterologous or a recombinant polynucleotide sequence.

As used herein, the term "operably linked" is used to describe the connection between regulatory elements and a gene or its coding region. Typically, gene expression is placed under the control of one or more regulatory elements, for example, without limitation, constitutive or inducible promoters, tissue-specific regulatory elements, and enhancers. A gene or coding region is said to be "operably linked to" or "operatively linked to" or "operably associated with" the regulatory elements, meaning that the gene or coding region is controlled or influenced by the regulatory element. For instance, a promoter is operably linked to a coding sequence if the promoter effects transcription or expression of the coding sequence.

It is in particular understood in the context of the present invention that the term "being [ . . . ] identical with the sequence" is equivalent to the term "having [ . . . ] sequence identity with the sequence".

As used herein, it is in particular understood that the term "being at least X % identical with the sequence of SEQ ID NO:Y" is equivalent to the term "being at least X % identical with the sequence of SEQ ID NO:Y over the length of SEQ ID NO:Y" or to the term "being at least X % identical with the sequence of SEQ ID NO:Y over the entire length of SEQ ID NO:Y", respectively. In this context, "X" is any number from 66 to 100, in particular any integer selected from 66 to 100, such that "X % sequence identity" represents any of the percent sequence identities mentioned herein. Respectively, "Y" in this context is any integer selected from 1 to 45, such that "SEQ ID NO:Y" represents any of the SEQ ID NOs mentioned herein.

It is furthermore understood that the term "being at least 99% identical", as described herein, also (in one extreme of the range) comprises and relates to the term "being 100% identical" or "being identical with the sequence", respectively.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, 91%, 92%, 93%, 94%, even more preferably 95%, 96%, 97%, 98%, 99%, 99.9% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, 91%, 92%, 93%, 94%, even more preferably 95%, 96%, 97%, 98%, 99%, 99.9% identity relative to the reference nucleotide sequence, up to 15%, preferably 10%, 9%, 8%, 7%, 6%, even more preferably 5%, 4%, 3%, 2%, 1%, 0.1% of the nucleotides in the reference sequence may be deleted or substituted with another nucleotide, or a number of nucleotides up to 15%, preferably 10%, 9%, 8%, 7%, 6%, even more preferably 5%, 4%, 3%, 2%, 1%, 0.1% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, 91%, 92%, 93%, 94%, even more preferably 95%, 96%, 97%, 98%, 99% sequence identity to a reference amino acid sequence, it is intended that the given amino acid sequence of the polypeptide is identical to the reference sequence except that the given polypeptide sequence may include up to 15, preferably up to 10, 9, 8, 7, 6, even more preferably up to 5, 4, 3, 2, 1 amino acid alterations per each 100 amino acids of the reference amino acid sequence. In other words, to obtain a given polypeptide sequence having at least 85%, preferably 90%, 91%, 92%, 93%, 94%, even more preferably 95%, 96%, 97%, 98%, 99% sequence identity with a reference amino acid sequence, up to 15%, preferably up to 10%, 9%, 8%, 7%, even more preferably up to 5%, 4%, 3%, 2%, 1% of the amino acid residues in the reference sequence may be deleted or substituted with another amino acid, or a number of amino acids up to 15%, preferably up to 10%, 9%, 8%, 7%, even more preferably up to 5%, 4%, 3%, 2%, 1% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "sequence identity" or "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that several different computer programs are available to determine the identity between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at ncbi.nlm.nih.gov/.

Vaccine Definitions

An "immunogenic or immunological composition" refers to a composition of matter that comprises at least one antigen, or immunogenic portion thereof, that elicits an immunological response in the host of a cellular or antibody-mediated immune response to the composition.

The term "antigen" used herein is well understood in the art and includes substances which are immunogenic, i.e., immunogens, as well as substances which induce immunological unresponsiveness, or anergy, i.e., a lack of reactions by the body's defense mechanisms to foreign substances. As used herein, the term "antigen" is intended to mean full length proteins as well as peptide fragments thereof containing or comprising epitope.

The term "food producing animal" means animals which are used for human consumption such as swine, cattle, poultry, fish and the like, preferably food producing animal means swine and cattle, most preferably swine.

An "immunogenic composition" as used herein can refer to a polypeptide or a protein, such as for example a viral surface protein that elicits an immunological response as described herein. The term "immunogenic fragment" or "immunogenic portion" refers to a fragment or truncated and/or substituted form of a protein or polypeptide that includes one or more epitopes and thus elicits the immunological response described herein. In general, such truncated and/or substituted forms, or fragments will comprise at least six contiguous amino acids from a full-length protein. Such fragments can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by concurrently synthesizing large numbers of peptides on solid supports, the peptides corresponding to portions of the protein molecule, and reacting the peptides with antibodies while the peptides are still attached to the supports. Such techniques are known and described in the art, see e.g., U.S. Pat. No. 4,708,871; Geysen et al. (1984) Proc. Natl. Acad. Sci. USA 81:3998-4002; and Geysen et al. (1986) Molec. Immunol. 23:709-715. Similarly, conformational epitopes are readily identified by determining spatial conformation of amino acids such as by, e.g., x-ray crystallography and two-dimensional nuclear magnetic resonance. See Epitope Mapping Protocols, supra. Synthetic antigens are also included within the definition, for example, polyepitopes, flanking epitopes, and other recombinant or synthetically derived antigens. See, e.g., Bergmann et al. (1993) Eur. J. Immunol. 23:2777-2781; Bergmann et al. (1996), J. Immunol. 157:3242-3249; Suhrbier, A. (1997), Immunol. and Cell Biol. 75:402-408; and Gardner et al., (1998) 12th World AIDS Conference, Geneva, Switzerland, Jun. 28-Jul. 3, 1998. (The teachings and content of which are all incorporated by reference herein.)

The term "vaccine" as used herein refers to a pharmaceutical composition comprising at least one immunologically active component that induces an immunological response in an animal and possibly but not necessarily one or more additional components that enhance the immunological activity of the active component. A vaccine may additionally comprise further components typical to pharmaceutical compositions. By way of distinction the immunologically active component of a vaccine may comprise complete virus particles in either their original form or as attenuated particles in a so called modified live vaccine (MLV) or particles inactivated by appropriate methods in a so called killed vaccine (KV). In another form the immunologically active component of a vaccine may comprise appropriate elements of the organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian, or other species plus optionally subsequent isolation and purification procedures, or by induction of the synthetic processes in the animal needing a vaccine by direct incorporation of genetic material using suitable pharmaceutical compositions (polynucleotide vaccination). A vaccine may comprise one or simultaneously more than one of the elements described above. As used within specific aspects of the present invention "vaccine" refers to a live vaccine or live virus, also called recombinant vaccine. In another specific aspect of the present invention "vaccine" refers to an inactivated or killed virus including virus like particles (VLPs). Thus, a vaccine may be a subunit vaccine or a killed (KV) or inactivated vaccine.

The term "Multiplicity of Infection (M.O.I.)" describes how many infectious units, e.g. TCID50, of a virus preparation are used per cell to infect cultured cells. For example, a M.O.I. of 0.01 means that for every 100 cells in a culture vessel one infectious unit is inoculated.

The term "DNA vaccination" or "polynucleotide vaccination" means direct inoculation of genetic material using suitable pharmaceutical compositions.

Various physical and chemical methods of inactivation are known in the art. The term "inactivated" refers to a previously virulent or non-virulent virus or bacterium that has been irradiated (ultraviolet (UV), X-ray, electron beam or gamma radiation), heated, or chemically treated to inactivate or kill such virus or bacterium while retaining its immunogenicity. Suitable inactivating agents include beta-propiolactone, binary or beta- or acetyl-ethyleneimine, gluteraldehyde, ozone, and formalin (formaldehyde).

For inactivation by formalin or formaldehyde, formaldehyde is typically mixed with water and methyl alcohol to create formalin. The addition of methyl alcohol prevents degradation or cross reaction during the in activation process. One embodiment uses about 0.1 to 1% of a 37% solution of formaldehyde to inactivate the virus or bacterium. It is critical to adjust the amount of formalin to ensure that the material is inactivated but not so much that side effects from a high dosage occur.

More particularly, the term "inactivated" in the context of a virus means that the virus is incapable of replication in vivo or in vitro and, respectively, the term "inactivated" in the context of a bacterium means that the bacterium is incapable of reproduction in vivo or in vitro. For example, the term "inactivated" may refer to a virus that has been propagated in vitro, and has then been inactivated using chemical or physical means so that it is no longer capable of replicating. In another example, the term "inactivated" may refer to a bacterium that has been propagated, and then inactivated using chemical or physical means resulting in a suspension of the bacterium, fragments or components of the bacterium, such as resulting in a bacterin which may be used as a component of a vaccine.

As used herein, the terms "inactivated", "killed" or "KV" are used interchangeably.

The term "live vaccine" refers to a vaccine comprising either a living organism or a replication competent virus or viral vector.

A "pharmaceutical composition" essentially consists of one or more ingredients capable of modifying physiological, e.g., immunological functions, of the organism it is administered to, or of organisms living in or on the organism. The term includes, but is not restricted to, antibiotics or antiparasitics, as well as other constituents commonly used to achieve certain other objectives such as, but not limited to, processing traits, sterility, feasibility to administer the composition via enteral or parenteral routes such as oral, intranasal, intravenous, intramuscular, subcutaneous, intradermal, or other suitable route, tolerance after administration, or controlled release properties. One non-limiting example of such a pharmaceutical composition, solely given for demonstration purposes, could be prepared as follows: cell culture supernatant of an infected cell culture is mixed with a stabilizer (e.g., spermidine and/or bovine serum albumin (BSA) and the mixture is subsequently lyophilized or dehydrated by other methods. Prior to vaccination, the mixture is then rehydrated in aqueous (e.g., saline, phosphate buffered saline (PBS) or non-aqueous solutions (e.g., oil emulsion, aluminum-based adjuvant).

As used herein, "pharmaceutical- or veterinary-acceptable carrier" includes any and all solvents, dispersion media, coatings, adjuvants, stabilizing agents, diluents, preservatives, antibacterial and antifungal agents, isotonic agents, adsorption delaying agents, and the like. In some preferred embodiments, and especially those that include lyophilized immunogenic compositions, stabilizing agents for use in the present invention include stabilizers for lyophilization or freeze-drying.

In some embodiments, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed.Stewart-Tull, D. E. S.), JohnWiley and Sons, NY, pp51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name CARBOPOL®; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of CARBOPOL® 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

"Attenuation" means reducing the virulence of a pathogen. In the present invention "attenuation" is synonymous with "avirulent". In the present invention, an attenuated virus is one in which the virulence has been reduced so that it does not cause clinical signs of infection but is capable of inducing an immune response in the target animal, but may also mean that the clinical signs are reduced in incidence or severity in animals infected with the attenuated virus, especially the Paramyxoviridae virus vector as claimed, in comparison with a "control group" of animals infected with non-attenuated virus or pathogen and not receiving the attenuated virus. In this context, the term "reduce/reduced" means a reduction of at least 10%, preferably 25%, even more preferably 50%, still more preferably 60%, even more preferably 70%, still more preferably 80%, even more preferably 90% and most preferably of 100% as compared to the control group as defined above. Thus, an attenuated, avirulent pathogen such as for example an attenuated viral vector as claimed, especially the Paramyxoviridae virus vector (preferably CDV vector) as claimed, is suitable for the generation of a modified live vaccine (MLV) or modified live immunogenic composition.

Herein, "effective dose" means, but is not limited to, an amount of antigen that elicits, or is able to elicit, an immune response that yields a reduction of clinical symptoms in an animal to which the antigen is administered.

As used herein, the term "effective amount" means, in the context of a composition, an amount of an immunogenic composition capable of inducing an immune response that reduces the incidence of or lessens the severity of infection or incident of disease in an animal. Particularly, an effective amount refers to colony forming units (CFU) per dose. Alternatively, in the context of a therapy, the term "effective amount" refers to the amount of a therapy which is sufficient to reduce or ameliorate the severity or duration of a disease or disorder, or one or more symptoms thereof, prevent the advancement of a disease or disorder, cause the regression of a disease or disorder, prevent the recurrence, development, onset, or progression of one or more symptoms associated with a disease or disorder, or enhance or improve the prophylaxis or treatment of another therapy or therapeutic agent.

An "immune response" or "immunological response" means, but is not limited to, the development of a cellular and/or antibody-mediated immune response to the (immunogenic) composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the host will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of the pathogen, a delay in the of onset of viremia, reduced viral persistence, a reduction in the overall viral load and/or a reduction of viral excretion.

"Protection against disease", "protective immunity", "functional immunity", "reduction of clinical symptoms", "induction/production of neutralizing antibodies and/or serum conversion", and similar phrases, means a partial or complete response against a disease or condition generated by administration of one or more therapeutic compositions of the invention, or a combination thereof, that results in fewer deleterious effects than would be expected in a non-immunized subject that has been exposed to disease or infection. That is, the severity of the deleterious effects of the infection are lessened in a vaccinated subject. Infection may be reduced, slowed, or possibly fully prevented, in a vaccinated subject. Herein, where complete prevention of infection is meant, it is specifically stated. If complete prevention is not stated then the term includes partial prevention.

The term "neutralizing antibody" relates to an antibody that is capable of keeping an infectious agent, usually a virus, e.g., CDV or CPV, from infecting a cell by neutralizing or inhibiting its biological effect. Neutralization can happen when antibodies bind to specific viral antigens, blocking the pathogen from entering their host cells. In one example it prevents the virus from binding to its receptor(s) and getting its genetic material inside the cell.

The term "antibody" or "immunoglobulin," as used interchangeably herein, includes whole antibodies and any antigen binding fragment (antigen-binding portion) or single chain cognates thereof. An "antibody" comprises at least one heavy (H) chain and one light (L) chain. In naturally occurring IgGs, for example, these heavy and light chains are inter-connected by disulfide bonds and there are two paired heavy and light chains, these two also inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR) or Joining (J) regions (JH or JL in heavy and light chains respectively). Each $V_H$ and $V_L$ is composed of three CDRs three FRs and a J domain, arranged from amino-terminus to carboxy-terminus in the following order: FR1, CDR1, FR2, CDR2, FR3, CDR3, J. The variable regions of the heavy and light chains bind with an antigen. The constant regions of the antibodies may mediate the binding of the immunoglobulin to host tissues or factors, including various cells of the immune system (e.g., effector cells) or humoral factors such as the first component (Clq) of the classical complement system.

Herein, "reduction of the incidence and/or severity of clinical signs" or "reduction of clinical symptoms" means, but is not limited to, reducing the number of infected subjects in a group, reducing or eliminating the number of subjects exhibiting clinical signs of infection, or reducing the severity of any clinical signs that are present in one or more subjects, in comparison to wild-type infection. For example, it should refer to any reduction of pathogen load, pathogen shedding, reduction in pathogen transmission, or reduction of any clinical sign symptomatic of malaria. Preferably these clinical signs are reduced in one or more subjects receiving the therapeutic composition of the present invention by at least 10% in comparison to subjects not receiving the composition and that become infected. More preferably clinical signs are reduced in subjects receiving a composition of the present invention by at least 20%, preferably by at least 30%, more preferably by at least 40%, and even more preferably by at least 50%.

The term "increased protection" herein means, but is not limited to, a statistically significant reduction of one or more clinical symptoms which are associated with infection by an infectious agent in a vaccinated group of subjects vs. a non-vaccinated control group of subjects. The term "statistically significant reduction of clinical symptoms" means, but is not limited to, the frequency in the incidence of at least one clinical symptom in the vaccinated group of subjects is at least 10%, preferably 20%, more preferably 30%, even more preferably 50%, and even more preferably 70% lower than in the non-vaccinated control group after the challenge the infectious agent.

"Long-lasting protection" shall refer to "improved efficacy" that persists for at least 3 weeks, but more preferably at least 3 months, still more preferably at least 6 months. In the case of livestock, it is most preferred that the long lasting protection shall persist until the average age at which animals are marketed for meat.

The term "reduction of viremia" induced by a virus means, but is not limited to, the reduction of virus entering the bloodstream of an animal, wherein the viremia level, i.e. the number of virus DNA or RNA copies per mL of blood serum or the number of plaque forming colonies per deciliter of blood serum, is reduced in the blood serum of animals receiving the composition of the present invention by at least 50% in comparison to animals not receiving the composition and may become infected. More preferably, the viremia level is reduced in animals receiving the composition of the present invention by at least 90%, preferably by at least 99.9%, more preferably by at least 99.99%, and even more preferably by at least 99.999%.

As used herein, the term "viremia" is particularly understood as a condition in which virus particles reproduce and/or circulate in the bloodstream of an animal, in particular of a mammal, a bird, or of an insect.

"Safety" refers to the absence of adverse consequences in a vaccinated animal following vaccination, including but not limited to: potential reversion of a virus-based vaccine to virulence, clinically significant side effects such as persistent, systemic illness or unacceptable inflammation at the site of vaccine administration.

The terms "vaccination" or "vaccinating" or variants thereof, as used herein means, but is not limited to, a process which includes the administration of an immunogenic composition of the invention that, when administered to an animal, elicits, or is able to elicit—directly or indirectly—, an immune response in said animal.

"Mortality", in the context of the present invention, refers to death caused by an infection, and includes the situation where the infection is so severe that an animal is euthanized to prevent suffering and provide a humane ending to its life.

Formulations

The subject to which the composition is administered is preferably an animal, including but not limited to cattle, horses, sheep, pigs, poultry (e.g. chickens), goats, cats, dogs, hamsters, mice and rats, most preferably the mammal is a swine.

The formulations of the invention comprise an effective immunizing amount of one or more immunogenic compositions and a physiologically acceptable vehicle. Vaccines comprise an effective immunizing amount of one or more immunogenic compositions and a physiologically acceptable vehicle. The formulation should suit the mode of administration.

The immunogenic composition, if desired, can also contain minor amounts of wetting or emulsifying agents, or pH buffering agents. The immunogenic composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Methods of Treatment

Preferred routes of administration include but are not limited to intranasal, oral, intradermal, and intramuscular. Administration in drinking water, most preferably in a single dose, is desirable. The skilled artisan will recognize that compositions of the invention may also be administered in one, two or more doses, as well as, by other routes of administration. For example, such other routes include subcutaneously, intracutaneously, intraperitnoeally, intracutaneously, and depending on the desired duration and effectiveness of the treatment, the compositions according to the invention may be administered once or several times, also intermittently, for instance on a daily basis for several days, weeks or months and in different dosages such as about $10^3$ to $10^8$ TCID50 (see viral titre above). In a specific aspect of the present invention the dosage is about $10^3$ to $10^8$ TCID50, especially for live virus/live vaccine.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to a mammal, especially a pig. Associated with such container(s) can be a notice in the form prescribed by a governmental agency regulating the manufacture, use or sale of pharmaceuticals or biological products, which notice reflects approval by the agency of manufacture, use or sale for human administration.

Sequences Overview

The following sequences are detailed and disclosed hereby in the present invention, wherein the sequences in the sequence listing are presented in the 5'-end to 3'-end direction from left to right, and wherein:
SEQ ID NO:1 (RNA) corresponds to a 5' non-coding region of an N gene of a CDV,
SEQ ID NO:2 (RNA) corresponds to a 5' non-coding region of a P gene of a CDV,
SEQ ID NO:3 (RNA) corresponds to a 5' non-coding region of a M gene of a CDV,
SEQ ID NO:4 (RNA) corresponds to a 5' non-coding region of a F gene of a CDV,
SEQ ID NO:5 (RNA) corresponds to a 5' non-coding region of an H gene of a CDV,
SEQ ID NO:6 (RNA) corresponds to a 5' non-coding region of a L gene of a CDV,
SEQ ID NO:7 (RNA) corresponds to a 3' non-coding region of an H gene of a CDV,
SEQ ID NO:8 (RNA) corresponds to a 3' non-coding region of an N gene of a CDV,
SEQ ID NO:9 (RNA) corresponds to a 3' non-coding region of an P gene of a CDV,
SEQ ID NO:10 (RNA) corresponds to a 3' non-coding region of an M gene of a CDV,
SEQ ID NO:11 (RNA) corresponds to a 3' non-coding region of an F gene of a CDV,
SEQ ID NO:12 (RNA) corresponds to a 3' non-coding region of an L gene of a CDV,
SEQ ID NO:13 (RNA) corresponds to a sequence encoding a Kozak sequence,
SEQ ID NO:14 (RNA) corresponds to an intergenic sequence of a CDV,
SEQ ID NO:15 (RNA) corresponds to a sequence encoding a VP2 protein of a CPV,
SEQ ID NO:16 (RNA) corresponds to a sequence encoding a H3-subtype hemagglutinin,
SEQ ID NO:17 (RNA) corresponds to a combination of SEQ ID Nos: 14, 1, 15, 13 and 7,
SEQ ID NO:18 (RNA) corresponds to a combination of SEQ ID Nos: 1, 15, 13, 7 and 14,
SEQ ID NO:19 (RNA) corresponds to a combination of SEQ ID Nos: 14, 1, 16, 13 and 7,
SEQ ID NO:20 (RNA) corresponds to a combination of SEQ ID Nos: 1, 16, 13, 7 and 14,
SEQ ID NO:21 (RNA) corresponds to a combination of SEQ ID Nos: 14, 1, 15, 13, 7 and 14, SEQ ID NO:22 (RNA) corresponds to a combination of SEQ ID Nos: 14, 1, 16, 13, 7 and 14,
SEQ ID NO:23 (RNA) corresponds to a sequence comprising the M, F, H and L gene of a CDV,
SEQ ID NO:24 (RNA) corresponds to a sequence comprising the N and P gene of a CDV,
SEQ ID NO:25 corresponds to a DNA reverse complement of SEQ ID NO:1,
SEQ ID NO:26 corresponds to a DNA reverse complement of SEQ ID NO:13,
SEQ ID NO:27 corresponds to a DNA reverse complement of SEQ ID NO:7,
SEQ ID NO:28 corresponds to a DNA reverse complement of SEQ ID NO:14,
SEQ ID NO:29 corresponds to a DNA reverse complement of SEQ ID NO:23,
SEQ ID NO:30 corresponds to a DNA reverse complement of SEQ ID NO:24,
SEQ ID NO:31 corresponds to a DNA reverse complement of SEQ ID NO:15,
SEQ ID NO:32 corresponds to a DNA reverse complement of SEQ ID NO:16,
SEQ ID NO:33 corresponds to a DNA reverse complement of SEQ ID NO:21,
SEQ ID NO:34 corresponds to a DNA reverse complement of SEQ ID NO:22,
SEQ ID NO:35 corresponds to an amino acid sequence of a CPV VP2,
SEQ ID NO:36 corresponds to an amino acid sequence of a H3-subtype hemagglutinin,
SEQ ID NO:37 (RNA) corresponds to a sequence encoding a PEDV S protein,
SEQ ID NO:38 (RNA) corresponds to a sequence encoding a PEDV S protein,
SEQ ID NO:39 (RNA) corresponds to a combination of SEQ ID Nos: 14, 1, 38, 13 and 7,
SEQ ID NO:40 (RNA) corresponds to a combination of SEQ ID Nos: 1, 38, 13, 7 and 14,
SEQ ID NO:41 (RNA) corresponds to a combination of SEQ ID Nos: 14, 1, 38, 13, 7 and 14,
SEQ ID NO:42 corresponds to a DNA reverse complement of SEQ ID NO:37,
SEQ ID NO:43 corresponds to a DNA reverse complement of SEQ ID NO:38,
SEQ ID NO:44 corresponds to a DNA reverse complement of SEQ ID NO:41,
SEQ ID NO:45 corresponds to an amino acid sequence of a PEDV S protein.
SEQ ID NO:46 corresponds to a polyA tail.
SEQ ID NO:47 corresponds to a polyadenylation signal.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Figures 1, 2:
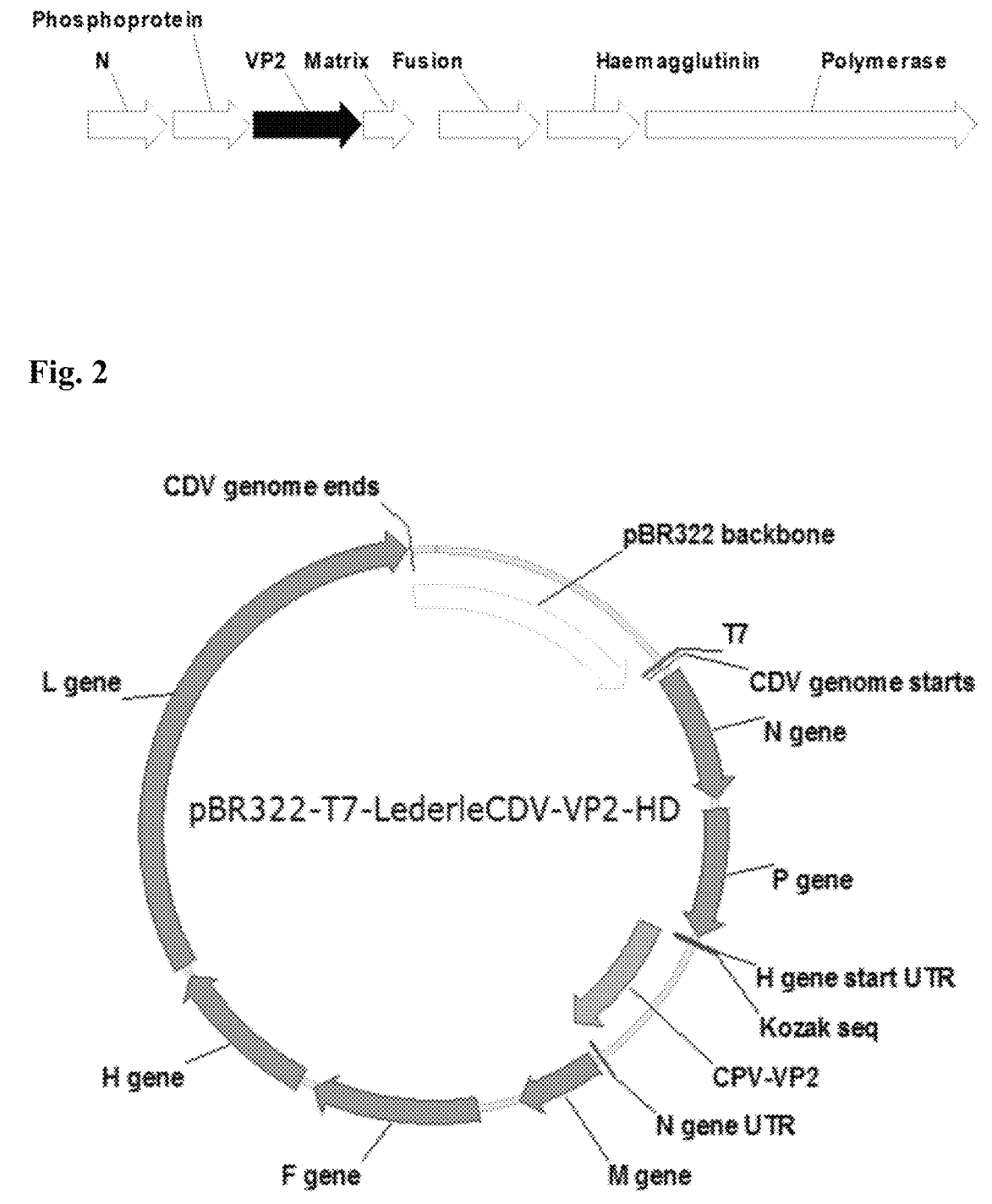

FIG. 1. Schematic illustration of the organisation of canine distemper virus (CDV) vector genome carrying a canine parvovirus VP2 transgene.

FIG. 2. Map of a DNA construct (plasmid) for the generation (rescue) of a CDV recombinant vector with an arrangement of exogenous RNA sequences, wherein the respective plasmid DNA sequences are named "H gene start UTR", "Kozak seq", "CPV-VP2" and "N gene UTR".

Figure 4:
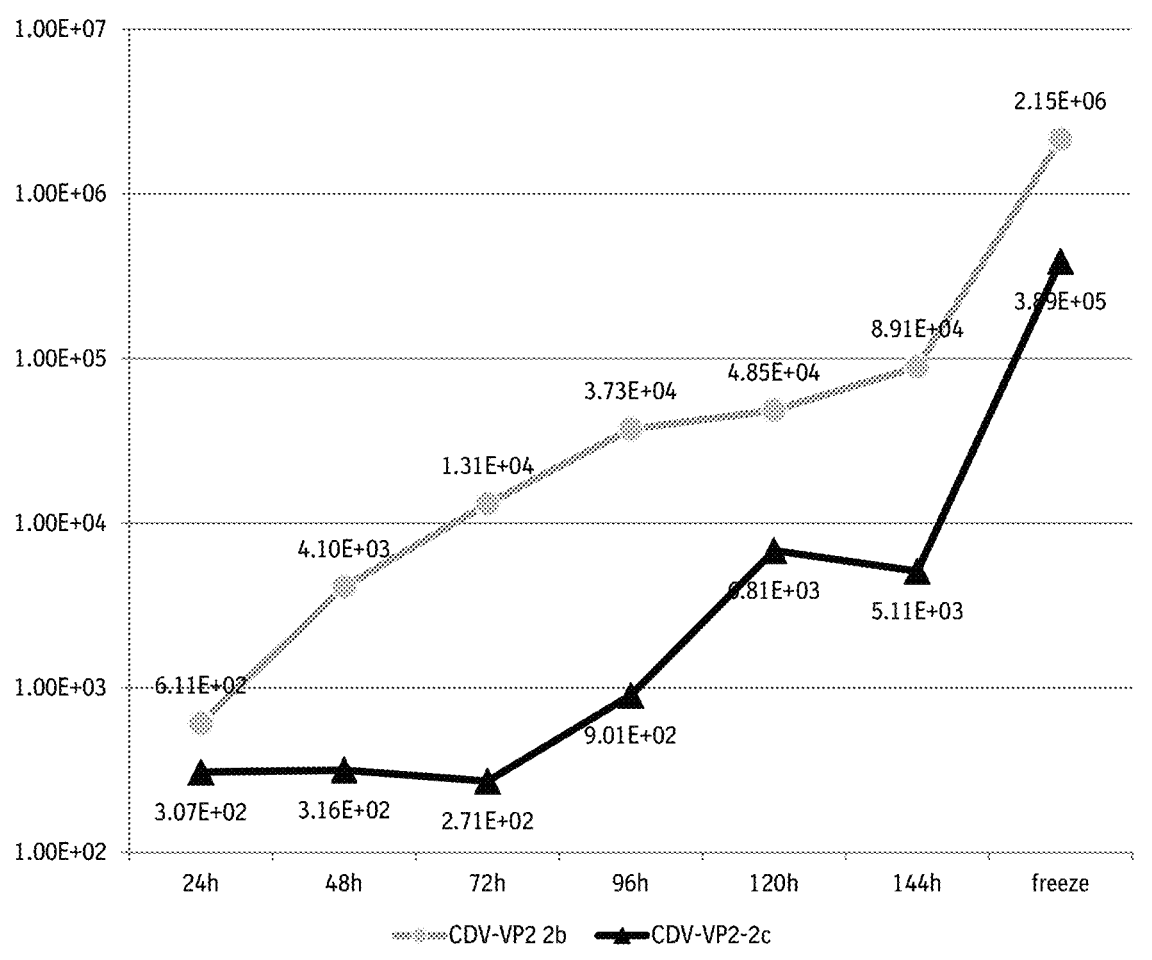

FIG. 4. Virus titres (TCID50) measured in supernatant fraction. The titres represent virus growth in the supernatant sampled by each 24 hour, starting from 1 day post infection during 6 days post infection; "SD"="study day".

Figure 7:
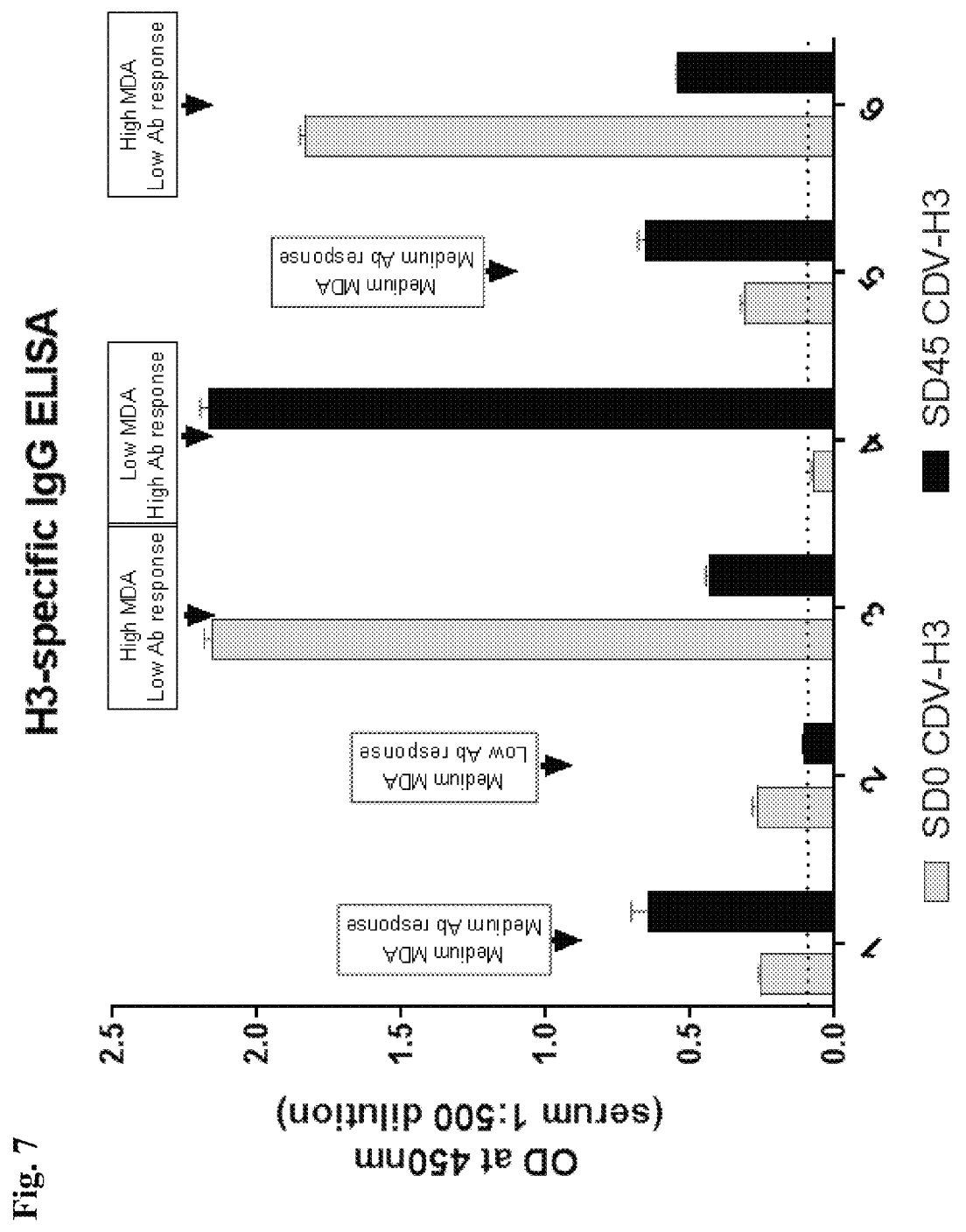

FIG. 7. Antibody levels as determined by an H3-subtype hemagglutinin (H3) specific ELISA test of samples from animals vaccinated with CDV-H3 recombinant. Y axis indicates the readouts represented in OD values of sample dilutions 1:500 for two timepoints, i.e. samples taken from the animals before $1^{st}$ vaccination on study day 0 (SDO) and after second vaccination on study day 45 (SD45).

EXAMPLES

Figure 3:
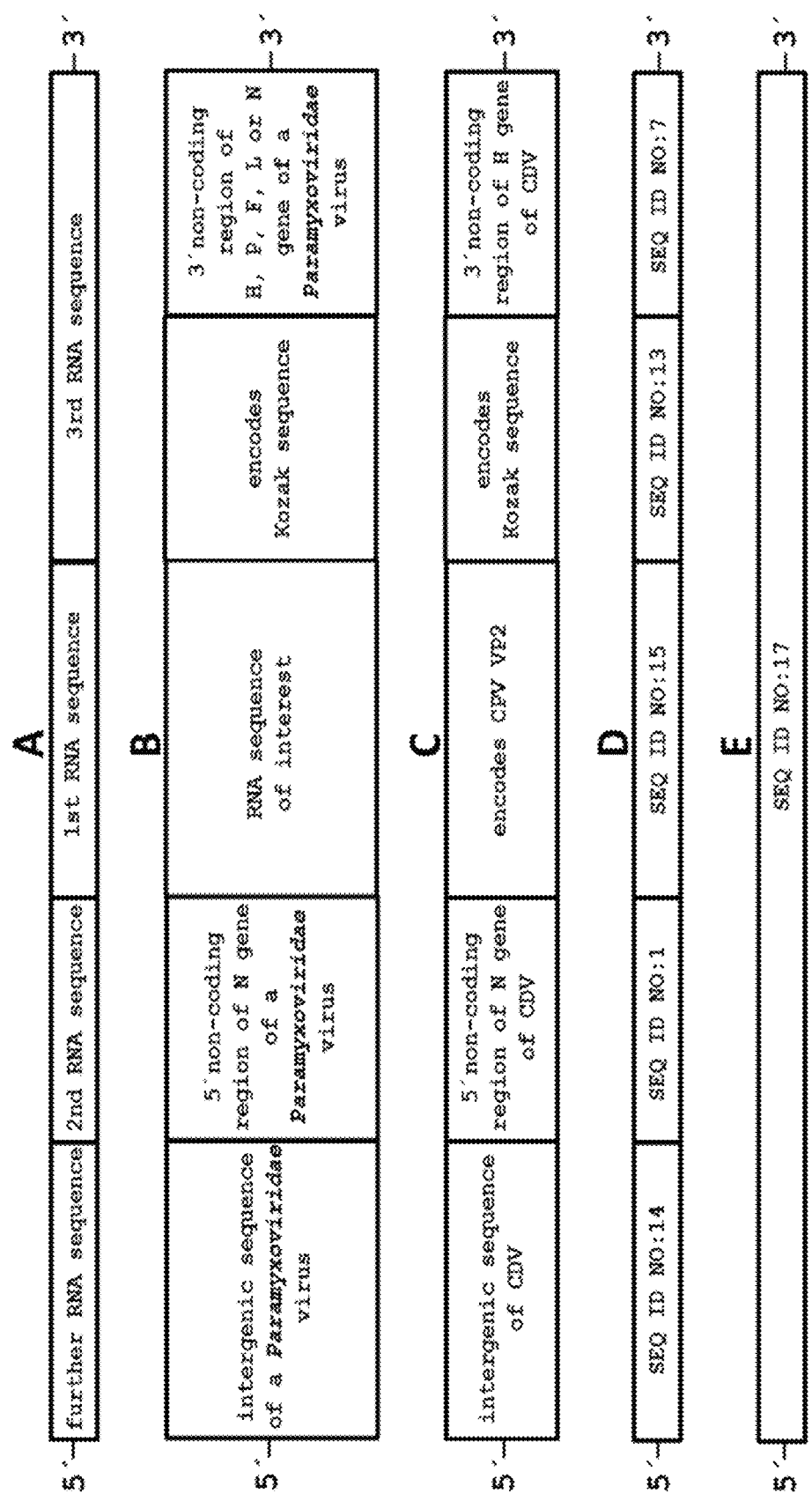
FIG. 3. Schematic representation of an exemplary arrangement of RNA sequences, in 5' end to 3' end direction from left to right: (A.) underlying principal scheme, (B.) arrangement in a Paramyxoviridae virus vector, (C.) arrangement in a CDV vector encoding a canine parvovirus (CPV) VP2, and wherein (D.) and (E.) illustrate the respective arrangement of the sequences as indicated by the SEQ ID NOs of the sequence listing.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

A) CPV-VP2 Expression by CDV Vectors

In an in vitro study using a CDV backbone derived from Lederle vaccine strain with an insert of the sequence of SEQ ID NO:17 between the P gene and the M gene (the vector thus comprising the sequence of SEQ ID NO:21), it was possible to show intracellular expression of canine parvovirus (type 2b) VP2 protein in CDV associated fluorescent focuses. Respective results were also achieved for a corresponding CDV vector (i.e. only differing in the sequence encoding the CPV VP2) encoding a canine parvovirus type 2c (CPV-2c) VP2 protein. Results obtained for both vectors by immunofluorescence indicate strong expression of VP2 protein of CPV in all CDV infected syncytia. VP2, in contrast to CDV antigens, accumulated in nuclei and partially in the cytoplasm of infected cells, which varies during the course of syncytia development and might indicate that CPV-VP2 has transient nucleus trafficking, although no putative nuclear localization sequence has been detected by a routine search within the VP2 gene, nor published in the scientific literature.

B) Genetic Stability

Both CDV vectors of Example 1 A) were evaluated by serial passages involving freeze-thaw cycles at the end of each passage in a Vero cell line (i.e. the CDV production cell line). For assessing the genetic stability of the recombinants, 20 serial cell passages on Vero cells were performed. Sequencing of recombinant clones revealed full genetic stability of the inserted—CPV VP2 sequence and flanking regions. The sequence (incl. mutations) coding for both proteins (at amino acid level) remained unchanged. Additionally, using immunofluoresecence (IF) and western blotting (WB), it was possible to demonstrate that strong VP2 expression was present in the cells infected with CDV-VP2 recombinants during the all passage levels.

C) In Vitro Growth

Both CDV vectors described in Example 1 A) and B) were grown in Vero cells. The peak titres of both recombinants in the roller bottle system were achieved at 144 hours post infection and the titres dramatically increased after freezeing/thawing cycle indicating the cellular association of the virus (similar to parental CDV virus). When compared with parental classical CDV-MLVs, the generated CDV recombinant vaccine candidates have very similar end-titres, acceptable for bio-processing.

In conclusion, both CDV vectors showed good growth kinetics on production in Vero cells, reaching peak titres at 6 days post infection in roller bottles. Both vectors showed strong expression characteristics of transgenes (VP2) as determined by IF and WB, qualifying them as a dual CDV-CPV vaccine candidate. In addition, both viruses were tested for genetic stability for 20 cell passages on Vero cells. Both viruses remained fully genetically stable, indicating that are susceptible for vaccine bio-processing.

Example 2

In Vivo Efficacy Study in Swine:

For the purpose of this experiment a group of 6 piglets were vaccinated with $1\times10^5$ TCID50 of the recombinant CDV vector encoding CPV-2b VP2 (CDV-VP2-2b) of Example 1 at study day (SD) 0 and boosted with $2\times10^4$ TCID50 at SD21. Both applications were performed intramuscularly (IM) in the neck (2 mL volume each dose).

Four animals served as negative control and were inoculated with Vero cell homogenates (2 mL) in the neck. Three animals served as sentinels and did not receive any treatment.

Inclusion Criteria:
Pigs clinically healthy and normally developed for age
Exclusion Criteria:
Pigs with injuries, congenital abnormalities or clinical signs of disease which interfered with the study as assessed by the Study Director or designee
Pigs with a weak body condition (weight <5 kg)
All study animals were housed in facilities appropriate for their age and were kept under same controlled conditions. The room had either plain flooring or alternatively partly-perforated flooring suitable for the age of the animals with four pens of approximately 20 m² each. Before vaccination, the sentinel animals were removed from the group, kept in a separate pen, and were regrouped 12 h after vaccination.

Rooms were under negative pressure (−75 Pa) for biosafety reasons. Room temperature was according to the requirements of the age of the animals. Ventilation rate was approximately 9/h. Animals had 12 h light at >80 lux and 12 h of no light. Environmental enrichment for the animals was provided. Water and feed was available ad libitum in appropriate quality and was managed in accordance with the pigs' requirements at their age and standard procedures.

Laboratory results showed that the CDV vectors replicated in limited fashion in swine host, targeting lymphatic cells. The virus was detected mostly in lymph nodes, spleen or tonsils.

Furthermore, serum virus neutralization tests were performed to measure neutralizing antibodies to CDV and CPV, respectively, in the tests animals.

In the following, the protocol of the serum neutralization test for CDV is given:

Cell Preparation 1 Day Before Neutralization Test
  Trypsinize highly confluent Vero cells and resuspend them in an appropriate volume of MEM Earle's media containing 5% FCS
  Count cells in suspension and adjust to $7\times10^5$ cells/10 mL per 96-well plate
  One plates is sufficient for 4 samples.
  Seed 100 µL of cell suspension/well into all wells of 96-well plates
  Incubate plates at 37° C. in $CO_2$ incubator for 16-24 h Limited Dilution of Serum Samples
  Pre-dilute samples 1:4 with sterile PBS
  Inactivate prediluted sera at 56° C. for 30 minutes
  Add 60 µL of MEM Earle's media supplemented with 1% 100× Pen/Strep to each well of an empty 96-well plate from column 1-11
  Add an additional 36 µL of MEM Earle's media supplemented with 1% 100× Pen/Strep to column 1 (A1-H1)
  Add 24 µL of heat-inactivated serum sample to column 1 (corresponds to 1:5 dilution) (For each serum sample add 24 µL to 3 wells of column 1 to test serum in triplicates)
  Perform twofold serial dilutions of sera by transferring 60 µL from column to column
  Repeat until column 11 (corresponding to 1:5120 dilution)
  Discard 60 µL from the last column Dilution of CDV-Virus
  Dilute CDV-virus to 200 $TCID_{50}$/100 µL in MEM Earle's media supplemented with 1% 100× Pen/Strep, calculate 6 mL per 96-well plate.

Incubation of Serum Samples with CDV-Virus
  Add 60 µL of diluted virus to all wells of column 1-11 of the 96-well plates containing sera dilutions. Start adding virus in column 11.

Gently agitate plates and incubate for 2 hours at 37° C., 5% $CO_2$

Incubation of Serum Sample +/−CDV-Virus on v.d.s Cells

Remove 60 μL media from 1 day old v.d.s cells cells in 96-well plates

After completion of the 2 hours incubation time transfer 100 μL of each well from the serum-virus mixture to the corresponding wells of the v.d.s cell plates column 1-11

Add 100 μL of MEM Earle's media containing 1% 100× Pen/Strep to all wells of column 12 (=cell only control)

Incubate plates for 3 days at 37° C., 5% $CO_2$

Read results by light microscopy observing the virus-induced cytopathic effect.

Figure 5:
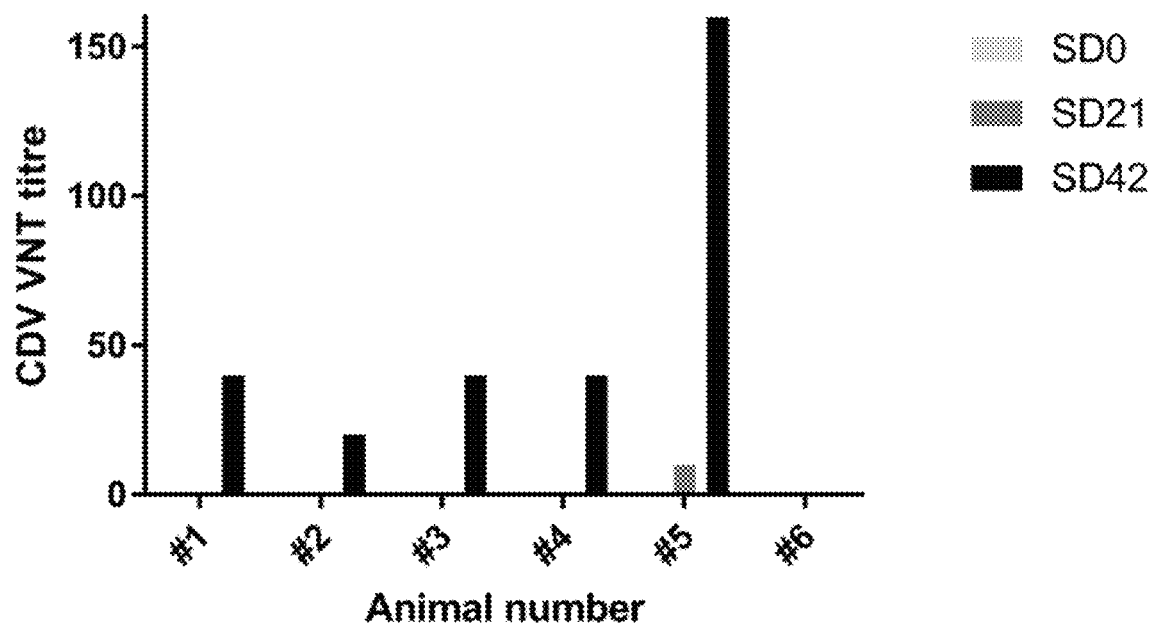
FIG. 5. CDV neutralizing titres during the course of the study of animals vaccinated with CDV-VP2 recombinant. Y axis indicates the maximum dilutions of sera which neutralized the virus in the assay (CDV strain derived from the Lederle strain). The neutralization titre (VNT [Virus Neutralization Test] titre) was measured before $1^{st}$ vaccination on study day 0 (SDO), before $2^{nd}$ vaccination on study day 21 (SD21) and three weeks after second vaccination on study day 42 (SD42). Individual animals are designated in the legends.
Figure 6:
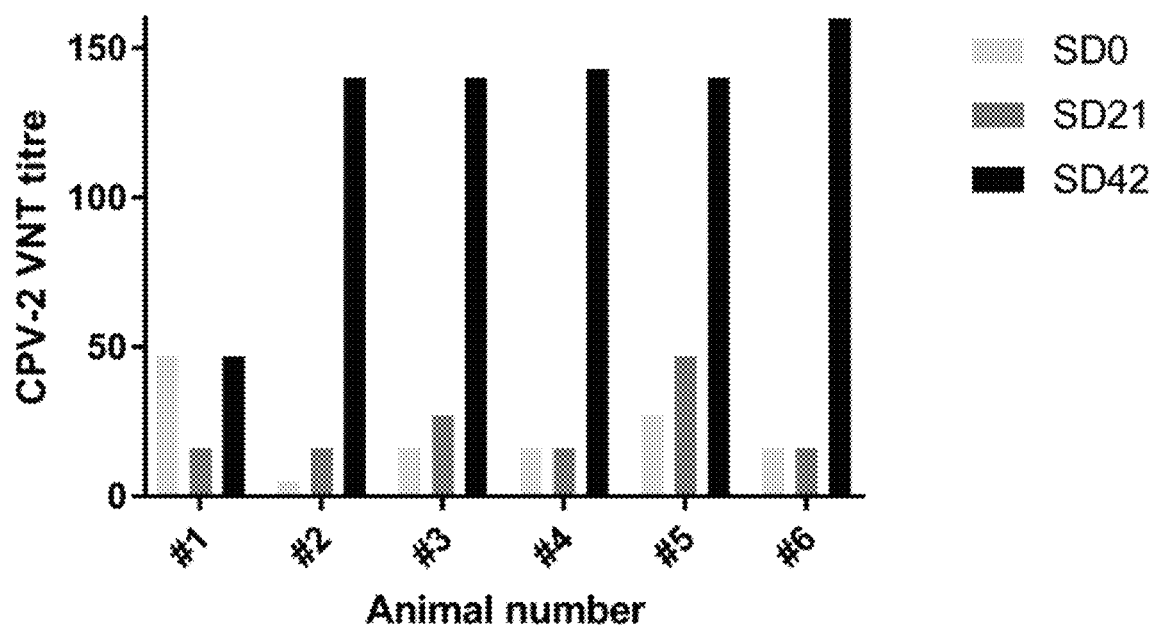
FIG. 6. Canine parvovirus neutralization antibody titres during the course of the study from animals vaccinated with CDV-VP2 recombinant. Y axis indicates the maximum dilutions of sera which neutralized the virus in the assay (CPV). The neutralization titre (VNT [Virus Neutralization Test] titre) was measured before $1^{st}$ vaccination on study day 0 (SDO), before $2^{nd}$ vaccination on study day 21 (SD21) and three weeks after second vaccination on study day 42 (SD42). Individual animals are designated in the legends.

The results for the serum neutralization test for CDV are presented in FIG. 5. All animals had no CDV neutralizing antibodies at the beginning of the study (SDO). Three weeks after the first immunization (SD21, at the time of the second immunization) one animal had neutralizing antibodies against CDV. 21 days after the second immunization (SD42) all but one animal vaccinated with CDV-VP2 had produced significant levels of neutralization antibodies against canine distemper virus. In conjunction with the results of the serum neutralization test for CPV (where all animals strongly reacted to vaccination, including the animal which at SD42 had no CDV neutralization antibodies) and another orthogonal series of tests (c.f. Example 3) it was concluded that this one animal was successfully vaccinated, but that the immune response regarding CDV had shifted to a cellular response.

The serum neutralization test regarding CPV was performed respectively, the results of which are presented in FIG. 6. Concerning the efficacy, all animals vaccinated with CDV-VP2 seroconverted against canine parvovirus 2. Particular increase in neutralizing Ab titres was detected after $2^{nd}$ vaccination (see FIG. 6). The levels of neutralizing antibodies at 21 days after second immunization (SD42) reached the levels of 1:40 to 1:400, which according to the literature, represents a protective titre range in a real host (canids) (Glover et al. 2012, Taguchi et al. 2011).

Importantly, all sentinel animals remained CDV and CPV sero-negative until the end of the study, indicating that the recombinant CDV viruses were not spread from vaccinated animals to non-vaccinated animals upon vaccination.

Example 3

Immunogenicity in H3N2-MDA-Positive Piglets:

In this study, an Hemagglutinin (HA)-specific IgG ELISA and an IFNγ-ELISpot assay were employed for investigating the humoral and cellular immune response of swine influenza maternally derived antibody (MDA)-positive animals vaccinated with a CDV vector encoding H3 of SwIV.

The vaccination of the animals was performed in accordance with Example 2 with the differences that: the insert included in the CDV backbone had the sequence of SEQ ID NO:19 (thus the vector comprising the sequence of SEQ ID NO:22 encoding H3 of SwIV), the vector (named CDV-H3 in the following) was administered to five piglets being H3N2-MDA-positive (MDA+ animals)) and one piglet considered to be (almost) H3N2 seronegative (or having low MDA, respectively), and three piglets served as negative control.

A) HA-Specific IgG ELISA

In the following, the protocol of the ELISA as used is provided:

Flat-bottom 96-well plates (Nunc MaxiSorp #44-2404-21) are coated with 1 μg/mL recombinant influenza hemagglutinin protein (Trenzyme) in carbonate buffer, pH 9.6 overnight at 4° C. On the next day the coating antigen is discarded and plates are washed 5 times with wash buffer (50 mM Tris/0,14M NaCl/0,05% Tween20, pH 8.0) and subsequently incubated. 1 h at room temperature with 200 μL per well of blocking buffer (50 mM Tris/0,14M NaCl/1% BSA, pH 8.0). Sample dilutions are prepared in Sample/Conjugate Diluent (50 mM Tris/0,14M NaCl/0,05% Tween20/1% BSA). Then 100 μL/well of samples and controls (in duplicate) are dispensed into designated wells, covered plates are incubated at RT for 1 hour. Plates are washed 5 times with wash buffer. Afterwards 100 μl of the 1:100.00 diluted HRP-conjugated goat α-Pig IgG-H+L detection antibody (Southern Biotech, Cat #6050-05) is added into each well, and the covered plates are incubated for 1 hour at RT in the dark. After the washing step (5 times with wash buffer), 100 μL/well of the TMB substrate solution (POD, ready to use; Sigma #T4444) is added and the plates are incubated for 5-15 min at RT in the dark. The reaction is stopped by adding 50 μL/well of stop solution (2N sulfuric acid) and the absorbance measured at 450 nm at the ELISA reader (Synergy 2, Biotek).

Using this ELISA, it was seen by means of samples taken from the animals on study day 45 (SD45) that the animals were medium responsive towards the vaccination (animals 1 and 5, see FIG. 7) if the baseline levels of MDA were medium (<OD 1.0 and >OD 0.2), with the exception of animal 2 which predominantly responded by cell-mediated immune response (please see below). Animal 4 having low MDA (<OD 0.2) did show a high antibody response. In contrast, the two animals with high MDA levels above OD 1.0 (animals 3 and 6) did not show an increase of specific H3 antibodies upon vaccination.

B) IFNγ-ELISpot

Additionally, cellular immune response from CDV-H3 vaccinated animals was measured using ELISPOT.

In the following, the protocol of the ELISpot assay as used is provided:

ELISpot plates (96 wells) are coated with purified anti-IFN-γ antibody for at least 12 h. PBMC are thawed, washed twice in PBS (no calcium, no magnesium), counted using trypan blue, and adjusted in RPMI medium to be dispensed to $3\times10_5$ cells/well. After extensive washing of the plate containing the coating antibody with PBS, plate is blocked at least for 1 hour at 37° C. and 5% CO2. Cell culture medium is added containing 3 μg/ml of the polyclonal activator ConA (positive control of IFNγ release) or with different concentrations of the antigen, followed by seeding of the PBMCs. Wells containing only medium or unstimulated cells serve as negative controls. After stimulation for 48 h, plates are washed first two times with water then with PBS/0.01% Tween20. Plates are incubated at room temperature for 1,5 h using a detection biotinylated anti-IFNγ antibody, diluted in PBS/0.01% Tween20/0,1% BSA. Subsequently, streptavidin-alkaline phosphatase enzyme diluted in PBS/0.01% Tween20/0,1% BSA is added to the plates (in the dark, for 45 min incubation). Finally, NBT and 5-Bromo-4-Chloro-3-Indolyl Phosphate are used as substrate of the alkaline phosphatase (development phase takes place also in the dark). These substrate systems produce an insoluble NBT diformazan end product that is blue to purple in color and can be measured in a plate reader. After extensive washing with running tap water, plates are left overnight to ensure complete drying. Spot counting is performed using the C.T.L. ELISpot reader.

Figure 8:
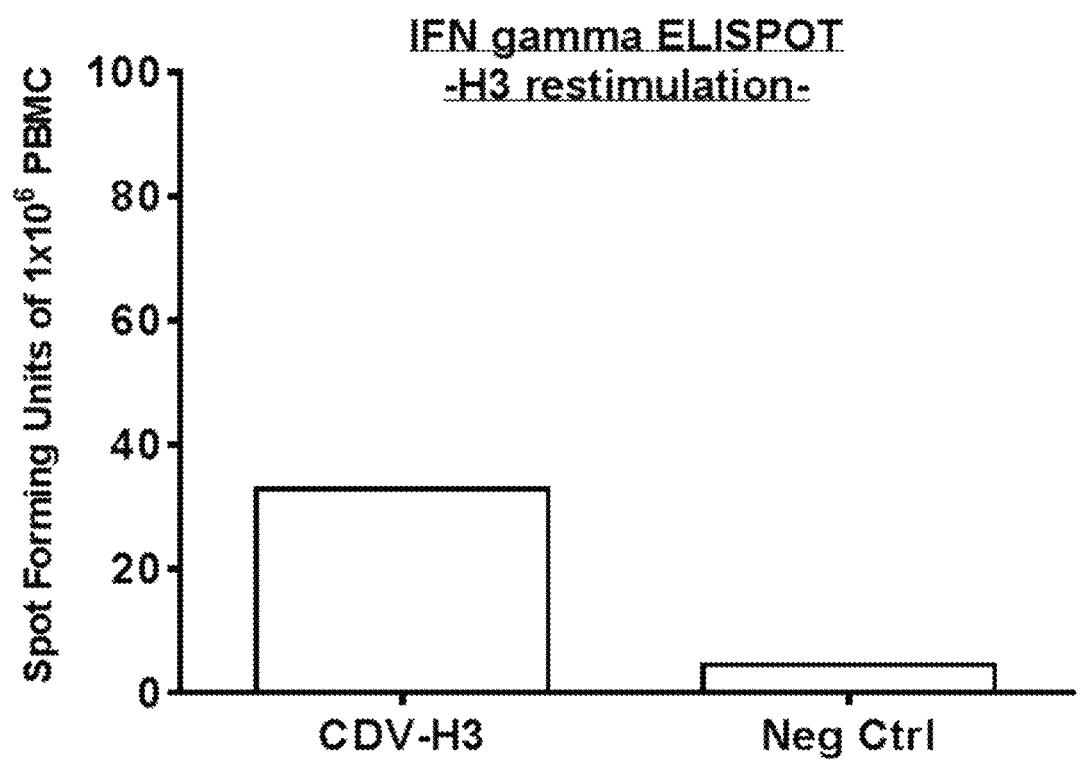
FIG. 8. Results of IFNγ-ELISpot assay after vaccination of H3N2-MDA-positive piglets with CDV-H3 recombinant. Y axis indicates the number of IFN gamma producing cells per million of PBMC (Y axis) in vaccinated animals (left bar, represents mean value for six animals) and non-vaccinated animals (right bar, represents mean value for three animals).

In the assay, recombinant H3 protein was used to stimulate isolated PBMC from the animals vaccinated with CDV-H3 recombinant. As shown in FIG. 8, in the samples of animals vaccinated with two shots (samples taken on study day 28 (SD28)), significantly more IFN gamma producing cells were detected than in PBMCs of non-vaccinated animals. Such induction of cellular immunity is known to improve the vaccine efficacy and faster clearance of the pathogen upon infection. Furthermore, the significant T-cell response of the animals, vaccinated with CDV recombinant expressing hemagglutinin (H3) of the influenza virus of swine, was generated despite the presence of strong (swine influenza) maternal immunity in the vaccinated animals. The presence of pre-existing maternal immunity in young animals often causes interference with active immunisation and is the main cause of vaccine failure in juvenile animals. These findings importantly implicate the characteristics of CDV biology in the vaccinated organism, leading to development of active immunity despite the presence of passively present maternal immunity.

Example 4

Vaccine Efficacy Study

Porcine epidemic diarrhea (PED) is a highly contagious swine disease that can have tremendous economic impact. While all age classes of pigs are susceptible to infection, severe clinical signs and mortality are mainly seen in suckling piglets. The causative agent is PED virus (PEDV), an enveloped, single positive-stranded RNA-virus of the genus Alphacoronavirus within the Coronaviridae virus family. In Europe, PEDV first occurred in the late 1970ies in England. Afterwards it spread through whole Europe causing sporadic outbreaks. In the late 1990ies, PEDV had disappeared from the European pig farms as evidenced by very low seroprevalence and non-existent disease reporting. Outbreaks and endemic infections were still reported from Asia where the disease has high impact on the productivity of industrialized pig farms. Starting from 2005, PED cases were again reported from Europe, i.e. Italy. After the introduction of an apparently highly virulent PEDV into the United States in 2013, cases were also reported from Central Europe, including Germany and neighboring countries. The latter cases were caused by related but distinct PEDV strains (so-called S-INDEL strains). In Germany, cases were reported starting from May 2014 with high morbidity and variable lethality in suckling pigs.

This study, in which a CDV backbone derived from Lederle vaccine strain with an insert of the sequence of SEQ ID NO:38 (encoding a PEDV Spike protein) between the P gene and the M gene (the vector thus comprising the sequence of SEQ ID NO:41) was tested as vector vaccine (named hereinafter "CDV_PEDV-Spike vaccine" or "CDV PEDV-Spike vector vaccine", respectively), included six sows and their offspring.

All animals were checked for PEDV by RT-qPCR targeting the S-gene, and PEDV-specific antibodies. Only negative animals were enrolled in the study.

Three treatment groups (see below) received randomly assigned animals:

Group 1 (negative control): Two sows (designated #1 and #2), unvaccinated

Group 2 (positive control): Two sows (designated #3 and #4), unvaccinated

Group 3 (CDV_PEDV-Spike): Two sows (designated #5 and #6), vaccinated with CDV_PEDV-Spike vector vaccine.

The vaccination of the two sows of group 3 was done according to the following scheme, wherein the stock titer of the CDV_PEDV-Spike vaccine, defined by endpoint titration, was $7,94 \times 10^4$ TCID50/ml:

9 weeks prior to expected farrowing date: each of the two sows received 4 ml of the vaccine intranasally (2 ml in each nostril);

6 weeks prior to expected farrowing date: each of the two sows received 4 ml of the vaccine intranasally (2 ml in each nostril);

3 weeks prior to expected farrowing date: each of the two sows received 4 ml of the respective vaccine intranasally (2 ml in each nostril) and additionally 2 ml intramuscularly.

Piglets born to sows of group 1 (13 piglets of sow #1 and 12 piglets of sow #2) were orally mock-inoculated. Piglets born to sows of group 2 (12 piglets of sow #3 and 14 piglets of sow #4), and group 3 (5 piglets of sow #5 and 15 piglets of sow #6) were orally challenged with a PEDV field strain (named "PEDV EU" hereinafter) at an age of 4 days of life.

For inoculation of piglets of groups 2 and 3, cell culture adapted PEDV EU was used. The titer was $2.15 \times 10^5$ TCID50/ml. Piglets of groups 2 and 3 were orally inoculated. In this case, each piglet received 1 ml of a 1:10 diluted viral stock (titer $2.15 \times 10^4$ TCID50) using 2 ml syringes.

Piglets of group 1 were orally mock-inoculated using 1 ml cell culture medium in 2 ml syringes.

During the whole trial, rectal swabs (COPAN plain swabs without medium) were taken at the day of inoculation and on day 1 to 10 post inoculation (pi) as well as day 14, 17 and 20/21 pi of all animals for RT-qPCR analyses. Additional rectal swabs were taken from 4 piglets of each sow prior to inoculation and two days post challenge for bacteriological examination. Moreover, clinical signs indicative for PED were recorded daily using the established standardized cumulative score system (see below). Blood samples were taken at the day of inoculation and day 14 and 20/21 pi (end of trial) or the day of euthanasia or death of the respective animal.

Clinical Monitoring

The established cumulative clinical score was used for daily monitoring for clinical signs indicative for PED (see table below).

TABLE 1

Cumulative clinical score for clinical signs indicative for PED

| Score | General behaviour | Feed intake/ suckling | Gastrointestinal symptoms |
|---|---|---|---|
| 0 | Agile, attentive, no abnormalities | Greedy suckling, good filled stomach, intake of piglet feed | Physiological feces |
| 1 | Slight depression | Slow suckling, hardly interested in piglet feed | Pasty feces, vomiting |
| 2 | Depression, isolaton from group, vocalisation (moaning) | Reluctant feed intake, hardly interested in suckling/piglet feed, sunken flanks | Watery feces, reddened anal region, vomiting |
| 3 | Lateral position, signs of severe dehydration, low body temperature | Total anorexia, decreasing of milk production of sow | Watery feces with blood or fibrin added, highly reddened anal region, vomiting |

Sample Preparation and Nucleic Acid Extraction

Rectal swabs were submerged in 1 ml Dulbecco's Modified Eagle Medium and incubated for 1 hour at room temperature. Viral RNA was extracted using either the QIAmp ViralRNA Mini Kit (Qiagen) or the NucleoMagVet-Kit in combination with the KingFisher extraction platform. The RNA was stored at −20° degree until further use.

Blood samples were centrifuged at 2031×g for 20 min at room temperature to obtain serum. The resulting serum was aliquoted and stored at −20° C.

Virus Detection

To detect PEDV shedding, RT-qPCR-systems targeting the S-gene of PEDV were used as previously described (Stadler et al., BMC Vet Res. 11:142 (2015)). Samples taken at days 0 to 7 dpi and at 10 and 20/21 dpi were tested for PEDV-genome. The amount of genome copies/µl was calculated using an in-house standard.

Antibody Detection

A commercial indirect ELISA (INgezim PEDV, INGENASA, Madrid, Spain) was performed with all sera according to the producer's manual.

Bacteriology

Fecal swabs of four piglets per litter were taken at 0 and 2 dpi for differential bacteriology.

Statistics

Shapiro-Wilk test was used for normality testing and a Mann-Whitney rank sum test was conducted as implemented in the software package. Statistical significance was tested using SigmaPlot software.

Results

Antibody Detection in Serum:

All piglets of the CDV group showed positive results in the ELISA (detecting antibodies against PEDV Spike protein) prior to challenge inoculation due to antibody positive colostrum intake, while all animals of the positive and negative control group showed clearly negative results.

At 14 dpi all but three piglets in the positive control group seroconverted, while all animals in the vaccine group showed still high amounts of PEDV specific IgG in serum samples.

At the end of the study all piglets of the CDV group and of the positive control group showed strongly positive results in the ELISA. None of the animals in the negative control seroconverted during the whole trial.

In a further study it was also seen that respective antibody results were likewise achieved when the mother sows were only vaccinated twice via the intranasal route.

Bacteriology:

Fecal swabs taken at 0 and 2 dpi did not show any pathogenic bacteria. The bacterial flora did not undergo significant changes upon infection.

Clinical Signs:

Piglets of the positive control group (group 2) clearly showed clinical signs indicative for PEDV over 7 days starting with vomiting 24 hpi followed by diarrhea. 8 of 26 of the piglets had to be euthanized due to severe dehydration and clinical score values over 6 (humane endpoint). First clinical signs indicative for PEDV were detectable at 36 hpi.

In total, the clinical signs of the CDV vector vaccinated and PEDV challenged piglets (group 3) were better regarding the general behavior and only 2 of 20 (10%) of the pigs of group 3 had to be euthanized due to severe dehydration and clinical score values over 6 (as compared to 31% of the piglets of group 2).

Animals in the negative control stayed healthy during the whole trial.

Shedding of Virus

A clear difference in virus shedding could be detected between the challenged groups. At 1 dpi all challenged piglets were positive for virus genome in rectal swabs, but animals in the CDV-PEDV vaccinated group showed significantly lower PEDV genome copy numbers (mean CT value 32,79), then in challenge group (mean CT value 26,65).

Also, while for the next five days pi, the genome load in rectal swabs of the CDV group was quite similar to the positive control, beginning at 7 dpi the detectable amount of virus genome declined below the cutoff level in piglets protected by the vaccinated sows, while all animals in the positive control group still shed PEDV.

No PEDV genome could be detected in swabs of the negative control group.

In conclusion, the outcome of the study was that piglets born to sows vaccinated with the CDV PEDV-Spike recombinant vaccine showed a reduction of clinical signs, as compared to the positive control, and in particular, a great improvement was seen with regard to the mortality/letality of the piglets. Furthermore, virus shedding after the PEDV challenge was significantly reduced.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

The following clauses are also disclosed herein:

1. An expression cassette for insertion between two adjacent essential genes (1; 2) of a Paramyxoviridae virus such that the first gene (1) is located in 3' direction and the second gene (2) is located in 5' direction of the expression cassette, wherein said expression cassette comprises
   a first nucleotide sequence, wherein said first nucleotide sequence is a nucleotide sequence of interest, and
   a second nucleotide sequence flanking the 5' end of the first nucleotide sequence, wherein said second nucleotide sequence is the 5' non-coding region of a gene, wherein said gene is selected from the group consisting of the essential genes of a Paramyxoviridae virus excluding the first gene (1), and
   a third nucleotide sequence flanking the 3' end of the first nucleotide sequence, wherein said third nucleotide sequence comprises or consists of the 3' non-coding region of a gene, wherein said gene is selected from the group consisting of the essential genes of a Paramyxoviridae virus excluding the second gene (2).

2. The expression cassette of clause 1, wherein said expression cassette consists of
   said first nucleotide sequence, and
   said second nucleotide sequence, and
   said third nucleotide sequence, and
   a further nucleotide sequence flanking the 5' end of said second nucleotide sequence or flanking the 3' end of said third nucleotide sequence, wherein said further nucleotide sequence is an intergenic sequence of a Paramyxoviridae virus.
3. The expression cassette of clause 1 or 2, wherein said third nucleotide sequence consists of
the 3' non-coding region of a gene selected from the group consisting of the essential genes of a Paramyxoviridae virus excluding the second gene (2), and
a sequence flanking the 5' end of said 3' non-coding region, wherein said sequence flanking the 5' end of said 3' non-coding region encodes a consensus sequence for initiation or enhancing of translation, and wherein said consensus sequence for initiation or enhancing of translation is optionally a Kozak sequence.
4. The expression cassette of any one of clauses 1 to 3, wherein said two adjacent genes (1; 2) of a Paramyxoviridae virus are selected from the group consisting of the essential genes of a Paramyxoviridae virus, and/or
wherein said essential genes of a Paramyxoviridae virus are
the N, P, M, F, H and L gene of a Paramyxoviridae virus, or
the N, P, M, F, HN and L gene of a Paramyxoviridae virus, or
the N, P, M, F, G, and L gene of a Paramyxoviridae virus.
5. The expression cassette of any one of clauses 1 to 4 for insertion between the P gene and the M gene of a Paramyxoviridae virus, wherein
said group consisting of the essential genes of a Paramyxoviridae virus excluding the first gene (1) is the group consisting of the essential genes of a Paramyxoviridae virus excluding the P gene of a Paramyxoviridae virus, and wherein said gene is optionally selected from the group consisting of the N, M, F, H and L gene of a Paramyxoviridae virus, and
said group consisting of the essential genes of a Paramyxoviridae virus excluding the second gene (2) is the group consisting of the essential genes of a Paramyxoviridae virus excluding the M gene of a Paramyxoviridae virus, and wherein said gene is optionally selected from the group consisting of the H, P, F, L and N gene of a Paramyxoviridae virus.
6. The expression cassette of any one of clauses 1 to 5, wherein
said second nucleotide sequence is the 5' non-coding region of a gene selected from the essential genes of a Paramyxoviridae virus located in 3' direction of the expression cassette, excluding the 5' non-coding region of the first gene (1), and/or
said third nucleotide sequence comprises or consists of the 3' non-coding region of an essential gene of a Paramyxoviridae virus located in 5' direction of the expression cassette, excluding the 3' non-coding region of the second gene (2).
7. The expression cassette of any one of clauses 1 to 6, wherein said first nucleotide sequence is operably linked to the gene start (GS) sequence included in said third nucleotide sequence and/or to the genome promoter of a Paramyxoviridae virus.
8. The expression cassette of any one of clauses 1 to 7, wherein said nucleotide sequences are RNA sequences.
9. A Paramyxoviridae virus vector, comprising the expression cassette of any one of clauses 1 to 8.
10. The expression cassette of any one of clauses 1 to 8 or the Paramyxoviridae virus vector of clause 9, wherein said 5' non-coding region is the 5' non-coding region of an N gene of a Paramyxoviridae virus, and/or
said 3' non-coding region is the 3' non-coding region of an H gene of a Paramyxoviridae virus,
and/or wherein said expression cassette is inserted between a P gene and an M gene of a Paramyxoviridae virus.
11. A Paramyxoviridae virus vector, comprising an RNA sequence inserted between two adjacent essential genes (1; 2) of a Paramyxoviridae virus such that the first gene (1) is located in 3' direction and the second gene (2) is located in 5' direction of said inserted RNA sequence, and wherein said inserted RNA sequence comprises or consists of
a first RNA sequence, wherein said first RNA sequence is a nucleotide sequence of interest, and
a second RNA sequence flanking the 5' end of the first RNA sequence, wherein said second RNA sequence is the 5' non-coding region of a gene, wherein said gene is selected from the group consisting of the essential genes of a Paramyxoviridae virus excluding the first gene (1), and
a third RNA sequence flanking the 3' end of the first RNA sequence, wherein said third RNA sequence comprises or consists of the 3' non-coding region of a gene, wherein said gene is selected from the group consisting of the essential genes of a Paramyxoviridae virus excluding the second gene (2).
12. The Paramyxoviridae virus vector of clause 11, wherein said third RNA sequence consists of
the 3' non-coding region of a gene selected from the group consisting of the essential genes of a Paramyxoviridae virus excluding the second gene (2), and
a sequence flanking the 5' end of said 3' non-coding region, wherein said sequence flanking the 5' end of said 3' non-coding region encodes a consensus sequence for initiation or enhancing of translation, and wherein said consensus sequence for initiation or enhancing of translation is optionally a Kozak sequence.
13. The Paramyxoviridae virus vector of clause 11 or 12, further comprising
a fourth RNA sequence flanking the 5' end of the second RNA sequence, wherein said fourth RNA sequence is an intergenic sequence of a Paramyxoviridae virus, and/or
a fifth RNA sequence flanking the 3' end of the fourth RNA sequence, wherein said fifth RNA sequence is an intergenic sequence of a Paramyxoviridae virus.
14. The Paramyxoviridae virus vector of any one of clauses 11 to 13, wherein said two adjacent genes (1; 2) of a Paramyxoviridae virus are selected from the group consisting of the essential genes of a Paramyxoviridae virus, and/or
wherein said essential genes of a Paramyxoviridae virus are
the N, P, M, F, H and L gene of a Paramyxoviridae virus, or
the N, P, M, F, HN and L gene of a Paramyxoviridae virus, or
the N, P, M, F, G, and L gene of a Paramyxoviridae virus.
15. The Paramyxoviridae virus vector of any one of clauses 11 to 14, wherein said two adjacent essential genes (1; 2) of a Paramyxoviridae virus are the P gene and the M gene of a Paramyxoviridae virus, and wherein
said group consisting of the essential genes of a Paramyxoviridae virus excluding the first gene (1) is the group consisting of the essential genes of a Paramyxoviridae virus excluding the P gene of a Paramyxoviridae virus, and wherein said gene is optionally selected from the group consisting of the N, M, F, H and L gene of a Paramyxoviridae virus, and said group consisting of the essential genes of a Paramyxoviridae virus excluding the second gene (2) is the group consisting of the essential genes of a Paramyxoviridae virus excluding the M gene of a Paramyxoviridae virus, and wherein said gene is optionally selected from the group consisting of the H, P, F, L and N gene of a Paramyxoviridae virus.

16. The Paramyxoviridae virus vector of any one of clauses 11 to 15, wherein
   said second nucleotide sequence is the 5' non-coding region of a gene selected from the essential genes of a Paramyxoviridae virus located in 3' direction of the expression cassette, excluding the 5' non-coding region of the first gene (1), and/or
   said third nucleotide sequence comprises or consists of the 3' non-coding region of an essential gene of a Paramyxoviridae virus located in 5' direction of the expression cassette, excluding the 3' non-coding region of the second gene (2).

17. The Paramyxoviridae virus vector of any one of clauses 11 to 16, wherein
   said 5' non-coding region is a 5' non-coding region of an N gene of a Paramyxoviridae virus, and/or
   said 3' non-coding region is a 3' non-coding region of an H gene of a Paramyxoviridae virus.

18. The Paramyxoviridae virus vector of any one of clauses 11 to 17, wherein
   said first RNA sequence is operably linked to the gene start (GS) sequence included in
   said third RNA sequence and/or to the genome promoter of a Paramyxoviridae virus.

19. The expression cassette or the Paramyxoviridae virus vector of any one of the preceding clauses, wherein said Paramyxoviridae virus is a virus of the genus Morbillivirus, and wherein the virus of the genus Morbillivirus is preferably selected from the group consisting of canine distemper virus (CDV), feline morbillivirus (FeMV), and peste-des-petits-ruminants virus (PPRV), and wherein the virus of the genus Morbillivirus is most preferably a canine distemper virus (CDV).

20. The expression cassette or the Paramyxoviridae virus vector of any one of the preceding clauses, wherein said Paramyxoviridae virus is a CDV, and wherein said 5' non-coding region of a gene of a CDV is selected from the group consisting of
   the 5' non-coding region of an N gene of a CDV, wherein the 5' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:1,
   the 5' non-coding region of a P gene of a CDV, wherein the 5' non-coding region of a P gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:2,
   the 5' non-coding region of an M gene of a CDV, wherein the 5' non-coding region of an M gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:3,
   the 5' non-coding region of an F gene of a CDV, wherein the 5' non-coding region of an F gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:4,
   the 5' non-coding region of an H gene of a CDV, wherein the 5' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:5, and
   the 5' non-coding region of an L gene of a CDV, wherein the 5' non-coding region of an L gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:6.

21. The expression cassette or the Paramyxoviridae virus vector of any one of the preceding clauses, wherein said Paramyxoviridae virus is a CDV, and wherein said 3' non-coding region of a gene of a CDV is selected from the group consisting of
   the 3' non-coding region of an H gene of a CDV, wherein the 3' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:7,
   the 3' non-coding region of an N gene of a CDV, wherein the 3' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:8,
   the 3' non-coding region of a P gene of a CDV, wherein the 3' non-coding region of a P gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:9,
   the 3' non-coding region of an M gene of a CDV, wherein the 3' non-coding region of an M gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:10,
   the 3' non-coding region of an F gene of a CDV, wherein the 3' non-coding region of an F gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:11, and
   the 3' non-coding region of an L gene of a CDV, wherein the 3' non-coding region of an L gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:12.

22. The expression cassette or the Paramyxoviridae virus vector of any one of the preceding clauses, wherein said second nucleotide sequence or said second RNA sequence is the 5' non-coding region of an N gene of a CDV, and wherein said 5' non-coding region of an N gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:1.

23. The expression cassette or the Paramyxoviridae virus vector of any one of the preceding clauses, wherein
said 3' non-coding region of a gene selected from the group consisting of the essential genes of a Paramyxoviridae virus excluding the second gene (2) is the 3' non-coding region of an H gene of a CDV, and wherein said 3' non-coding region of an H gene of a CDV preferably consists of or comprises an RNA sequence being at least 70%, 80%, 85%, 90%, 91%, 92%, 93%, 94%, 95%, 96%, 97%, 98%, or 99% identical with the sequence of SEQ ID NO:7, and/or
said sequence flanking the 5' end of said 3' non-coding region sequence encodes a Kozak sequence being 5 to 8 nucleotides in length, and wherein the Kozak sequence preferably consists of or comprises an RNA sequence being at least 70%, 80%, 85%, 90%, 91%, 92%, 93%, 94%, 95%, 96%, 97%, 98%, or 99% identical with the sequence of SEQ ID NO:13.

24. The expression cassette of any one of clauses 2 to 8, and 19 to 23 or the Paramyxoviridae virus vector of any one of clauses 9, and 13 to 23, wherein said intergenic sequence of a Paramyxoviridae virus is an intergenic sequence of a CDV, and wherein said intergenic sequence of a CDV preferably consists of or comprises an RNA sequence being at least 66% identical with the sequence of SEQ ID NO:14.

25. The expression cassette or Paramyxoviridae virus vector of any one of the preceding clauses, wherein said nucleotide sequence of interest is a gene of interest or an antigen encoding sequence, and/or wherein said nucleotide sequence of interest is non-naturally occurring and/or recombinant.

26. The expression cassette or the Paramyxoviridae virus vector of any one of the preceding clauses, wherein said nucleotide sequence of interest is recombinant and/or heterologous and/or exogenous.

27. The expression cassette or the Paramyxoviridae virus vector of any one of the preceding clauses, wherein said nucleotide sequence of interest encodes an antigen from a disease-causing agent, wherein the disease-causing agent is preferably a disease-causing agent capable of infecting a companion animal, such as a canine or feline and/or any other domestic or wild carnivore, or capable of infecting a food producing animal such as swine or cattle.

28. The expression cassette or the Paramyxoviridae virus vector of any one of the preceding clauses, wherein
the Paramyxoviridae virus is a Paramyxoviridae virus capable of infecting an animal of a first biological family, and
the nucleotide sequence of interest encodes an antigen from a disease-causing agent capable of infecting an animal of said first biological family, and wherein said disease-causing agent is preferably different from said Paramyxoviridae virus,
and wherein said animal of said first biological family is preferably selected from the group consisting of an animal of the family canidae, an animal of the family felidae and an animal of the family suidae, and wherein said animal of said first biological family is most preferably a canine, feline or swine such as a dog, cat or pig.

29. The expression cassette or Paramyxoviridae virus vector of clause 28, wherein
said Paramyxoviridae virus capable of infecting an animal of a first biological family is a CDV and
said disease-causing agent capable of infecting an animal of said first biological family is a Canine Parvovirus (CPV),
or wherein
said Paramyxoviridae virus capable of infecting an animal of a first biological family is a La Piedad Michoacán Mexico virus (LPMV) and
said disease-causing agent capable of infecting an animal of said first biological family is a a swine influenza virus (SwIV) or a porcine epidemic diarrhea virus (PEDV).

30. The expression cassette or the Paramyxoviridae virus vector of any one of the preceding clauses, wherein said nucleotide sequence of interest encodes an antigen from a canine parvovirus (CPV), feline parvovirus (FPV), swine influenza virus (SwIV) or porcine epidemic diarrhea virus (PEDV).

31. The expression cassette or the Paramyxoviridae virus vector of any one of the preceding clauses, wherein said nucleotide sequence of interest encodes
a Protoparvovirus capsid protein, and wherein said Protoparvovirus capsid protein is preferably selected from the group consisting of Carnivore protoparvovirus I (CPV or FPV) capsid protein, Primate protoparvovirus 1 capsid protein, Rodent protoparvovirus 1 capsid protein, Rodent protoparvovirus 2 capsid protein, Ungulate parvovirus 1 (PP capsid protein; or
an influenza virus envelope protein, wherein said envelope protein is optionally hemagglutinin and/or wherein said influenza virus is optionally selected from the group consisting of influenza A virus, influenza B virus and influenza C virus, and wherein the influenza A virus is preferably selected from the group of the influenza viruses H3N2, H3N1, H1N1, H1N2, H2N1, H2N3 and H911; or
a coronavirus Spike (S) protein, and wherein said coronavirus S protein is preferably selected from the group consisting of Alpaca coronavirus S protein, Alphacoronavirus 1 S protein, Human coronavirus 229E S protein, Human Coronavirus NL63 S protein, Porcine epidemic diarrhea virus (PEDV) S protein, Human coronavirus OC43 S protein, Human coronavirus HKU1 S protein, Murine coronavirus S protein, Severe acute respiratory syndrome-related coronavirus (SARS-CoV) S protein, Middle East respiratory syndrome-related coronavirus (MERS-CoV) S protein and Avian infectious bronchitis virus (IBV) S protein.

32. The expression cassette or the Paramyxoviridae virus vector of any one of the preceding clauses, wherein said nucleotide sequence of interest encodes
a Canine Parvovirus (CPV) VP2 protein, and wherein said CPV VP2 protein preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:35; or
an H3-subtype hemagglutinin (H3), in particular H3 of a swine influenza virus, and wherein said H3 preferably comprises or consists of an amino acid sequence being at least 70%, 80%, 85%, 90%, 91%, 92%, 93%, 94%, 95%, 96%, 97%, 98%, or 99% identical with the sequence of SEQ ID NO:36; or
a porcine epidemic diarrhea virus (PEDV) spike (S) protein, and wherein said PEDV S protein preferably comprises or consists of an amino acid sequence being at least 70%, 80%, 85%, 90%, 91%, 92%, 93%, 94%, 33. The expression cassette or the Paramyxoviridae virus vector of any one of the preceding clauses, wherein said nucleotide sequence of interest encodes
  a Canine Parvovirus (CPV) VP2 protein, and wherein said sequence encoding a CPV VP2 protein preferably consists of or comprises an RNA sequence being at least 70%, 80%, 85%, 90%, 91%, 92%, 93%, 94%, 95%, 96%, 97%, 98%, or 99% identical with the sequence of SEQ ID NO:15; or
  an H3-subtype hemagglutinin (H3), preferably H3 of a swine influenza virus, and wherein said sequence encoding H3 preferably consists of or comprises an RNA sequence being at least 70%, 80%, 85%, 90%, 91%, 92%, 93%, 94%, 95%, 96%, 97%, 98%, or 99% identical with the sequence of SEQ ID NO:16; or
  a porcine epidemic diarrhea virus (PEDV) spike (S) protein, and wherein said sequence encoding a PEDV S protein preferably consists of or comprises an RNA sequence being at least 70%, 80%, 85%, 90%, 91%, 92%, 93%, 94%, 95%, 96%, 97%, 98%, or 99% identical with the sequence of SEQ ID NO:37 or SEQ ID NO:38.

34. The expression cassette or the Paramyxoviridae virus vector of any one of the preceding clauses, wherein said expression cassette consists of or said Paramyxoviridae virus vector comprises
  a polynucleotide having an RNA sequence being at least 70%, 80%, 85%, 90%, 91%, 92%, 93%, 94%, 95%, 96%, 97%, 98%, or 99% identical with the sequence of SEQ ID NO:17 or SEQ ID NO:18; or
  a polynucleotide having an RNA sequence being at least 70%, 80%, 85%, 90%, 91%, 92%, 93%, 94%, 95%, 96%, 97%, 98%, or 99% identical with the sequence of SEQ ID NO:19 or SEQ ID NO:20; or
  a polynucleotide having an RNA sequence being at least 70%, 80%, 85%, 90%, 91%, 92%, 93%, 94%, 95%, 96%, 97%, 98%, or 99% identical with the sequence of SEQ ID NO:39 or SEQ ID NO:40.

35. The Paramyxoviridae virus vector of any one of the preceding clauses comprising
  an RNA sequence being at least 70%, 80%, 85%, 90%, 91%, 92%, 93%, 94%, 95%, 96%, 97%, 98%, or 99% identical with the sequence of SEQ ID NO:21; or
  an RNA sequence being at least 70%, 80%, 85%, 90%, 91%, 92%, 93%, 94%, 95%, 96%, 97%, 98%, or 99% identical with the sequence of SEQ ID NO:22; or
  an RNA sequence being at least 70%, 80%, 85%, 90%, 91%, 92%, 93%, 94%, 95%, 96%, 97%, 98%, or 99% identical with the sequence of SEQ ID NO:41.

36. The Paramyxoviridae virus vector of any one of clauses 13 to 35, further comprising
  a sixth RNA sequence flanking the 5' end of the fourth RNA sequence, wherein said sixth RNA sequence consists of or comprises an RNA sequence being at least 70%, 80%, 85%, 90%, 91%, 92%, 93%, 94%, 95%, 96%, 97%, 98%, or 99% identical with the sequence of SEQ ID NO:23, and/or
  a seventh RNA sequence flanking the 3' end of the fifth RNA sequence, wherein said seventh RNA sequence consists of or comprises an RNA sequence being at least 70%, 80%, 85%, 90%, 91%, 92%, 93%, 94%, 95%, 96%, 97%, 98%, or 99% identical with the sequence of SEQ ID NO:24.

37. A CDV vector comprising a heterologous nucleotide sequence of interest, wherein said heterologous nucleotide sequence of interest encodes a Canine Parvovirus (CPV) VP2 protein.

38. The CDV vector of clause 37, wherein said heterologous nucleotide sequence of interest encoding a CPV VP2 protein consists of or comprises an RNA sequence being at least 70%, 80%, 85%, 90%, 91%, 92%, 93%, 94%, 95%, 96%, 97%, 98%, or 99% identical with the sequence of SEQ ID NO:15.

39. The CDV vector of clause 37 or 38, wherein said CPV VP2 protein comprises or consists of an amino acid sequence being at least 70%, 80%, 85%, 90%, 91%, 92%, 93%, 94%, 95%, 96%, 97%, 98%, or 99% identical with the sequence of SEQ ID NO:35.

40. The CDV vector of any one of clauses 37 to 39, wherein
  said heterologous nucleotide sequence of interest is located between a P gene and an M gene of a CDV; and/or
  said heterologous nucleotide sequence of interest is operably linked to a gene start (GS) sequence located in 3' direction of said heterologous RNA sequence and/or to the genome promoter of a CDV.

41. The CDV vector of clause 40, wherein said GS sequence is included in an exogenous 3' non-coding region of a gene of a CDV, and wherein said exogenous 3' non-coding region of a gene of a CDV preferably flanks the 3' end of the heterologous nucleotide sequence of interest, and/or wherein said heterologous nucleotide sequence of interest is an RNA sequence of interest.

42. A nucleic acid molecule which encodes the expression cassette or the Paramyxoviridae virus vector of any one of the preceding clauses, and wherein said nucleic acid molecule is preferably a DNA molecule.

43. A DNA molecule, in particular the DNA molecule of clause 42, wherein said molecule comprises
  (i) a DNA sequence encoding a polypeptide of interest,
  (ii) a DNA sequence flanking the 3' end of the sequence of (i) and being at least 70%, 80%, 85%, 90%, 91%, 92%, 93%, 94%, 95%, 96%, 97%, 98%, or 99% identical with the sequence of SEQ ID NO:25,
  (iii) a DNA sequence flanking the 5' end of the sequence of (i) and being at least 70%, 80%, 85%, 90%, 91%, 92%, 93%, 94%, 95%, 96%, 97%, 98%, or 99% identical with the sequence of SEQ ID NO:26, and
  (iv) a DNA sequence flanking the 5' end of the sequence of (iii) and being at least 70%, 80%, 85%, 90%, 91%, 92%, 93%, 94%, 95%, 96%, 97%, 98%, or 99% identical with the sequence of SEQ ID NO:27.

44. The DNA molecule of clause 43, further comprising
  (v) a DNA sequence flanking the 5' end of the sequence of (ii) and being at least 66% identical with the sequence of SEQ ID NO:28, and/or
  (vi) a DNA sequence flanking the 3' end of the sequence of (iv) and being at least 66% identical with the sequence of SEQ ID NO:28.

45. The DNA molecule of clause 44, further comprising
  (vii) a DNA sequence flanking the 3' end of the sequence of (v) and being at least 70%, 80%, 85%, 90%, 91%, 92%, 93%, 94%, 95%, 96%, 97%, 98%, or 99% identical with the sequence of SEQ ID NO:29, and/or
  (viii) a DNA sequence flanking the 5' end of the sequence of (vi) and being at least 70%, 80%, 85%, 90%, 91%, 92%, 93%, 94%, 95%, 96%, 97%, 98%, or 99% identical with the sequence of SEQ ID NO:30.

46. The DNA molecule of any one of clauses 42 to 45, wherein the sequence of (i) is
a DNA sequence encoding a Canine Parvovirus (CPV) VP2 protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:31, or
a DNA sequence encoding an H3-subtype hemagglutinin (H3), preferably H3 of a swine influenza virus, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:32; or
a DNA sequence encoding a PEDV S protein, and wherein said sequence is preferably a DNA sequence being at least 70%, 80%, 85%, 90%, 91%, 92%, 93%, 94%, 95%, 96%, 97%, 98%, or 99% identical with the sequence of SEQ ID NO:42 or SEQ ID NO:43.

47. The DNA molecule of any one of clauses 42 to 46, wherein said DNA molecule comprises
a DNA sequence being at least 70%, 80%, 85%, 90%, 91%, 92%, 93%, 94%, 95%, 96%, 97%, 98%, or 99% identical with the sequence of SEQ ID NO:33; or
a DNA sequence being at least 70%, 80%, 85%, 90%, 91%, 92%, 93%, 94%, 95%, 96%, 97%, 98%, or 99% identical with the sequence of SEQ ID NO:34; or
a DNA sequence being at least 70%, 80%, 85%, 90%, 91%, 92%, 93%, 94%, 95%, 96%, 97%, 98%, or 99% identical with the sequence of SEQ ID NO:44.

48. A mammalian host cell containing the expression cassette or Paramyxoviridae virus vector or DNA acid molecule according to any one of the preceding clauses.

49. The expression cassette or Paramyxoviridae virus vector or nucleic acid molecule according to any one of the preceding clauses for use as a medicament, preferably as a vaccine.

50. A DNA construct comprising a DNA molecule according to any one of clauses 42 to 47.

51. An RNA transcript of the DNA construct of clause 50.

52. A cell transfected with the DNA construct of clause 50.

53. A cell transfected with the RNA transcript of clause 51.

54. A method for the preparation of an infectious Paramyxoviridae virus containing a heterologous gene, in particular for preparing the Paramyxoviridae virus vector of any one of clauses 9 to 41, wherein said method comprises the steps of:
a. providing a host cell expressing a heterologous RNA polymerase;
b. transfecting the host cell with the DNA construct of clause 50, and wherein the DNA molecule is transcribed by the heterologous RNA polymerase, and
c. isolating the viruses produced by the cells.

55. Use of the vector of any one of clauses 9 to 41 or of the cell according to any one of clauses 48, 52 and 53 for the manufacture of an immunogenic composition or a vaccine.

56. An immunogenic composition comprising
the vector according to any one of clauses 9 to 41, wherein said vector is optionally an infectious and/or attenuated virus or said vector is optionally an attenuated and/or modified live virus, and optionally
a recombinant protein expressed by said vector and/or a virus like particle comprising a plurality of a recombinant protein expressed by said vector, and optionally
a pharmaceutical- or veterinary-acceptable carrier or excipient, wherein said carrier is preferably suitable for oral, intradermal, intramuscular or intranasal application.

57. The immunogenic composition of clause 56, wherein said recombinant protein expressed by the vector is
a parvovirus VP2 antigen such as CPV VP2 protein or
an influenza virus envelope protein, wherein said envelope protein is optionally hemagglutinin such as H3.

58. The immunogenic composition of clause 56 or 57, comprising or consisting of
the CDV vector of any one of clauses 37 to 41, and wherein said vector is preferably the vector of any one of clauses 19 to 36, and optionally
a polypeptide or recombinant protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, and optionally
a pharmaceutical- or veterinary-acceptable carrier or excipient, wherein said carrier is preferably suitable for oral, intradermal, intramuscular or intranasal application.

59. The immunogenic composition of clause 56 or 57, comprising or consisting of
the vector of any one of clauses 19 to 36, and wherein said vector is preferably the CDV vector of any one of clauses 37 to 41, and optionally
a recombinant protein expressed by said vector, wherein said recombinant protein comprises or consists of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, and optionally
a pharmaceutical- or veterinary-acceptable carrier or excipient, wherein said carrier is preferably suitable for oral, intradermal, intramuscular or intranasal application.

60. The immunogenic composition of clause 56, wherein said recombinant protein expressed by said vector is a coronavirus S protein, and wherein said coronavirus S protein is optionally a PEDV S protein.

61. The immunogenic composition of clause 56 or 60, wherein said recombinant protein expressed by said vector is a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:45.

62. A vaccine or pharmaceutical composition comprising
a. the vector according to any one of clauses 9 to 41, and
b. a recombinant protein expressed by said vector and/or a virus like particle comprising a plurality of a recombinant protein expressed by said vector, and
c. a pharmaceutical- or veterinary-acceptable carrier or excipient, preferably said carrier is suitable for oral, intradermal, intramuscular or intranasal application, and
d. optionally said vaccine further comprises an adjuvant.

63. The vaccine or pharmaceutical composition according to clause 62, wherein said recombinant protein expressed by the vector is
a parvovirus VP2 antigen such as CPV VP2 protein or
an influenza virus envelope protein, wherein said envelope protein is optionally hemagglutinin such as H3.

64. The vaccine or pharmaceutical composition of clause 62 or 63, comprising or consisting of
   a. the CDV vector of any one of clauses 37 to 41, and wherein said vector is preferably the vector of any one of clauses 19 to 36, and
   b. a polypeptide or recombinant protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, and
   c. a pharmaceutical- or veterinary-acceptable carrier or excipient, preferably said carrier is suitable for oral, intradermal, intramuscular or intranasal application,
   d. and optionally an adjuvant.
65. The vaccine or pharmaceutical composition of clause 62 or 63, comprising or consisting of
   a. the CDV vector of any one of clauses 19 to 36, and wherein said vector is preferably the vector of any one of clauses 37 to 41, and
   b. a recombinant protein expressed by said vector, wherein said recombinant protein comprises or consists of an amino acid sequence being comprising or consisting of an amino acid sequence being at least 70%, 80%, 85%, 90%, 91%, 92%, 93%, 94%, 95%, 96%, 97%, 98%, or 99% identical with the sequence of SEQ ID NO:35 or SEQ ID NO:36, and
   c. a pharmaceutical- or veterinary-acceptable carrier or excipient, preferably said carrier is suitable for oral, intradermal, intramuscular or intranasal application,
   d. and optionally an adjuvant.
66. The vaccine or pharmaceutical composition of clause 62, wherein said recombinant protein expressed by said vector is a coronavirus S protein, and wherein said coronavirus S protein is optionally a PEDV S protein.
67. The vaccine or pharmaceutical composition of clause 62 or 66, wherein said recombinant protein expressed by said vector is a PEDV S protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:45.
68. The immunogenic composition according to any one of clauses 56 to 61 or the vaccine or pharmaceutical composition according to any one of clauses 62 to 67, wherein said vector is the vector of clause 27.
69. The immunogenic composition according to any one of clauses 56 to 61 or the vaccine or pharmaceutical composition according to any one of clauses 62 to 67, wherein said vector is the vector of clause 28.
70. The immunogenic composition according to any one of clauses 56 to 61 or the vaccine or pharmaceutical composition according to any one of clauses 62 to 67, wherein said vector is the vector of clause 29.
71. A method for the preparation of an immunogenic composition or a vaccine for reducing the incidence or the severity of one or more clinical signs associated with or caused by an infection, comprising the following steps:
   a. infecting a mammalian host cell with the vector according to any one of clauses 9 to 41,
   b. cultivating the infected cells under suitable conditions,
   c. collecting infected cell cultures,
   d. optionally purifying the collected infected cell cultures of step c),
   e. optionally mixing said collected infected cell culture with a pharmaceutically acceptable carrier.
72. The method according to clause 71, wherein said immunogenic composition or said vaccine reduces, in particular in an animal, the severity of one or more clinical signs associated with or caused by
   an infection with canine distemper virus (CDV) and/or canine parvovirus (CPV) or
   an infection with an influenza virus, wherein said influenza virus is optionally selected from the group consisting of influenza A virus, influenza B virus and influenza C virus, and wherein the influenza A virus is preferably selected from the group of the influenza viruses H3N2, H3N1, H1N1, H1N2, H2N1, H2N3 and H911, or
   an infection with a coronavirus, wherein said coronavirus is optionally selected from the group consisting of Alpaca coronavirus, Alphacoronavirus 1, Human coronavirus 229E, Human Coronavirus NL63, Porcine epidemic diarrhea virus (PEDV), Human coronavirus OC43, Human coronavirus HKU1, Murine coronavirus, Severe acute respiratory syndrome-related coronavirus (SARS-CoV), Middle East respiratory syndrome-related coronavirus (MERS-CoV) and Avian infectious bronchitis virus (IBV).
73. The immunogenic composition according to any one of clauses 56 to 61 or the vaccine or pharmaceutical composition according to any one of clauses 62 to 67 for use in a method of reducing or preventing the clinical signs or disease caused by an infection with at least one pathogen in an animal or for use in a method of treating or preventing an infection with at least one pathogen in an animal, preferably said animal is a companion animal, such as a canine or feline and/or any other domestic or wild carnivore, or a food producing animal such as swine.
74. The immunogenic composition according to any one of clauses 56 to 61 or the vaccine or pharmaceutical composition according to any one of clauses 62 to 67 for use according to clause 73, wherein said infection with at least one pathogen is
   an infection with CDV and/or CPV or
   an infection with swine influenza virus, wherein the swine influenza virus is optionally a subtype H3 influenza virus, and wherein said subtype H3 influenza virus is preferably a swine influenza virus of the subtype H3N2 or H3N1 or
   an infection with PEDV.
75. The immunogenic composition according to any one of clauses 56 to 61 or the vaccine or pharmaceutical composition according to any one of clauses 62 to 67 for use in a method for
   inducing an immune response against CPV and CDV in an animal, preferably in a canine, or
   inducing an immune response against swine influenza virus in a pig, wherein the swine influenza virus is optionally a subtype H3 influenza virus, and wherein said subtype H3 influenza virus is preferably a swine influenza virus of the subtype H3N2 or H3N1, or
   inducing an immune response against PEDV in a pig, in particular in a preferably pregnant sow.
76. The immunogenic composition according to any one of clauses 56, 60 and 61 or the vaccine or pharmaceutical composition according to any one of clauses 62, 66 and 67 for use in a method of reducing or preventing the clinical signs or disease caused by an infection with a PEDV in a piglet, wherein the piglet is to be suckled by a sow to which the immunogenic composition has been administered.
77. The immunogenic composition for use according to clause 76, wherein said sow to which the immunogenic composition has been administered is a sow to which the immunogenic composition has been administered while said sow has been pregnant, in particular with said piglet.
78. The immunogenic composition according to any one of clauses 56 to 61 or the vaccine or pharmaceutical composition according to any one of clauses 62 to 67 for use according to any of clauses 73 to 77, wherein said immunogenic composition or said vaccine or pharmaceutical composition is to be administered mucosally, preferably intranasally.
79. The immunogenic composition according to any one of clauses 56 to 61 or the vaccine or pharmaceutical composition according to any one of clauses 62 to 67 for use according to any one of clauses 75 to 77, wherein said immunogenic composition or said vaccine or pharmaceutical composition is to be administered mucosally, preferably intranasally, to said sow.
80. A method of immunizing an animal such as a companion animal, such as a canine or feline and/or any other domestic or wild carnivore, or a food producing animal including swine against a clinical disease caused by at least one pathogen in said animal, said method comprising the step of administering to the animal the immunogenic composition according to any one of clauses 56 to 61 or the vaccine or pharmaceutical composition according to any one of clauses 62 to 67, wherein said immunogenic composition or vaccine fails to cause clinical signs of infection but is capable of inducing an immune response that immunizes the animal against pathogenic forms of said at least one pathogen.
81. The method of clause 80,
wherein said at least one pathogen is CDV or CPV or SwIV or PEDV, or
wherein said at least one pathogen is CDV and CPV.
82. A method for inducing the production of antibodies specific for PEDV in a sow, wherein said method comprises administering the immunogenic composition according to any one of clauses 56, 60 and 61 or the vaccine or pharmaceutical composition according to any one of clauses 62, 66 and 67 to said sow.
83. A method of reducing or preventing the clinical signs or disease caused by an infection with a PEDV in a piglet, wherein said method comprises
administering the immunogenic composition according to any one of clauses 56, 60, and 61 or the vaccine or pharmaceutical composition according to any one of clauses 62, 66 and 67 to a sow, and
allowing said piglet to be suckled by said sow.
84. The method of clause 83, wherein said sow is a sow being pregnant, in particular with said pig.
85. The method of clause 83 or 84, comprising the steps of administering the immunogenic composition according to any one of clauses 56, 60, and 61 or the vaccine or pharmaceutical composition according to any one of clauses 62, 66 and 67 to a sow being pregnant with said piglet,
allowing said sow to give birth to said piglet, and
allowing said piglet to be suckled by said sow.
86. The method of any one of clauses 82 to 85, wherein said immunogenic composition or said vaccine or pharmaceutical composition is administered mucosally, preferably intranasally, to said sow.
87. A kit for inducing an immune response against at least one pathogen in an animal or for vaccinating an animal, preferably a companion animal, such as a canine or feline and/or any other domestic or wild carnivore, or food producing animal such as swine or cattle, against a disease associated with and/or reducing the incidence or the severity of one or more clinical signs associated with or caused by at least one pathogen in an animal, comprising:
a) a syringe or a dispenser capable of administering a vaccine to said animal; and
b) the immunogenic composition according to any one of clauses 56 to 61 or the vaccine according to any one of clauses 62 to 67, and
c) optionally an instruction leaflet,
and wherein said at least one pathogen is preferably CDV and/or CPV
or wherein said at least one pathogen is optionally SwIV or PEDV.
88. The method of clause 71 or 72, the immunogenic composition or the vaccine or pharmaceutical composition for use according to any one of clauses 73 to 79, the method according to any one of clause 80 to 86 or the kit according to clause 87, wherein said immunogenic composition is the immunogenic composition of clause 68, and wherein said at least one pathogen is said disease-causing agent of which the antigen encoded by the nucleotide sequence of interest is from.
89. The method of clause 71 or 72, the immunogenic composition or the vaccine or pharmaceutical composition for use according to any one of clauses 73 to 79, the method according to any one of clause 80 to 86 or the kit according to clause 87, wherein said immunogenic composition is the immunogenic composition of clause 69, and wherein said at least one pathogen are said Paramyxoviridae virus and said disease-causing agent of which the antigen encoded by the nucleotide sequence of interest is from.
90. The method of clause 71 or 72, the immunogenic composition or the vaccine or pharmaceutical composition for use according to any one of clauses 73 to 79, the method according to any one of clauses 80 to 86 or the kit according to clause 87, wherein said immunogenic composition is the immunogenic composition of clause 70, and wherein said at least one pathogen are said Paramyxoviridae virus and said disease-causing agent of which the antigen encoded by the nucleotide sequence of interest is from.
91. The method of clause 71 or 72, the immunogenic composition or the vaccine or pharmaceutical composition for use according to any one of clauses 73 to 79, the method according to any one of clauses 80 to 86 or the kit according to clause 87, wherein said immunogenic composition is the immunogenic composition of clause 70, and wherein said at least one pathogen are CDV and CPV.
92. The method of any one of clauses 72, 80, 81, and 88 to 91, wherein said animal is a canine, and wherein said canine is preferably a dog.
93. The method of any one of clauses 72, 80, 81, and 88 to 91, wherein said animal is a feline, and wherein said feline is preferably a cat.
94. The immunogenic composition or the vaccine or pharmaceutical composition for use according to any one of clauses 73 to 75, and 88 to 91, wherein said animal is a canine, and wherein said canine is preferably a dog.
95. The immunogenic composition or the vaccine or pharmaceutical composition for use according to any one of clauses 73 to 75, and 88 to 91, wherein said animal is a feline, and wherein said feline is preferably a cat.
96. The kit according to any one of clauses 87, and 88 to 91, wherein said animal is a canine, and wherein said canine is preferably a dog.

97. The kit according to any one of clauses 87, and 88 to 91, wherein said animal is a feline, and wherein said feline is preferably a cat.

REFERENCES

The following references, to the extent that they provide exemplary procedural or other details supplementary to those set forth herein, are specifically incorporated herein by reference.
1. Parks C L, Wang H P, Kovacs G R, Vasilakis N, Kowalski J, Nowak R M, Lerch R A, Walpita P, Sidhu M S, Udem S A. 2002. Expression of a foreign gene by recombinant canine distemper virus recovered from cloned DNAs. Virus Res; 83(1-2):131-47.
2. von Messling V, Milosevic D, Devaux P, Cattaneo R. 2004. Canine distemper virus and measles virus fusion glycoprotein trimers: partial membrane-proximal ectodomain cleavage enhances function. J Virol. 78(15):7894-903.
3. Wang X, Feng N, Ge J, Shuai L, Peng L, Gao Y, Yang S, Xia X, Bu Z. 2012 Recombinant canine distemper virus serves as bivalent live vaccine against rabies and canine distemper. Vaccine 30(34):5067-72. doi: 10.1016/j.vaccine.2012.06.001. Epub 2012 Jun. 12.
4. Glover S, Anderson C, Piontkowski M, Terry N (2012) Canine Parvovirus (CPV) type 2b vaccine protect puppies with maternal antibodies to CPV when challenged with virulent CPV 2 C virus. International Journal of Applied Research in Veterinary Medicine 10: 217-224
5. Taguchi M, Namikawa K, Maruo T, Orito K, Lynch J, Sahara H. Antibody titers for canine parvovirus type-2, canine distemper virus, and canine adenovirus type-1 in adult household dogs. The Canadian Veterinary Journal. 2011; 52(9):983-986.

What is claimed is:

1. A Paramyxoviridae virus vector comprising an expression cassette inserted between the P gene and the M gene, wherein said expression cassette comprises a first nucleotide sequence, wherein said first nucleotide sequence is a heterologous or exogenous nucleotide sequence of interest, and a second nucleotide sequence flanking the 5' end of the first nucleotide sequence, wherein said second nucleotide sequence is the 5' non-coding region of an N gene of a Paramyxoviridae virus, and a third nucleotide sequence flanking the 3' end of the first nucleotide sequence, wherein said third nucleotide sequence comprises or consists of the 3' non-coding region of an H gene of a Paramyxoviridae virus.

2. The Paramyxoviridae virus vector of claim 1, wherein said expression cassette further comprises an intergenic sequence of a Paramyxoviridae virus flanking the 5' end of said second nucleotide sequence.

3. The Paramyxoviridae virus vector of claim 2, wherein said third nucleotide sequence further comprises a Kozak sequence between the first nucleotide sequence and the 3' non-coding region of an H gene of said Paramyxoviridae virus.

4. The Paramyxoviridae virus vector of claim 3, wherein said nucleotide sequences are RNA sequences, and/or wherein said first nucleotide sequence is operably linked to the gene start (GS) sequence included in said third nucleotide sequence and/or to the genome promoter of a Paramyxoviridae virus.

5. The Paramyxoviridae virus vector of claim 4, wherein said Paramyxoviridae virus is a virus of the genus Morbillivirus, and wherein the virus of the genus Morbillivirus is selected from the group consisting of canine distemper virus (CDV) feline morbillivirus (FeMV), and peste-des-petits-ruminants virus (PPRV).

6. The Paramyxoviridae virus vector of claim 5, wherein said Paramyxoviridae virus is a CDV, and wherein the 5' non-coding region of a gene of a CDV is selected from the group consisting of the 5' non-coding region of an N gene of a CDV, wherein the 5' non-coding region of an N gene of a CDV consists of or comprises an RNA sequence being at least 70%, 80%, 85%, 90%, 91%, 92%, 93%, 94%, 95%, 96%, 97%, 98%, or 99% identical with the sequence of SEQ ID NO:1, and/or wherein the 3' non-coding region of a gene of a CDV is selected from the group consisting of the 3' non-coding region of an H gene of a CDV, wherein the 3' non-coding region of an H gene of a CDV consists of or comprises an RNA sequence being at least 70%, 80%, 85%, 90%, 91%, 92%, 93%, 94%, 95%, 96%, 97%, 98%, or 99% identical with the sequence of SEQ ID NO:7.

7. The Paramyxoviridae virus vector of claim 6, wherein said Paramyxoviridae virus is a CDV, and wherein the 5' non-coding region of a gene of a CDV is selected from the group consisting of the 5' non-coding region of an N gene of a CDV, wherein the 5' non-coding region of an N gene of a CDV consists of or comprises an RNA sequence selected from the group consisting of 95%, 96%, 97%, 98%, 99% and 100% identical with the sequence of SEQ ID NO:1, and/or wherein the 3' non-coding region of a gene of a CDV is selected from the group consisting of the 3' non-coding region of an H gene of a CDV, wherein the 3' non-coding region of an H gene of a CDV consists of or comprises an RNA sequence selected from the group consisting of 95%, 96%, 97%, 98%, 99% and 100% identical with the sequence of SEQ ID NO:7.

8. A mammalian host cell containing the Paramyxoviridae virus vector of claim 6.

9. A vaccine or pharmaceutical composition comprising
   a. the Paramyxoviridae virus vector of claim 6, and
   b. recombinant protein expressed by said vector and/or a virus like particle comprising a plurality of a recombinant protein expressed by said vector, and
   c. pharmaceutical- or veterinary-acceptable carrier or excipient, said carrier is suitable for oral, intradermal, intramuscular or intranasal application, and
   d. optionally said vaccine further comprises an adjuvant; and wherein said recombinant protein expressed by the vector is
   a parvovirus VP2 antigen or
   an influenza virus envelope protein, wherein said envelope protein is optionally hemagglutinin.

10. The vaccine or pharmaceutical composition of claim 9, wherein the vaccine or pharmaceutical composition comprising:
   a. the CDV vector of claim 5, and
   b. a polypeptide or recombinant protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:36, and
   c. a pharmaceutical- or veterinary-acceptable carrier or excipient, said carrier is suitable for oral, intradermal, intramuscular or intranasal application,
   d. and optionally an adjuvant; and
   wherein the vaccine or pharmaceutical composition for use in a method of reducing or preventing the clinical signs or disease caused by an infection with at least one pathogen in an animal, and wherein said infection with at least one pathogen is
   an infection with CDV and/or
   an infection with swine influenza virus, wherein the swine influenza virus is a subtype H3 influenza virus, and wherein said subtype H3 influenza virus is a swine influenza virus of the subtype H3N2 or H3N1.

11. The vaccine or pharmaceutical composition according to claim 9, wherein
   the parvovirus VP2 antigen is CPV VP2 protein or
   the influenza virus envelope protein is-H3.

12. The vaccine or pharmaceutical composition of claim 9, wherein the vaccine or pharmaceutical composition comprising:
   a. the CDV vector of claim 5, and
   b. a polypeptide or recombinant protein comprising or consisting of an amino acid sequence being at least 70%, 80%, 85%, 90%, 91%, 92%, 93%, 94%, 95%, 96%, 97%, 98%, or 99% identical with the sequence of SEQ ID NO:35,
   c. a pharmaceutical- or veterinary-acceptable carrier or excipient, said carrier is suitable for oral, intradermal, intramuscular or intranasal application,
   d. and optionally an adjuvant; and
   wherein the vaccine or pharmaceutical composition for use in a method of reducing or preventing the clinical signs or disease caused by an infection with at least one pathogen in an animal, and wherein said infection with at least one pathogen is
   an infection with CDV and/or CPV.

13. A kit comprising:
   a) a syringe or a dispenser capable of administering a vaccine to said animal; and
   b) the vaccine or pharmaceutical composition of claim 12, and
   optionally an instruction leaflet.

14. A nucleic acid molecule which encodes the expression cassette of claim 1 and wherein said nucleic acid molecule is a DNA molecule.

15. A DNA construct comprising the DNA molecule according to claim 14.

16. A mammalian host cell containing the nucleic acid molecule of claim 14.

17. An immunogenic composition comprising the nucleic acid molecule of claim 14.

18. A mammalian host cell containing the expression cassette of claim 1.

19. An immunogenic composition comprising the Paramyxoviridae virus vector of claim 1.

20. A method for the preparation of the Paramyxoviridae virus vector of claim 6, wherein said method comprises the steps of:
   a. providing a host cell expressing a heterologous RNA polymerase;
   b. transfecting the host cell with the DNA construct of claim 14, and wherein the DNA molecule is transcribed by the heterologous RNA polymerase, and
   c. isolating the viruses produced by the cells.

* * * * *